United States Patent [19]

Scarborough

[11] Patent Number: 5,449,662
[45] Date of Patent: Sep. 12, 1995

[54] ATRIAL NATRIURETIC PEPTIDE CLEARANCE INHIBITORS WHICH RESIST DEGRADATION

[75] Inventor: Robert M. Scarborough, Hayward, Calif.

[73] Assignee: Scios Nova Inc., Mountain View, Calif.

[21] Appl. No.: 840,665

[22] Filed: Feb. 20, 1992

Related U.S. Application Data

[63] Continuation of Ser. No. 644;876, Jan. 23, 1991, abandoned, Ser. No. 286,640, Dec. 15, 1988, abandoned, which is a continuation-in-part of Ser. No. 233,650, Aug. 18, 1988, abandoned.

[51] Int. Cl.⁶ .......................... C07K 7/06; C07K 7/08; C07K 7/10
[52] U.S. Cl. ........................ 514/17; 514/13; 514/14; 514/15; 514/16; 514/12; 530/324; 530/325; 530/326; 530/327; 530/328
[58] Field of Search ...................... 514/12–17; 530/324–328

[56] References Cited

U.S. PATENT DOCUMENTS

| | | |
|---|---|---|
| 4,513,009 | 4/1985 | Roques et al. |
| 4,610,816 | 9/1986 | Berger |
| 4,740,499 | 4/1988 | Olins |
| 4,749,688 | 6/1988 | Haslanger et al. |
| 4,757,048 | 7/1988 | Lewicki et al. |
| 4,804,650 | 2/1989 | Lewicki et al. ............. 530/328 |
| 5,047,397 | 9/1991 | Scarborough et al. ............. 514/12 |

FOREIGN PATENT DOCUMENTS

| | | |
|---|---|---|
| 0038046 | 1/1984 | European Pat. Off. |
| 0117429 | 5/1984 | European Pat. Off. |
| 0233143 | 5/1987 | European Pat. Off. |
| 0254032 | 1/1988 | European Pat. Off. |
| 2194438 | 3/1988 | United Kingdom |

OTHER PUBLICATIONS

Schiller et al., *Biochem. Biophys. Res. Commun.* (1987) 143(2):499–505.
Roques, B. P., et al., *Nature,* 288: 286–288, 1980.
Seymour, A. A., et al., *Life Sciences,* 43: 2265–2274, 1988.
Farrington, G. K., et al., J. Med. Chem., 32: 737–739, 1989.
Seymour, A. A., et al., Hypertension, 14(1): 87–97, Jul. 1989.
Johnson, G. R., et al., J. Biol. Chem., 264 (20): 11637–11642, Jul. 15, 1989.
Krieter, P. A., J. of Pharm. and Exper. Therap., 249(2): 411–417, 1989.
Deschodt-Lanchman, M., et al., Chem. Abs., 109: 32732a, 1988.
Murthy, K. K., Biochem. J., 240: 461–469, 1986.
Kenny, A. J., et al., Chem. Abs., 108(25): 216409m, Jun. 1988.
Bertrand, P., et al., *Biochemical Pharmacology,* 37(20): 3817–3821, 1988.
Olins, G. M., et al., FASEB J., 2: A937, 1988.
Patton, D. R. et al., FASEB J., 2: A937, 1988.
Maack et al., *Science* (1987) 238:675–679.
Fennell et al., *FASEB J.* (1988) 2:A936.
Seymour et al., *FASEB J.* (1988) 2:A936.
Stephenson al., *Biochem. J.* (1987) 243:183–187.
Trapani et al., *FASEB J.* (1988) 2:A936.
McMartin et al., FASEB J. (1988) 2:A936.
Zimmerman et al., *FASEB J.* (1988) 2:A937.
Waksman et al., *Biochem. Biophys. Res. Comm.* (1985) 131:262–268.
Bourgoin et al., *J. Pharm. Exp. Ther.* (1986) 238:360–366.

(List continued on next page.)

*Primary Examiner*—Lester L. Lee
*Attorney, Agent, or Firm*—Morrison & Foerster

[57] ABSTRACT

Compounds with natriuretic, diuretic and/or vasodilation activity which enhance the function of an endogenous ANP are provided. These compounds are capable of both binding to the clearance receptors for ANP and of inhibition of endopeptidase 24.11, an enzyme believed responsible for ANP clearance.

10 Claims, 71 Drawing Sheets

OTHER PUBLICATIONS

Olins et al., *Biochem. Biophys Acta* (1987) 901:97–100.
Koehn et al., *J. Bio. Chem.* (1987) 262:11623–11627.
Yandle et al., *Biochem. Biophys. Res. Comm.* (1987) 146:832–839.
Roques et al., *Nature* (1980) 288:286–288.
Gordon et al., *Life Science* (1983) 33: (supplemental 1) :113–116.
Fournie-Zaluski et al., *J. Med. Chem.* (1983) 26:60–65.
Koepke et al., *FASEB J.* (1988) 2:A527.
Mumford et al., *Biochem. Biophys. Res. Comm.* (1982) 109: 1303–1309.

Acidic: Glu (E), Asp (D); Cysteic (Cya)

Non-Cyclic: Lys (K), Arg (R); Ornithine (Orn)

Basic:

Cyclic: His (H)

FIG. 2A
Z1  F is phenylalanyl; HAF is the hydroxamate thereof:
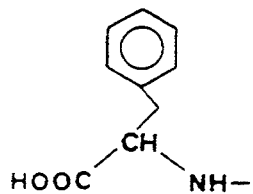 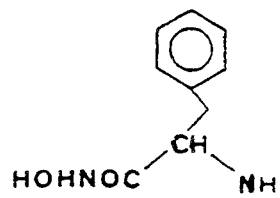
Z2  W is tryptophanyl; HAW is the hydroxamate thereof:
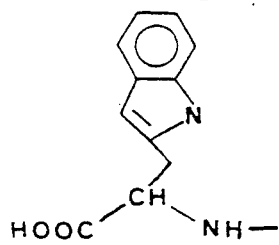 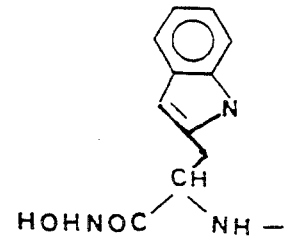
Z3  BF is p-biphenylalanyl; HABF is the hydroxamate thereof:
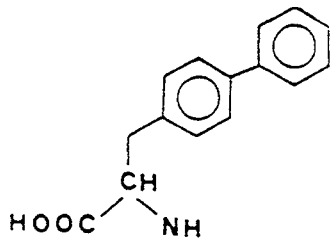 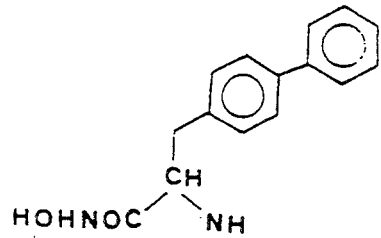
Z4  Nal2 is 3-(2'-naphthyl)alanyl; HANal2 is the hydroxamate thereof:
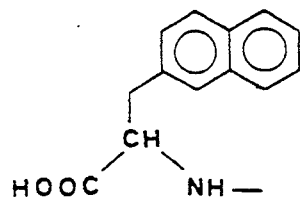 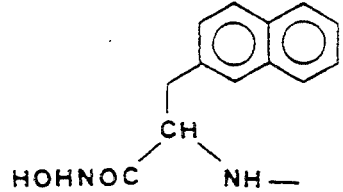

FIG. 2B
Z5  Nal1 is 3-(1'-naphthyl)alanyl; HANal1 is the hydroxamate thereof:
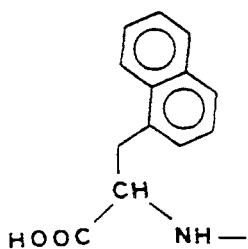 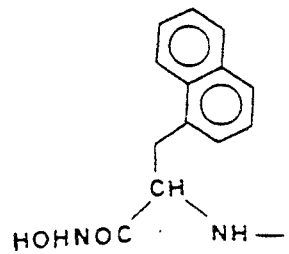
Z6  Cha is 3-(cyclohexyl)alanyl; HACha is the hydroxamate thereof:
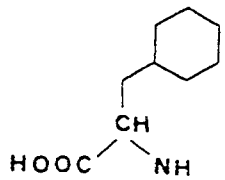 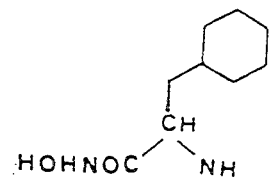
Z7  homoF is homophenylalanyl; HAhomoF is the hydroxamate thereof:
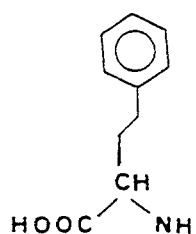 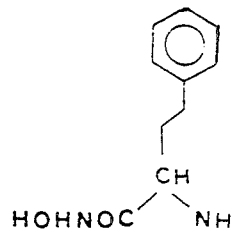

FIG. 2C
Z8   homoCha is 3-(cyclohexylmethyl)alanyl; HAhomoCha is the hydroxamate thereof:
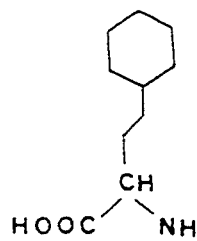                                              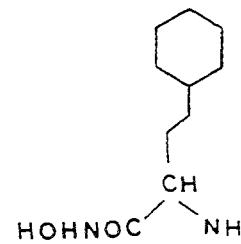
Z9   homoNal2 is 3-(2'-naphthyl methyl)alanyl; HAhomoNal2 is the hydroxamate thereof:
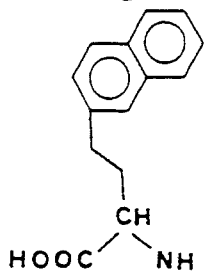                                              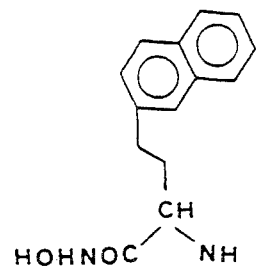
Z10  X[N]F is derivatized phenylalanyl, wherein X is F, homoF, or G, or the hydroxamate thereof:
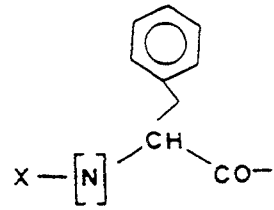

FIG. 2D
Z11  X[N]W is derivatized typtophanyl, wherein X is F, homoF, or G, or the hydroxamate thereof:
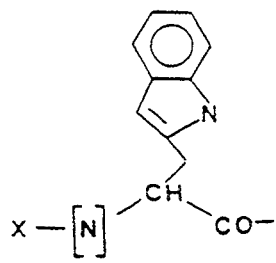
Z12  X[N]BF is derivatized p-biphenylalanyl, wherein X is F, homoF, or G, or the hydroxamate thereof:
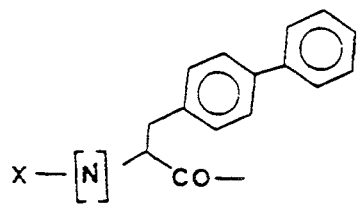
Z13  X[N]Nal2 is derivatized beta-(2'-naphthyl)alanyl, wherein X is F, homoF, or G, or the hydroxamate thereof:
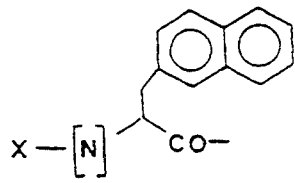

FIG. 2E
Z14 X[N]Nal1 is derivatized 3-(1'-naphthyl)alanyl, wherein X is F, homoF, or G, or the hydroxamate thereof:
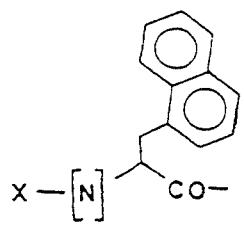
Z15 X[N]Cha is derivatized 3-(cyclohexyl)alanyl, wherein X is F, homoF, or G, or the hydroxamate thereof:
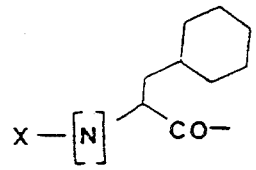
Z16 X[N]homoF is derivatized homophenylalanyl, wherein X is F, homoF, or G, or the hydroxamate thereof:
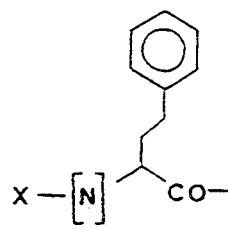

FIG. 2F
Z17 X[N]homoCha is derivatized 3-(cyclohexylmethyl)alanyl, wherein X is F, homoF, or G, or the hydroxamate thereof:
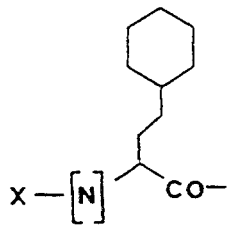
Z18 X[N]Nal2 is derivatized 3-(2'-naphthylmethyl)alanyl, wherein X is F, homoF, or G, or the hydroxamate thereof:
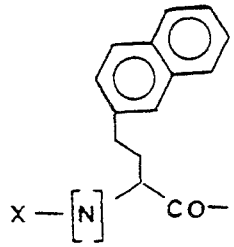
Z19 phosphoryl-F is
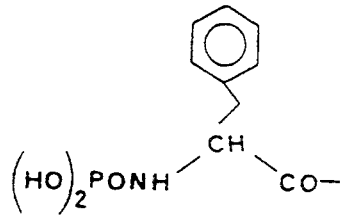

FIG. 2G
Z20   phosphoryl W is
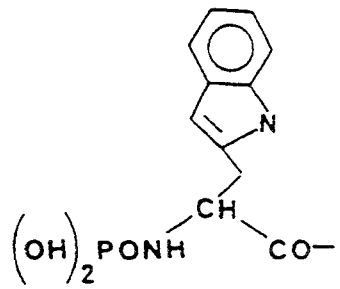
Z21   phosphoryl BF is
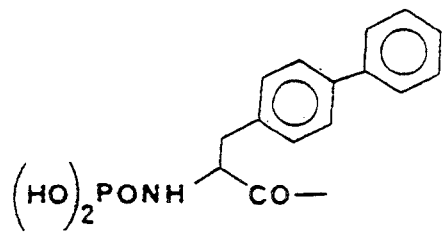
Z22   phosphoryl Nal2 is
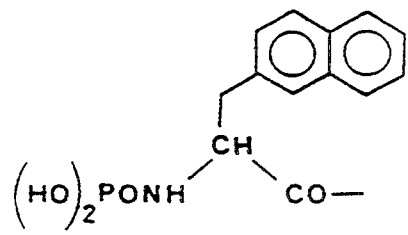
Z23   phosphoryl Nal1 is
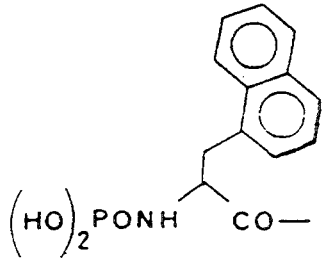

FIG. 2H
Z24 phosphoryl Cha is
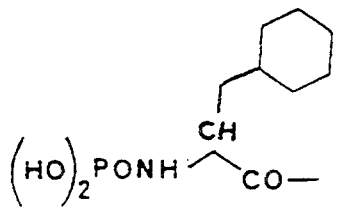
Z25 phosphoryl homoF is
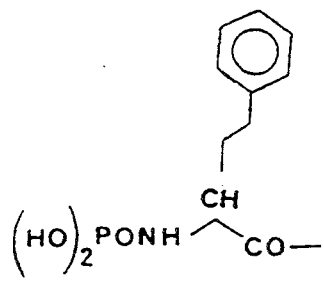
Z26 phosphoryl homoCha is
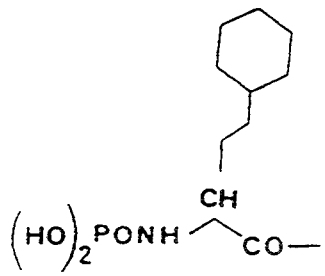
Z27 phosphoryl homoNal2 is
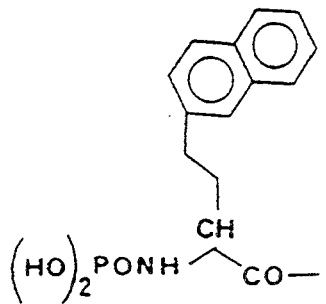

FIG. 21
Z28  MBP is 3-mercapto-2-benzyl-propionyl;
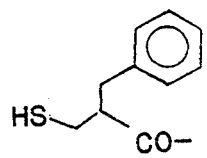
Z29  MPBP is 3-mercapto-2-(p-biphenylmethyl)propionyl:
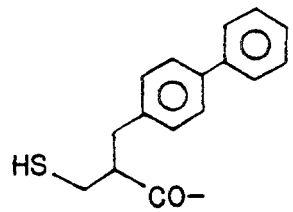
Z30  MNP2 is 3-mercapto-2-(2-'-naphthylmethyl)propionyl:
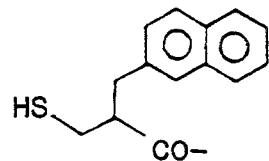
Z31  MNP1 is 3-mercapto-2-(1'-naphthylmethyl)propionyl:
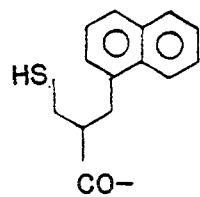

FIG. 2J
Z32  MCP is 3-mercapto-2-cyclohexylmethyl-propionyl:
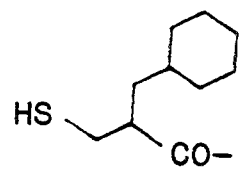
Z33  MPOP is 3-mercapto-2-phenoxy-propionyl:
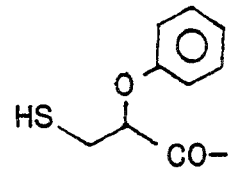
Z34  MNOP2 is 3-mercapto-2-(2'-naphthoxy)propionyl:
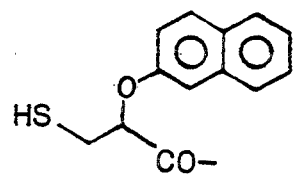
Z35  MIP3 is 3-mercapto-2-(3-indolemethyl)propionyl:
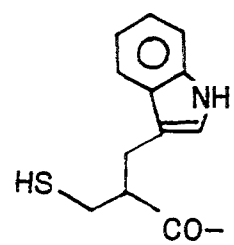

FIG. 2K
Z36  MPEP is 3-mercapto-2-phenylethyl-propionyl:
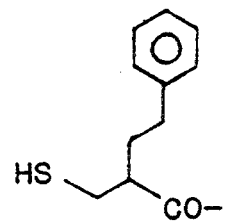
Z37  MCEP is 3-mercapto-2-cyclohexylethyl-propionyl:
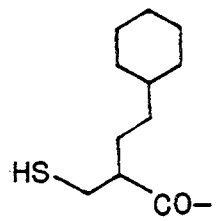
Z38  MNEP2 is 3-mercapto-2-(2'-naphthylethyl)propionyl:
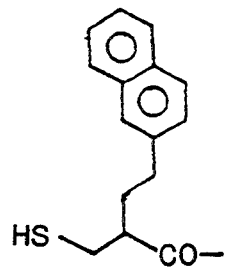
Z39  MBB is 4-mercapto-2-benzyl-butyryl:
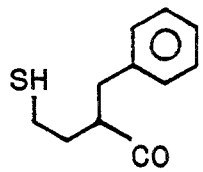

FIG. 2L
Z40  MPBB is 4-mercapto-2-(p-biphenylmethyl)butyryl:
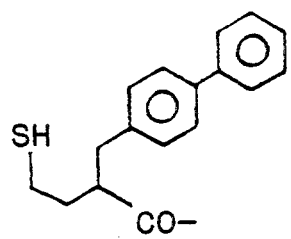
Z41  MNB2 is 4-mercapto-2-(2'-naphthylmethyl)butyryl:
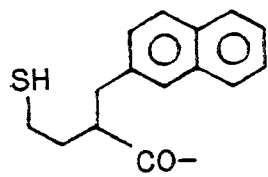
Z42  NMB1 is 4-mercapto-2-(1'-naphthylmethyl)butyryl:
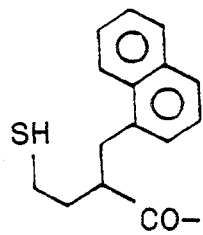
Z43  MCB is 4-mercapto-2-cyclohexylmethyl-butyryl:
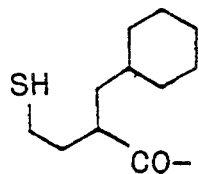

FIG. 2M
Z44  MPOB is 4-mercapto-2-phenoxy-butyryl:
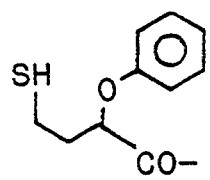
Z45  MNOB2 is 4-mercapto-2-(2'-naphthoxy)butyryl:
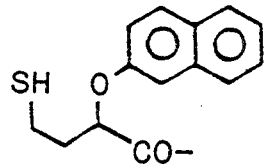
Z46  MIB3 is 4-mercapto-2-(3-indolemethyl)butyryl:
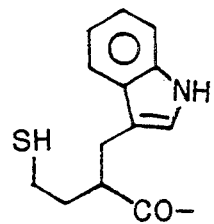
Z47  MPEB is 4-mercapto-2-phenylethyl-butyryl:
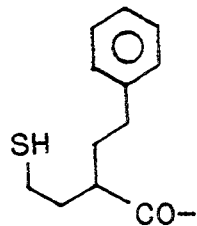

FIG. 2N
Z48  MCEB is 4-mercapto-2-cyclohexylmethyl-butyryl:
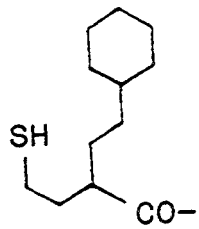
Z49  MNEB2 is 4-mercapto-2-(2'-naphthylethyl)butyryl:
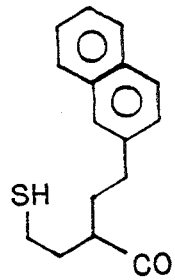
Z50  BMAL is 2-benzylmalonyl:
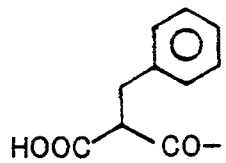
Z51  PBMAL is 2-(p-biphenylmethyl)malonyl:
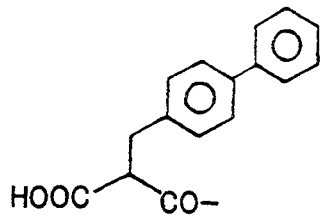

FIG. 20
Z52   NMAL2 is 2-(2'-naphthylmethyl)malonyl:
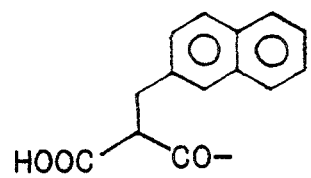
Z53   NMAL1 is 2-(1'-naphthylmethyl)malonyl:
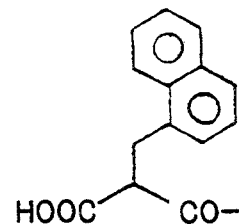
Z54   CMAL is 2-cyclohexylmethylmalonyl:
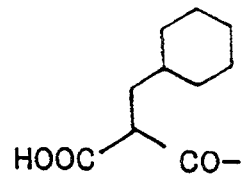
Z55   PMAL is 2-phenoxymalonyl:
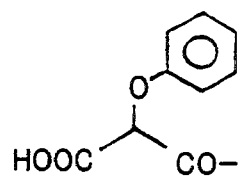

FIG. 2P
Z56  NOMAL2 is 2-(2'-naphthoxy)malonyl:
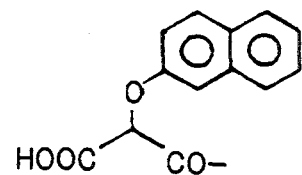
Z57  IMAL is 2-(3-indolemethyl)malonyl:
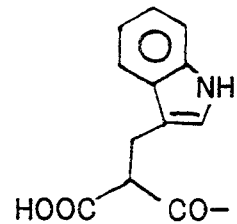
Z58  PEMAL is 2-phenylethylmalonyl:
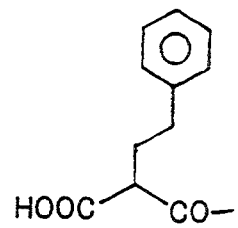
Z59  CEMAL is 2-cyclohexylethylmalonyl:
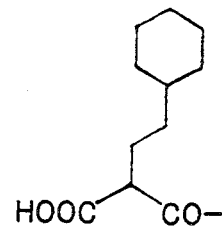

FIG. 2Q
Z60   NEMAL is 2-(2'-naphthylethyl)malonyl:
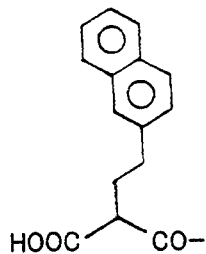
Z61   BHAMAL is 2-benzyl-hydroxyamino-malonyl:
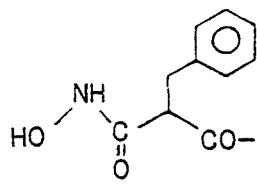
Z62   PBHAMAL is 2-(p-biphenylmethyl)-hydroxyamino-malonyl:
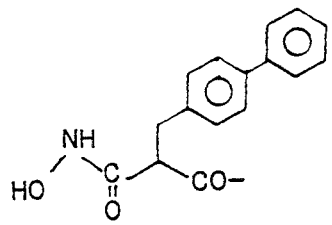
Z63   NHAMAL2 is 2-(2'-naphthylmethyl)-hydroxyamino-malonyl:
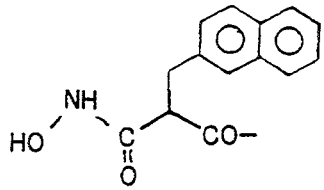

FIG. 2R
Z64  NHAMAL1 is 2-(1'-naphthylmethyl)-hydroxyamino-malonyl:
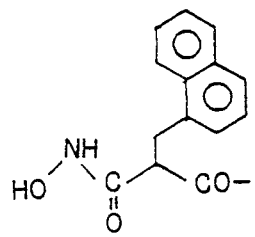
Z65  CHAMAL is 2-cyclohexylmethyl-hydroxyamino-malonyl:
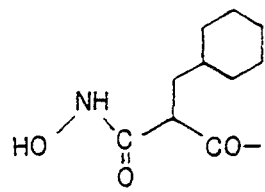
Z66  PHAMAL is 2-phenoxy-hydroxyamino-malonyl:
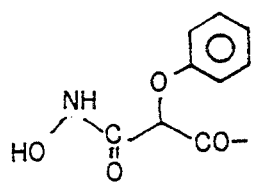
Z67  NOHAMAL2 is 2-(2'-naphthoxy)-hydroxyamino-malonyl:
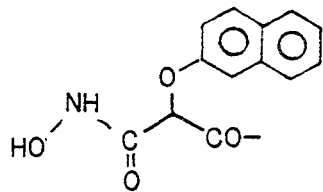

FIG. 2S
Z68 IHAMAL is 2-(3-indolemethyl)-hydroxyamino-malonyl:
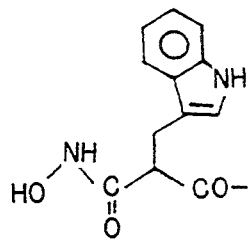
Z69 PEHAMAL is 2-phenylethyl-hydroxyamino-malonyl:
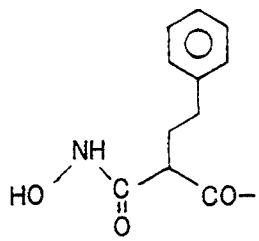
Z70 CEHAMAL is 2-cyclohexylethyl-hydroxyamino-malonyl:
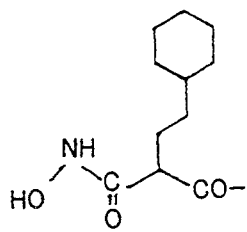
Z71 NEHAMAL is 2-(2'-naphthylethyl)-hydroxyamino-malonyl:
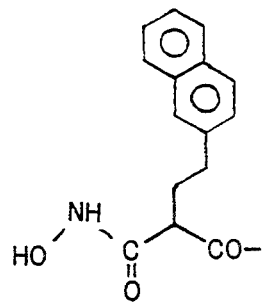

FIG. 2T
Z72  BSUC is 2-benzylsuccinoyl:
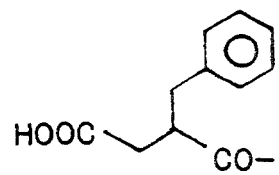
Z73  PBSUC is 2-(p-biphenylmethyl)succinoyl:
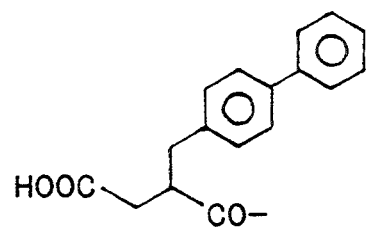
Z74  NSUC1 is 2-(2'-naphthylmethyl)succinoyl:
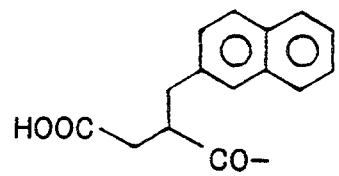
Z75  NSUC2 is 2-(1'-naphthylmethyl)succinoyl:
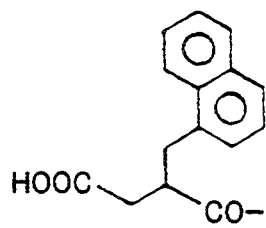

FIG. 2U
Z76  CSUC is 2-cyclohexylmethylsuccinoyl:
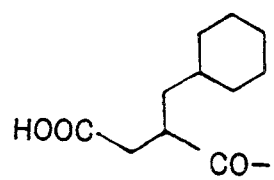
Z77  PSUC is 2-phenoxysuccinoyl:
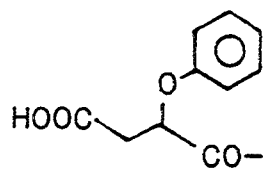
Z78  NOSUC2 is 2-(2'-naphthoxy)succinoyl:
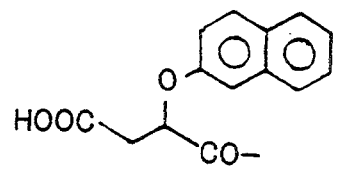
Z79  ISUC is 2-(3'-indolemethyl)succinoyl:
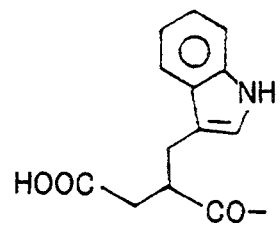

FIG. 2V
Z80  PESUC is 2-phenylethylsuccinoyl:
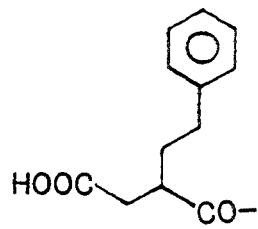
Z81  CESUC is 2-cyclohexylethylsuccinoyl:
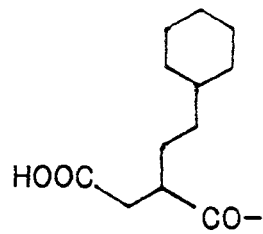
Z82  NESUC is 2-(2'-naphthylethyl)succinoyl:
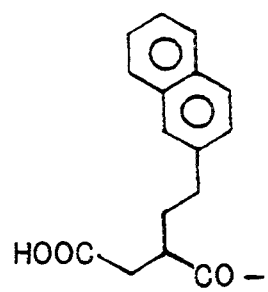
Z83  BHASUC is 2-benzyl-hydroxyamino-succinyl:
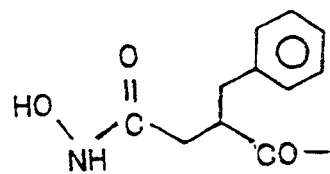

FIG. 2W
Z84 PBHASUC is 2-(p-biphenylmethyl)-hydroxyamino-succinyl:
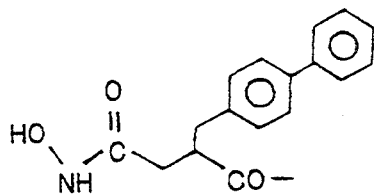
Z85 NHASUC2 is 2-(2'-naphthylmethyl)-hydroxyamino-succinyl:
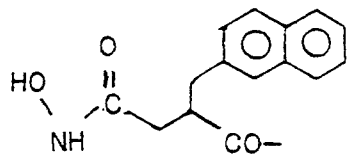
Z86 NHASUC1 is 2-(1'-naphthylmethyl)-hydroxyamino-succinyl:
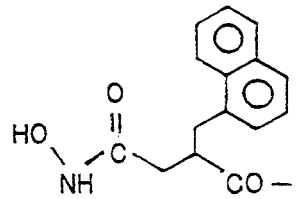
Z87 CHASUC is 2-cyclohexylmethyl-hydroxyamino-succinyl:
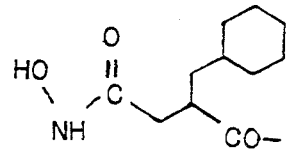

FIG. 2X
Z88  PHASUC is 2-phenoxy-hydroxyamino-succinyl:
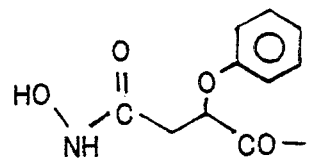
Z89  NOHASUC2 is 2-(2'-naphthoxy)-hydroxyamino-succinyl:
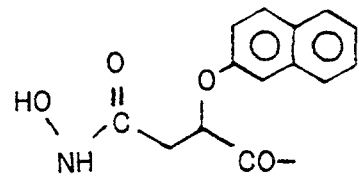
Z90  IHASUC is 2-(3-indolemethyl)-hydroxyamino-succinyl:
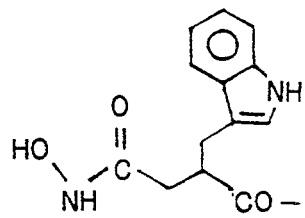
Z91  PEHASUC is 2-phenylethyl-hydroxyamino-succinyl:
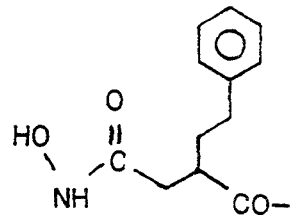

FIG. 2Y
Z92 CEHASUC is 2-cyclohexylethyl-hydroxyamino-succinyl:
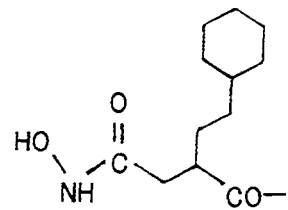
Z93 NEHASUC is 2-(2'-naphthylethyl)-hydroxyamino-succinyl:
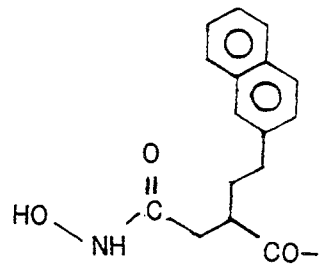

FIG. 3
4-AB is 4-aminobenzoyl:
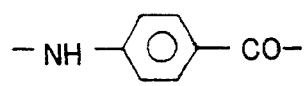
4-APA is 4-aminophenylacetyl:
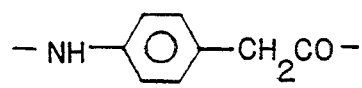
4-PIP is 4-piperidine-carboxyl:
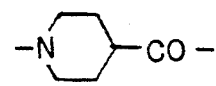
4-AMC is 4-aminomethylcyclohexoyl:
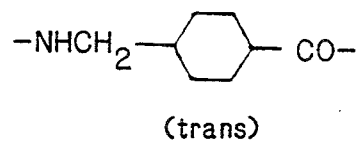
(trans)

FIG. 4A

1. MBP-G-G-R-I-D-R-I-NH$_2$
2. MPBP-G-G-R-I-D-R-I-NH$_2$
3. MNP2-G-G-R-I-D-R-I-NH$_2$
4. MNP1-G-G-R-I-D-R-I-NH$_2$
5. MCP-G-G-R-I-D-R-I-NH$_2$
6. MPOP-G-G-R-I-D-R-I-NH$_2$
7. MNOP2-G-G-R-I-D-R-I-NH$_2$
8. MIP3-G-G-R-I-D-R-I-NH$_2$
9. MPEP-G-G-R-I-D-R-I-NH$_2$
10. MCEP-G-G-R-I-D-R-I-NH$_2$
11. MNEP2-G-G-R-I-D-R-I-NH$_2$
12. MBP-D-G-R-I-D-R-I-NH$_2$
13. MPBP-D-G-R-I-D-R-I-NH$_2$
14. MNP2-D-G-R-I-D-R-I-NH$_2$
15. MNP1-D-G-R-I-D-R-I-NH$_2$
16. MCP-D-G-R-I-D-R-I-NH$_2$
17. MPOP-D-G-R-I-D-R-I-NH$_2$
18. MNOP2-D-G-R-I-D-R-I-NH$_2$
19. MIP3-D-G-R-I-D-R-I-NH$_2$
20. MPEP-D-G-R-I-D-R-I-NH$_2$
21. MCEP-D-G-R-I-D-R-I-NH$_2$
22. MNEP2-D-G-R-I-D-R-I-NH$_2$
23. MBP-[D-Asp]-G-R-I-D-R-I-NH$_2$
24. MPBP-[D-Asp]-G-R-I-D-R-I-NH$_2$
25. MNP2-[D-Asp]-G-R-I-D-R-I-NH$_2$

FIG. 4B

| | |
|---|---|
| 26 | MNP1-[D-Asp]-G-R-I-D-R-I-NH$_2$ |
| 27 | MCP-[D-Asp]-G-R-I-D-R-I-NH$_2$ |
| 28 | MPOP-[D-Asp]-G-R-I-D-R-I-NH$_2$ |
| 29 | MNOP2-[D-Asp]-G-R-I-D-R-I-NH$_2$ |
| 30 | MIP3-[D-Asp]-G-R-I-D-R-I-NH$_2$ |
| 31 | MPEP-[D-Asp]-G-R-I-D-R-I-NH$_2$ |
| 32 | MCEP-[D-Asp]-G-R-I-D-R-I-NH$_2$ |
| 33 | MNEP2-[D-Asp]-G-R-I-D-R-I-NH$_2$ |
| 34 | MBP-[D-Ala]-G-R-I-D-R-I-NH$_2$ |
| 35 | MPBP-[D-Ala]-G-R-I-D-R-I-NH$_2$ |
| 36 | MNP2-[D-Ala]-G-R-I-D-R-I-NH$_2$ |
| 37 | MNP1-[D-Ala]-G-R-I-D-R-I-NH$_2$ |
| 38 | MCP-[D-Ala]-G-R-I-D-R-I-NH$_2$ |
| 39 | MPOP-[D-Ala]-G-R-I-D-R-I-NH$_2$ |
| 40 | MNOP2-[D-Ala]-G-R-I-D-R-I-NH$_2$ |
| 41 | MIP3-[D-Ala]-G-R-I-D-R-I-NH$_2$ |
| 42 | MPEP-[D-Ala]-G-R-I-D-R-I-NH$_2$ |
| 43 | MCEP-[D-Ala]-G-R-I-D-R-I-NH$_2$ |
| 44 | MNEP2-[D-Ala]-G-R-I-D-R-I-NH$_2$ |
| 45 | MBP-[β-L-Asp]-G-R-I-D-R-I-NH$_2$ |
| 46 | MPBP-[β-L-Asp]-G-R-I-D-R-I-NH$_2$ |
| 47 | MNP2-[β-L-Asp]-G-R-I-D-R-I-NH$_2$ |
| 48 | MNP1-[β-L-Asp]-G-R-I-D-R-I-NH$_2$ |
| 49 | MCP-[β-L-Asp]-G-R-I-D-R-I-NH$_2$ |
| 50 | MPOP-[β-L-Asp]-G-R-I-D-R-I-NH$_2$ |
| 51 | MNOP2-[β-L-Asp]-G-R-I-D-R-I-NH$_2$ |
| 52 | MIP3-[β-L-Asp]-G-R-I-D-R-I-NH$_2$ |

| | |
|---|---|
| 53 | MPEP-[β-L-Asp]-G-R-I-D-R-I-NH₂ |
| 54 | MCEP-[β-L-Asp]-G-R-I-D-R-I-NH₂ |
| 55 | MNEP2-[β-L-Asp]-G-R-I-D-R-I-NH₂ |
| 56 | MBP-[β-D-Asp]-G-R-I-D-R-I-NH₂ |
| 57 | MPBP-[β-D-Asp]-G-R-I-D-R-I-NH₂ |
| 58 | MNP2-[β-D-Asp]-G-R-I-D-R-I-NH₂ |
| 59 | MNP1-[β-D-Asp]-G-R-I-D-R-I-NH₂ |
| 60 | MCP-[β-D-Asp]-G-R-I-D-R-I-NH₂ |
| 61 | MPOP-[β-D-Asp]-G-R-I-D-R-I-NH₂ |
| 62 | MNOP2-[β-D-Asp]-G-R-I-D-R-I-NH₂ |
| 63 | MIP3-[β-D-Asp]-G-R-I-D-R-I-NH₂ |
| 64 | MPEP-[β-D-Asp]-G-R-I-D-R-I-NH₂ |
| 65 | MCEP-[β-D-Asp]-G-R-I-D-R-I-NH₂ |
| 66 | MNEP2-[β-D-Asp]-G-R-I-D-R-I-NH₂ |
| 67 | MBP-[γ-D-Glu]-R-I-D-R-I-NH₂ |
| 68 | MPBP-[γ-D-Glu]-R-I-D-R-I-NH₂ |
| 69 | MNP2-[γ-D-Glu]-R-I-D-R-I-NH₂ |
| 70 | MNP1-[γ-D-Glu]-R-I-D-R-I-NH₂ |
| 71 | MCP-[γ-D-Glu]-R-I-D-R-I-NH₂ |
| 72 | MPOP-[γ-D-Glu]-R-I-D-R-I-NH₂ |
| 73 | MNOP2-[γ-D-Glu]-R-I-D-R-I-NH₂ |
| 74 | MIP3-[γ-D-Glu]-R-I-D-R-I-NH₂ |
| 75 | MPEP-[γ-D-Glu]-R-I-D-R-I-NH₂ |
| 76 | MCEP-[γ-D-Glu]-R-I-D-R-I-NH₂ |
| 77 | MNEP2-[γ-D-Glu]-R-I-D-R-I-NH₂ |
| 78 | MBP-[γ-L-Glu]-R-I-D-R-I-NH₂ |
| 79 | MPBP-[γ-L-Glu]-R-I-D-R-I-NH₂ |

| | |
|---|---|
| 80 | MNP2-[γ-L-Glu]-R-I-D-R-I-NH$_2$ |
| 81 | MNP1-[γ-L-Glu]-R-I-D-R-I-NH$_2$ |
| 82 | MCP-[γ-L-Glu]-R-I-D-R-I-NH$_2$ |
| 83 | MPOP-[γ-L-Glu]-R-I-D-R-I-NH$_2$ |
| 84 | MNOP2-[γ-L-Glu]-R-I-D-R-I-NH$_2$ |
| 85 | MIP3-[γ-L-Glu]-R-I-D-R-I-NH$_2$ |
| 86 | MPEP-[γ-L-Glu]-R-I-D-R-I-NH$_2$ |
| 87 | MCEP-[γ-L-Glu]-R-I-D-R-I-NH$_2$ |
| 88 | MNEP2-[γ-L-Glu]-R-I-D-R-I-NH$_2$ |
| 89 | MBP-NH(CH$_2$)$_3$CO-R-I-D-R-I-NH$_2$ |
| 90 | MPBP-NH(CH$_2$)$_3$CO-R-I-D-R-I-NH$_2$ |
| 91 | MNP2-NH(CH$_2$)$_3$CO-R-I-D-R-I-NH$_2$ |
| 92 | MNP1-NH(CH$_2$)$_3$CO-R-I-D-R-I-NH$_2$ |
| 93 | MCP-NH(CH$_2$)$_3$CO-R-I-D-R-I-NH$_2$ |
| 94 | MPOP-NH(CH$_2$)$_3$CO-R-I-D-R-I-NH$_2$ |
| 95 | MNOP2-NH(CH$_2$)$_3$CO-R-I-D-R-I-NH$_2$ |
| 96 | MIP3-NH(CH$_2$)$_3$CO-R-I-D-R-I-NH$_2$ |
| 97 | MPEP-NH(CH$_2$)$_3$CO-R-I-D-R-I-NH$_2$ |
| 98 | MCEP-NH(CH$_2$)$_3$CO-R-I-D-R-I-NH$_2$ |
| 99 | MNEP2-NH(CH$_2$)$_3$CO-R-I-D-R-I-NH$_2$ |
| 100 | MBP-NH(CH$_2$)$_4$CO-R-I-D-R-I-NH$_2$ |
| 101 | MPBP-NH(CH$_2$)$_4$CO-R-I-D-R-I-NH$_2$ |
| 102 | MNP2-NH(CH$_2$)$_4$CO-R-I-D-R-I-NH$_2$ |
| 103 | MNP1-NH(CH$_2$)$_4$CO-R-I-D-R-I-NH$_2$ |
| 104 | MCP-NH(CH$_2$)$_4$CO-R-I-D-R-I-NH$_2$ |
| 105 | MPOP-NH(CH$_2$)$_4$CO-R-I-D-R-I-NH$_2$ |
| 106 | MNOP2-NH(CH$_2$)$_4$CO-R-I-D-R-I-NH$_2$ |

FIG. 4E

| | |
|---|---|
| 107 | MIP3-NH(CH$_2$)$_4$CO-R-I-D-R-I-NH$_2$ |
| 108 | MPEP-NH(CH$_2$)$_4$CO-R-I-D-R-I-NH$_2$ |
| 109 | MCEP-NH(CH$_2$)$_4$CO-R-I-D-R-I-NH$_2$ |
| 110 | MNEP2-NH(CH$_2$)$_4$CO-R-I-D-R-I-NH$_2$ |
| 111 | MBP-4-PIP-R-I-D-R-I-NH$_2$ |
| 112 | MPBP-4-PIP-R-I-D-R-I-NH$_2$ |
| 113 | MNP2-4-PIP-R-I-D-R-I-NH$_2$ |
| 114 | MNP1-4-PIP-R-I-D-R-I-NH$_2$ |
| 115 | MCP-4-PIP-R-I-D-R-I-NH$_2$ |
| 116 | MPOP-4-PIP-R-I-D-R-I-NH$_2$ |
| 117 | MNOP2-4-PIP-R-I-D-R-I-NH$_2$ |
| 118 | MIP3-4-PIP-R-I-D-R-I-NH$_2$ |
| 119 | MPEP-4-PIP-R-I-D-R-I-NH$_2$ |
| 120 | MCEP-4-PIP-R-I-D-R-I-NH$_2$ |
| 121 | MNEP2-4-PIP-R-I-D-R-I-NH$_2$ |
| 122 | MBP-4-APA-R-I-D-R-I-NH$_2$ |
| 123 | MPBP-4-APA-R-I-D-R-I-NH$_2$ |
| 124 | MNP2-4-APA-R-I-D-R-I-NH$_2$ |
| 125 | MNP1-4-APA-R-I-D-R-I-NH$_2$ |
| 126 | MCP-4-APA-R-I-D-R-I-NH$_2$ |
| 127 | MPOP-4-APA-R-I-D-R-I-NH$_2$ |
| 128 | MNOP2-4-APA-R-I-D-R-I-NH$_2$ |
| 129 | MIP3-4-APA-R-I-D-R-I-NH$_2$ |
| 130 | MPEP-4-APA-R-I-D-R-I-NH$_2$ |
| 131 | MCEP-4-APA-R-I-D-R-I-NH$_2$ |
| 132 | MNEP2-4-APA-R-I-D-R-I-NH$_2$ |
| 133 | MBP-4-AB-R-I-D-R-I-NH$_2$ |

FIG. 4F

| | |
|---|---|
| 134 | MPBP-4-AB-R-I-D-R-I-NH$_2$ |
| 135 | MNP2-4-AB-R-I-D-R-I-NH$_2$ |
| 136 | MNP1-4-AB-R-I-D-R-I-NH$_2$ |
| 137 | MCP-4-AB-R-I-D-R-I-NH$_2$ |
| 138 | MPOP-4-AB-R-I-D-R-I-NH$_2$ |
| 139 | MNOP2-4-AB-R-I-D-R-I-NH$_2$ |
| 140 | MIP3-4-AB-R-I-D-R-I-NH$_2$ |
| 141 | MPEP-4-AB-R-I-D-R-I-NH$_2$ |
| 142 | MCEP-4-AB-R-I-D-R-I-NH$_2$ |
| 143 | MNEP2-4-AB-R-I-D-R-I-NH$_2$ |
| 144 | MBP-4-AMC-R-I-D-R-I-NH$_2$ |
| 145 | MPBP-4-AMC-R-I-D-R-I-NH$_2$ |
| 146 | MNP2-4-AMC-R-I-D-R-I-NH$_2$ |
| 147 | MNP1-4-AMC-R-I-D-R-I-NH$_2$ |
| 148 | MCP-4-AMC-R-I-D-R-I-NH$_2$ |
| 149 | MPOP-4-AMC-R-I-D-R-I-NH$_2$ |
| 150 | MNOP2-4-AMC-R-I-D-R-I-NH$_2$ |
| 151 | MIP3-4-AMC-R-I-D-R-I-NH$_2$ |
| 152 | MPEP-4-AMC-R-I-D-R-I-NH$_2$ |
| 153 | MCEP-4-AMC-R-I-D-R-I-NH$_2$ |
| 154 | MNEP2-4-AMC-R-I-D-R-I-NH$_2$ |
| 155 | MBP-G-G-K-I-D-R-I-NH$_2$ |
| 156 | MPBP-G-G-K-I-D-R-I-NH$_2$ |
| 157 | MNP2-G-G-K-I-D-R-I-NH$_2$ |
| 158 | MNP1-G-G-K-I-D-R-I-NH$_2$ |
| 159 | MCP-G-G-K-I-D-R-I-NH$_2$ |
| 160 | MPOP-G-G-K-I-D-R-I-NH$_2$ |

FIG. 4G

| | |
|---|---|
| 161 | MNOP2-G-G-K-I-D-R-I-NH$_2$ |
| 162 | MIP3-G-G-K-I-D-R-I-NH$_2$ |
| 163 | MPEP-G-G-K-I-D-R-I-NH$_2$ |
| 164 | MCEP-G-G-K-I-D-R-I-NH$_2$ |
| 165 | MNEP2-G-G-K-I-D-R-I-NH$_2$ |
| 166 | MBP-4-APA-K-I-D-R-I-NH$_2$ |
| 167 | MPBP-4-APA-K-I-D-R-I-NH$_2$ |
| 168 | MNP2-4-APA-K-I-D-R-I-NH$_2$ |
| 169 | MNP1-4-APA-K-I-D-R-I-NH$_2$ |
| 170 | MCP-4-APA-K-I-D-R-I-NH$_2$ |
| 171 | MPOP-4-APA-K-I-D-R-I-NH$_2$ |
| 172 | MNOP2-4-APA-K-I-D-R-I-NH$_2$ |
| 173 | MIP3-4-APA-K-I-D-R-I-NH$_2$ |
| 174 | MPEP-4-APA-K-I-D-R-I-NH$_2$ |
| 175 | MCEP-4-APA-K-I-D-R-I-NH$_2$ |
| 176 | MNEP2-4-APA-K-I-D-R-I-NH$_2$ |
| 177 | MBP-D-G-K-I-D-R-I-NH$_2$ |
| 178 | MPBP-D-G-K-I-D-R-I-NH$_2$ |
| 179 | MNP2-D-G-K-I-D-R-I-NH$_2$ |
| 180 | MNP1-D-G-K-I-D-R-I-NH$_2$ |
| 181 | MCP-D-G-K-I-D-R-I-NH$_2$ |
| 182 | MPOP-D-G-K-I-D-R-I-NH$_2$ |
| 183 | MNOP2-D-G-K-I-D-R-I-NH$_2$ |
| 184 | MIP3-D-G-K-I-D-R-I-NH$_2$ |
| 185 | MPEP-D-G-K-I-D-R-I-NH$_2$ |
| 186 | MCEP-D-G-K-I-D-R-I-NH$_2$ |
| 187 | MNEP2-D-G-K-I-D-R-I-NH$_2$ |

FIG. 4H

| | |
|---|---|
| 188 | MBP-[D-Asp]-G-K-I-D-R-I-NH$_2$ |
| 189 | MPBP-[D-Asp]-G-K-I-D-R-I-NH$_2$ |
| 190 | MNP2-[D-Asp]-G-K-I-D-R-I-NH$_2$ |
| 191 | MNP1-[D-Asp]-G-K-I-D-R-I-NH$_2$ |
| 192 | MCP-[D-Asp]-G-K-I-D-R-I-NH$_2$ |
| 193 | MPOP-[D-Asp]-G-K-I-D-R-I-NH$_2$ |
| 194 | MNOP2-[D-Asp]-G-K-I-D-R-I-NH$_2$ |
| 195 | MIP3-[D-Asp]-G-K-I-D-R-I-NH$_2$ |
| 196 | MPEP-[D-Asp]-G-K-I-D-R-I-NH$_2$ |
| 197 | MCEP-[D-Asp]-G-K-I-D-R-I-NH$_2$ |
| 198 | MNEP2-[D-Asp]-G-K-I-D-R-I-NH$_2$ |
| 199 | MBP-[γ-L-Glu]-K-I-D-R-I-NH$_2$ |
| 200 | MPBP-[γ-L-Glu]-K-I-D-R-I-NH$_2$ |
| 201 | MNP2-[γ-L-Glu]-K-I-D-R-I-NH$_2$ |
| 202 | MNP1-[γ-L-Glu]-K-I-D-R-I-NH$_2$ |
| 203 | MCP-[γ-L-Glu]-K-I-D-R-I-NH$_2$ |
| 204 | MPOP-[γ-L-Glu]-K-I-D-R-I-NH$_2$ |
| 205 | MNOP2-[γ-L-Glu]-K-I-D-R-I-NH$_2$ |
| 206 | MIP3-[γ-L-Glu]-K-I-D-R-I-NH$_2$ |
| 207 | MPEP-[γ-L-Glu]-K-I-D-R-I-NH$_2$ |
| 208 | MCEP-[γ-L-Glu]-K-I-D-R-I-NH$_2$ |
| 209 | MNEP-[γ-L-Glu]-K-I-D-R-I-NH$_2$ |
| 210 | MBP-[γ-D-Glu]-K-I-D-R-I-NH$_2$ |
| 211 | MPBP-[γ-D-Glu]-K-I-D-R-I-NH$_2$ |
| 212 | MNP2-[γ-D-Glu]-K-I-D-R-I-NH$_2$ |
| 213 | MNP1-[γ-D-Glu]-K-I-D-R-I-NH$_2$ |
| 214 | MCP-[γ-D-Glu]-K-I-D-R-I-NH$_2$ |

FIG. 41

| | |
|---|---|
| 215 | MPOP-[γ-D-Glu]-K-I-D-R-I-NH$_2$ |
| 216 | MNOP2-[γ-D-Glu]-K-I-D-R-I-NH$_2$ |
| 217 | MIP3-[γ-D-Glu]-K-I-D-R-I-NH$_2$ |
| 218 | MPEP-[γ-D-Glu]-K-I-D-R-I-NH$_2$ |
| 219 | MCEP-[γ-D-Glu]-K-I-D-R-I-NH$_2$ |
| 220 | MNEP2-[γ-D-Glu]-K-I-D-R-I-NH$_2$ |
| 221 | MBP-G-G-R-I-D-R-NHCH$_2$CH(CH$_3$)CH$_2$CH$_3$ |
| 222 | MPBP-G-G-R-I-D-R-NHCH$_2$CH(CH$_3$)CH$_2$CH$_3$ |
| 223 | MNP2-G-G-R-I-D-R-NHCH$_2$CH(CH$_3$)CH$_2$CH$_3$ |
| 224 | MNP1-G-G-R-I-D-R-NHCH$_2$CH(CH$_3$)CH$_2$CH$_3$ |
| 225 | MCP-G-G-R-I-D-R-NHCH$_2$CH(CH$_3$)CH$_2$CH$_3$ |
| 226 | MPOP-G-G-R-I-D-R-NHCH$_2$CH(CH$_3$)CH$_2$CH$_3$ |
| 227 | MNOP2-G-G-R-I-D-R-NHCH$_2$CH(CH$_3$)CH$_2$CH$_3$ |
| 228 | MIP3-G-G-R-I-D-R-NHCH$_2$CH(CH$_3$)CH$_2$CH$_3$ |
| 229 | MPEP-G-G-R-I-D-R-NHCH$_2$CH(CH$_3$)CH$_2$CH$_3$ |
| 230 | MCEP-G-G-R-I-D-R-NHCH$_2$CH(CH$_3$)CH$_2$CH$_3$ |
| 231 | MNEP2-G-G-R-I-D-R-NHCH$_2$CH(CH$_3$)CH$_2$CH$_3$ |
| 232 | MBP-4-APA-R-I-D-R-NHCH$_2$CH(CH$_3$)CH$_2$CH$_3$ |
| 233 | MPBP-4-APA-R-I-D-R-NHCH$_2$CH(CH$_3$)CH$_2$CH$_3$ |
| 234 | MNP2-4-APA-R-I-D-R-NHCH$_2$CH(CH$_3$)CH$_2$CH$_3$ |
| 235 | MNP1-4-APA-R-I-D-R-NHCH$_2$CH(CH$_3$)CH$_2$CH$_3$ |
| 236 | MCP-4-APA-R-I-D-R-NHCH$_2$CH(CH$_3$)CH$_2$CH$_3$ |
| 237 | MPOP-4-APA-R-I-D-R-NHCH$_2$CH(CH$_3$)CH$_2$CH$_3$ |
| 238 | MNOP2-4-APA-R-I-D-R-NHCH$_2$CH(CH$_3$)CH$_2$CH$_3$ |
| 239 | MIP3-4-APA-R-I-D-R-NHCH$_2$CH(CH$_3$)CH$_2$CH$_3$ |
| 240 | MPEP-4-APA-R-I-D-R-NHCH$_2$CH(CH$_3$)CH$_2$CH$_3$ |
| 241 | MCEP-4-APA-R-I-D-R-NHCH$_2$CH(CH$_3$)CH$_2$CH$_3$ |

242 MNEP2-4-APA-R-I-D-R-NHCH$_2$CH(CH$_3$)CH$_2$CH$_3$

FIG. 4J

243 MBP-[D-Asp]-G-R-I-D-R-NHCH$_2$CH(CH$_3$)CH$_2$CH$_3$

244 MPBP-[D-Asp]-G-R-I-D-R-NHCH$_2$CH(CH$_3$)CH$_2$CH$_3$

245 MNP2-[D-Asp]-G-R-I-D-R-NHCH$_2$CH(CH$_3$)CH$_2$CH$_3$

246 MNP1-[D-Asp]-G-R-I-D-R-NHCH$_2$CH(CH$_3$)CH$_2$CH$_3$

247 MCP-[D-Asp]-G-R-I-D-R-NHCH$_2$CH(CH$_3$)CH$_2$CH$_3$

248 MPOP-[D-Asp]-G-R-I-D-R-NHCH$_2$CH(CH$_3$)CH$_2$CH$_3$

249 MNOP2-[D-Asp]-G-R-I-D-R-NHCH$_2$CH(CH$_3$)CH$_2$CH$_3$

250 MIP3-[D-Asp]-G-R-I-D-R-NHCH$_2$CH(CH$_3$)CH$_2$CH$_3$

251 MPEP-[D-Asp]-G-R-I-D-R-NHCH$_2$CH(CH$_3$)CH$_2$CH$_3$

252 MCEP-[D-Asp]-G-R-I-D-R-NHCH$_2$CH(CH$_3$)CH$_2$CH$_3$

253 MNEP2-[D-Asp]-G-R-I-D-R-NHCH$_2$CH(CH$_3$)CH$_2$CH$_3$

254 MBP-D-G-R-I-D-R-NHCH$_2$CH(CH$_3$)CH$_2$CH$_3$

255 MPBP-D-G-R-I-D-R-NHCH$_2$CH(CH$_3$)CH$_2$CH$_3$

256 MNP2-D-G-R-I-D-R-NHCH$_2$CH(CH$_3$)CH$_2$CH$_3$

257 MNP1-D-G-R-I-D-R-NHCH$_2$CH(CH$_3$)CH$_2$CH$_3$

258 MCP-D-G-R-I-D-R-NHCH$_2$CH(CH$_3$)CH$_2$CH$_3$

259 MPOP-D-G-R-I-D-R-NHCH$_2$CH(CH$_3$)CH$_2$CH$_3$

260 MNOP2-D-G-R-I-D-R-NHCH$_2$CH(CH$_3$)CH$_2$CH$_3$

261 MIP3-D-G-R-I-D-R-NHCH$_2$CH(CH$_3$)CH$_2$CH$_3$

262 MPEP-D-G-R-I-D-R-NHCH$_2$CH(CH$_3$)CH$_2$CH$_3$

263 MCEP-D-G-R-I-D-R-NHCH$_2$CH(CH$_3$)CH$_2$CH$_3$

264 MNEP2-D-G-R-I-D-R-NHCH$_2$CH(CH$_3$)CH$_2$CH$_3$

265 MBP-[γ-L-Glu]-R-I-D-R-NHCH$_2$CH(CH$_3$)CH$_2$CH$_3$

266 MPBP-[γ-L-Glu]-R-I-D-R-NHCH$_2$CH(CH$_3$)CH$_2$CH$_3$

267 MNP2-[γ-L-Glu]-R-I-D-R-NHCH$_2$CH(CH$_3$)CH$_2$CH$_3$

268 MNP1-[γ-L-Glu]-R-I-D-R-NHCH$_2$CH(CH$_3$)CH$_2$CH$_3$

269    MCP-[γ-L-Glu]-R-I-D-R-NHCH$_2$CH(CH$_3$)CH$_2$CH$_3$

270    MPOP-[γ-L-Glu]-R-I-D-R-NHCH$_2$CH(CH$_3$)CH$_2$CH$_3$

271    MNOP2-[γ-L-Glu]-R-I-D-R-NHCH$_2$CH(CH$_3$)CH$_2$CH$_3$

272    MIP3-[γ-L-Glu]-R-I-D-R-NHCH$_2$CH(CH$_3$)CH$_2$CH$_3$

273    MPEP-[γ-L-Glu]-R-I-D-R-NHCH$_2$CH(CH$_3$)CH$_2$CH$_3$

274    MCEP-[γ-L-Glu]-R-I-D-R-NHCH$_2$CH(CH$_3$)CH$_2$CH$_3$

275    MNEP2-[γ-L-Glu]-R-I-D-R-NHCH$_2$CH(CH$_3$)CH$_2$CH$_3$

276    MBP-[γ-D-Glu]-R-I-D-R-NHCH$_2$CH(CH$_3$)CH$_2$CH$_3$

277    MPBP-[γ-D-Glu]-R-I-D-R-NHCH$_2$CH(CH$_3$)CH$_2$CH$_3$

278    MNP2-[γ-D-Glu]-R-I-D-R-NHCH$_2$CH(CH$_3$)CH$_2$CH$_3$

279    MNP1-[γ-D-Glu]-R-I-D-R-NHCH$_2$CH(CH$_3$)CH$_2$CH$_3$

280    MCP-[γ-D-Glu]-R-I-D-R-NHCH$_2$CH(CH$_3$)CH$_2$CH$_3$

281    MPOP-[γ-D-Glu]-R-I-D-R-NHCH$_2$CH(CH$_3$)CH$_2$CH$_3$

282    MNOP2-[γ-D-Glu]-R-I-D-R-NHCH$_2$CH(CH$_3$)CH$_2$CH$_3$

283    MIP3-[γ-D-Glu]-R-I-D-R-NHCH$_2$CH(CH$_3$)CH$_2$CH$_3$

284    MPEP-[γ-D-Glu]-R-I-D-R-NHCH$_2$CH(CH$_3$)CH$_2$CH$_3$

285    MCEP-[γ-D-Glu]-R-I-D-R-NHCH$_2$CH(CH$_3$)CH$_2$CH$_3$

286    MNEP2-[γ-D-Glu]-R-I-D-R-NHCH$_2$CH(CH$_3$)CH$_2$CH$_3$

287    MBB-G-G-R-I-D-R-I-NH$_2$

288    MPBB-G-G-R-I-D-R-I-NH$_2$

289    MNB2-G-G-R-I-D-R-I-NH$_2$

290    MNB1-G-G-R-I-D-R-I-NH$_2$

291    MCB-G-G-R-I-D-R-I-NH$_2$

292    MPOB-G-G-R-I-D-R-I-NH$_2$

293    MNOB2-G-G-R-I-D-R-I-NH$_2$

294    MIB3-G-G-R-I-D-R-I-NH$_2$

295    MPEB-G-G-R-I-D-R-I-NH$_2$

FIG. 4K

| | |
|---|---|
| 296 | MCEB-G-G-R-I-D-R-I-NH$_2$ |
| 297 | MNEB2-G-G-R-I-D-R-I-NH$_2$ |
| 298 | MBB-4-APA-R-I-D-R-I-NH$_2$ |
| 299 | MPBB-4-APA-R-I-D-R-I-NH$_2$ |
| 300 | MNB2-4-APA-R-I-D-R-I-NH$_2$ |
| 301 | MNB1-4-APA-R-I-D-R-I-NH$_2$ |
| 302 | MCB-4-APA-R-I-D-R-I-NH$_2$ |
| 303 | MPOB-4-APA-R-I-D-R-I-NH$_2$ |
| 304 | MNOB2-4-APA-R-I-D-R-I-NH$_2$ |
| 305 | MIB3-4-APA-R-I-D-R-I-NH$_2$ |
| 306 | MPEB-4-APA-R-I-D-R-I-NH$_2$ |
| 307 | MCEB-4-APA-R-I-D-R-I-NH$_2$ |
| 308 | MNEB2-4-APA-R-I-D-R-I-NH$_2$ |
| 309 | MBB-4-AB-R-I-D-R-I-NH$_2$ |
| 310 | MPBB-4-AB-R-I-D-R-I-NH$_2$ |
| 311 | MNB2-4-AB-R-I-D-R-I-NH$_2$ |
| 312 | MNB1-4-AB-R-I-D-R-I-NH$_2$ |
| 313 | MCB-4-AB-R-I-D-R-I-NH$_2$ |
| 314 | MPOB-4-AB-R-I-D-R-I-NH$_2$ |
| 315 | MNOB2-4-AB-R-I-D-R-I-NH$_2$ |
| 316 | MIB3-4-AB-R-I-D-R-I-NH$_2$ |
| 317 | MPEB-4-AB-R-I-D-R-I-NH$_2$ |
| 318 | MCEB-4-AB-R-I-D-R-I-NH$_2$ |
| 319 | MNEB2-4-AB-R-I-D-R-I-NH$_2$ |
| 320 | MBB-D-G-R-I-D-R-I-NH$_2$ |
| 321 | MPBB-D-G-R-I-D-R-I-NH$_2$ |
| 322 | MNB2-D-G-R-I-D-R-I-NH$_2$ |

FIG. 4L

| | | |
|---|---|---|
| 323 | MNB1-D-G-R-I-D-R-I-NH$_2$ | |
| 324 | MCB-D-G-R-I-D-R-I-NH$_2$ | |
| 325 | MPOB-D-G-R-I-D-R-I-NH$_2$ | |
| 326 | MNOB2-D-G-R-I-D-R-I-NH$_2$ | |
| 327 | MIB3-D-G-R-I-D-R-I-NH$_2$ | |
| 328 | MPEB-D-G-R-I-D-R-I-NH$_2$ | |
| 329 | MCEB-D-G-R-I-D-R-I-NH$_2$ | FIG. 4M |
| 330 | MNEB2-D-G-R-I-D-R-I-NH$_2$ | |
| 331 | MBB-[D-Asp]-G-R-I-D-R-I-NH$_2$ | |
| 332 | MPBB-[D-Asp]-G-R-I-D-R-I-NH$_2$ | |
| 333 | MNB2-[D-Asp]-G-R-I-D-R-I-NH$_2$ | |
| 334 | MNB1-[D-Asp]-G-R-I-D-R-I-NH$_2$ | |
| 335 | MCB-[D-Asp]-G-R-I-D-R-I-NH$_2$ | |
| 336 | MPOB-[D-Asp]-G-R-I-D-R-I-NH$_2$ | |
| 337 | MNOB2-[D-Asp]-G-R-I-D-R-I-NH$_2$ | |
| 338 | MIB3-[D-Asp]-G-R-I-D-R-I-NH$_2$ | |
| 339 | MPEB-[D-Asp]-G-R-I-D-R-I-NH$_2$ | |
| 340 | MCEB-[D-Asp]-G-R-I-D-R-I-NH$_2$ | |
| 341 | MNEB2-[D-Asp]-G-R-I-D-R-I-NH$_2$ | |
| 342 | MBB-[γ-L-Glu]-R-I-D-R-I-NH$_2$ | |
| 343 | MPBB-[γ-L-Glu]-R-I-D-R-I-NH$_2$ | |
| 344 | MNB2-[γ-L-Glu]-R-I-D-R-I-NH$_2$ | |
| 345 | MNB1-[γ-L-Glu]-R-I-D-R-I-NH$_2$ | |
| 346 | MCB-[γ-L-Glu]-R-I-D-R-I-NH$_2$ | |
| 347 | MPOB-[γ-L-Glu]-R-I-D-R-I-NH$_2$ | |
| 348 | MNOB2-[γ-L-Glu]-R-I-D-R-I-NH$_2$ | |
| 349 | MIB3-[γ-L-Glu]-R-I-D-R-I-NH$_2$ | |

| | | |
|---|---|---|
| 350 | MPEB-[γ-L-Glu]-R-I-D-R-I-NH$_2$ | |
| 351 | MCEB-[γ-L-Glu]-R-I-D-R-I-NH$_2$ | |
| 352 | MNEB2-[γ-L-Glu]-R-I-D-R-I-NH$_2$ | |
| 353 | MBB-[γ-D-Glu]-R-I-D-R-I-NH$_2$ | |
| 354 | MPBB-[γ-D-Glu]-R-I-D-R-I-NH$_2$ | |
| 355 | MNB2-[γ-D-Glu]-R-I-D-R-I-NH$_2$ | |
| 356 | MNB1-[γ-D-Glu]-R-I-D-R-I-NH$_2$ | |
| 357 | MCB-[γ-D-Glu]-R-I-D-R-I-NH$_2$ | |
| 358 | MPOB-[γ-D-Glu]-R-I-D-R-I-NH$_2$ | |
| 359 | MNOB2-[γ-D-Glu]-R-I-D-R-I-NH$_2$ | |
| 360 | MIB3-[γ-D-Glu]-R-I-D-R-I-NH$_2$ | |
| 361 | MPEB-[γ-D-Glu]-R-I-D-R-I-NH$_2$ | |
| 362 | MCEB-[γ-D-Glu]-R-I-D-R-I-NH$_2$ | |
| 363 | MNEB2-[γ-D-Glu]-R-I-D-R-I-NH$_2$ | |
| 364 | F[N]G-G-R-I-D-R-I-NH$_2$ | |
| 365 | BF[N]G-G-R-I-D-R-I-NH$_2$ | FIG. 4N |
| 366 | Nal2[N]G-G-R-I-D-R-I-NH$_2$ | |
| 367 | Nal1[N]G-G-R-I-D-R-I-NH$_2$ | |
| 368 | Cha[N]G-G-R-I-D-R-I-NH$_2$ | |
| 369 | W[N]G-G-R-I-D-R-I-NH$_2$ | |
| 370 | homoF[N]G-G-R-I-D-R-I-NH$_2$ | |
| 371 | homoCha[N]G-G-R-I-D-R-I-NH$_2$ | |
| 372 | homoNal2[N]G-G-R-I-D-R-I-NH$_2$ | |
| 373 | F[N]4-APA-R-I-D-R-I-NH$_2$ | |
| 374 | BF[N]4-APA-R-I-D-R-I-NH$_2$ | |
| 375 | Nal2[N]4-APA-R-I-D-R-I-NH$_2$ | |
| 376 | Nal1[N]4-APA-R-I-D-R-I-NH$_2$ | |

| | |
|---|---|
| 377 | Cha[N]4-APA-R-I-D-R-I-NH$_2$ |
| 378 | W[N]4-APA-R-I-D-R-I-NH$_2$ |
| 379 | homoF[N]4-APA-R-I-D-R-I-NH$_2$ |
| 380 | homoCha[N]4-APA-R-I-D-R-I-NH$_2$ |
| 381 | homoNal2[N]4-APA-R-I-D-R-I-NH$_2$ |
| 382 | F[N]4-AB-R-I-D-R-I-NH$_2$ |
| 383 | BF[N]4-AB-R-I-D-R-I-NH$_2$ |
| 384 | Nal2[N]4-AB-R-I-D-R-I-NH$_2$ |
| 385 | Nal1[N]4-AB-R-I-D-R-I-NH$_2$ |
| 386 | Cha[N]4-AB-R-I-D-R-I-NH$_2$ |
| 387 | W[N]4-AB-R-I-D-R-I-NH$_2$ |
| 388 | homoF[N]4-AB-R-I-D-R-I-NH$_2$ |
| 389 | homoCha[N]4-AB-R-I-D-R-I-NH$_2$ |
| 390 | homoNal2[N]4-AB-R-I-D-R-I-NH$_2$ |
| 391 | F[N]D-G-R-I-D-R-I-NH$_2$ |
| 392 | BF[N]D-G-R-I-D-R-I-NH$_2$ |
| 393 | Nal2[N]D-G-R-I-D-R-I-NH$_2$ |
| 394 | Nal1[N]D-G-R-I-D-R-I-NH$_2$ |
| 395 | Cha[N]D-G-R-I-D-R-I-NH$_2$ |
| 396 | W[N]D-G-R-I-D-R-I-NH$_2$ |
| 397 | homoF[N]D-G-R-I-D-R-I-NH$_2$ |
| 398 | homoCha[N]D-G-R-I-D-R-I-NH$_2$ |
| 399 | homoNal2[N]D-G-R-I-D-R-I-NH$_2$ |
| 400 | F[N][D-Asp]-G-R-I-D-R-I-NH$_2$ |
| 401 | BF[N][D-Asp]-G-R-I-D-R-I-NH$_2$ |
| 402 | Nal2[N][D-Asp]-G-R-I-D-R-I-NH$_2$ |
| 403 | Nal1[N][D-Asp]-G-R-I-D-R-I-NH$_2$ |

FIG. 40

| | |
|---|---|
| 404 | Cha[N][D-Asp]-G-R-I-D-R-I-NH$_2$ |
| 405 | W[N][D-Asp]-G-R-I-D-R-I-NH$_2$ |
| 406 | homoF[N][D-Asp]-G-R-I-D-R-I-NH$_2$ |
| 407 | homoCha[N][D-Asp]-G-R-I-I-R-I-NH$_2$ |
| 408 | homoNal2[N][D-Asp]-G-R-I-D-R-I-NH$_2$ |
| 409 | F[N][γ-L-Glu]-R-I-D-R-I-NH$_2$ |
| 410 | BF[N][γ-L-Glu]-R-I-D-R-I-NH$_2$ |
| 411 | Nal2[N][γ-L-Glu]-R-I-D-R-I-NH$_2$ |
| 412 | Nal1[N][γ-L-Glu]-R-I-D-R-I-NH$_2$ |
| 413 | Cha[N][γ-L-Glu]-R-I-D-R-I-NH$_2$ |
| 414 | W[N][γ-L-Glu]-R-I-D-R-I-NH$_2$ |
| 415 | homoF[N][γ-L-Glu]-R-I-D-R-I-NH$_2$ |
| 416 | homoCha[N][γ-L-Glu]-R-I-D-R-I-NH$_2$ |
| 417 | homoNal2[N][γ-L-Glu]-R-I-D-R-I-NH$_2$ |
| 418 | F[N][γ-D-Glu]-R-I-D-R-I-NH$_2$ |
| 419 | BF[N][γ-D-Glu]-R-I-D-R-I-NH$_2$ |
| 420 | Nal2[N][γ-D-Glu]-R-I-D-R-I-NH$_2$ |
| 421 | Nal1[N][γ-D-Glu]-R-I-D-R-I-NH$_2$ |
| 422 | Cha[N][γ-D-Glu]-R-I-D-R-I-NH$_2$ |
| 423 | W[N][γ-D-Glu]-R-I-D-R-I-NH$_2$ |
| 424 | homoF[N][γ-D-Glu]-R-I-D-R-I-NH$_2$ |
| 425 | homoCha[N][γ-D-Glu]-R-I-D-R-I-NH$_2$ |
| 426 | homoNal2[N][γ-D-Glu]-R-I-D-R-I-NH$_2$ |
| 427 | F[N][β-Ala]-G-R-I-D-R-I-NH$_2$ |
| 428 | BF[N][β-Ala]-G-R-I-D-R-I-NH$_2$ |
| 429 | Nal2[N][β-Ala]-G-R-I-D-R-I-NH$_2$ |
| 430 | Nal1[N][β-Ala]-G-R-I-D-R-I-NH$_2$ |

FIG. 4P

| | |
|---|---|
| 431 | Cha[N][β-Ala]-G-R-I-D-R-I-NH$_2$ |
| 432 | W[N][β-Ala]-G-R-I-D-R-I-NH$_2$ |
| 433 | homoF[N][β-Ala]-G-R-I-D-R-I-NH$_2$ |
| 434 | homoCha[N][β-Ala]-G-R-I-D-R-I-NH$_2$ |
| 435 | homoNal2[N][β-Ala]-G-R-I-D-R-I-NH$_2$ |
| 436 | F[N]F-G-G-R-I-D-R-I-NH$_2$ |
| 437 | F[N]BF-G-G-R-I-D-R-I-NH$_2$ |
| 438 | F[N]Nal2-G-G-R-I-D-R-I-NH$_2$ |
| 439 | F[N]Nal1-G-G-R-I-D-R-I-NH$_2$ |
| 440 | F[N]Cha-G-G-R-I-D-R-I-NH$_2$ |
| 441 | F[N]W-G-G-R-I-D-R-I-NH$_2$ |
| 442 | F[N]homoF-G-G-R-I-D-R-I-NH$_2$ |
| 443 | F[N]homoCha-G-G-R-I-D-R-I-NH$_2$ |
| 444 | F[N]homoNal2-G-G-R-I-D-R-I-NH$_2$ |
| 445 | F[N]F-4-APA-R-I-D-R-I-NH$_2$ |
| 446 | F[N]BF-4-APA-R-I-D-R-I-NH$_2$ |
| 447 | F[N]Nal2-4-APA-R-I-D-R-I-NH$_2$ |
| 448 | F[N]Nal1-4-APA-R-I-D-R-I-NH$_2$ |
| 449 | F[N]Cha-4-APA-R-I-D-R-I-NH$_2$ |
| 450 | F[N]W-4-APA-R-I-D-R-I-NH$_2$ |
| 451 | F[N]homoF-4-APA-R-I-D-R-I-NH$_2$ |
| 452 | F[N]homoCha-4-APA-R-I-D-R-I-NH$_2$ |
| 453 | F[N]homoNal2-4-APA-R-I-D-R-I-NH$_2$ |
| 454 | F[N]F-4-AB-R-I-D-R-I-NH$_2$ |
| 455 | F[N]BF-4-AB-R-I-D-R-I-NH$_2$ |
| 456 | F[N]Nal2-4-AB-R-I-D-R-I-NH$_2$ |
| 457 | F[N]Nal1-4-AB-R-I-D-R-I-NH$_2$ |

FIG. 4Q

| | |
|---|---|
| 458 | F[N]Cha-4-AB-R-I-D-R-I-NH$_2$ |
| 459 | F[N]W-4-AB-R-I-D-R-I-NH$_2$ |
| 460 | F[N]homoF-4-AB-R-I-D-R-I-NH$_2$ |
| 461 | F[N]homoCha-4-AB-R-I-D-R-I-NH$_2$ |
| 462 | F[N]homoNal2-4-AB-R-I-D-R-I-NH$_2$ |
| 463 | F[N]F-D-G-R-I-D-R-I-NH$_2$ |
| 464 | F[N]BF-D-G-R-I-D-R-I-NH$_2$ |
| 465 | F[N]Nal2-D-G-R-I-D-R-I-NH$_2$ |
| 466 | F[N]Nal1-D-G-R-I-D-R-I-NH$_2$ |
| 467 | F[N]Cha-D-G-R-I-D-R-I-NH$_2$ |
| 468 | F[N]W-D-G-R-I-D-R-I-NH$_2$ |
| 469 | F[N]homoF-D-G-R-I-D-R-I-NH$_2$ |
| 470 | F[N]homoCha-D-G-R-I-D-R-I-NH$_2$ |
| 471 | F[N]homoNal2-D-G-R-I-D-R-I-NH$_2$ |
| 472 | F[N]F-[D-Asp]-G-R-I-D-R-I-NH$_2$ |
| 473 | F[N]BF-[D-Asp]-G-R-I-D-R-I-NH$_2$ |
| 474 | F[N]Nal2-[D-Asp]-G-R-I-D-R-I-NH$_2$ |
| 475 | F[N]Nal1-[D-Asp]-G-R-I-D-R-I-NH$_2$ |
| 476 | F[N]Cha-[D-Asp]-G-R-I-D-R-I-NH$_2$ |
| 477 | F[N]W-[D-Asp]-G-R-I-D-R-I-NH$_2$ |
| 478 | F[N]homoF-[D-Asp]-G-R-I-D-R-I-NH$_2$ |
| 479 | F[N]homoCha-[D-Asp]-G-R-I-D-R-I-NH$_2$ |
| 480 | F[N]homoNal2-[D-Asp]-G-R-I-D-R-I-NH$_2$ |
| 481 | F[N]F-[γ-L-Glu]-R-I-D-R-I-NH$_2$ |
| 482 | F[N]BF-[γ-L-Glu]-R-I-D-R-I-NH$_2$ |
| 483 | F[N]Nal2-[γ-L-Glu]-R-I-D-R-I-NH$_2$ |
| 484 | F[N]Nal1-[γ-L-Glu]-R-I-D-R-I-NH$_2$ |

FIG. 4R

| | |
|---|---|
| 485 | F[N]Cha-[γ-L-Glu]-R-I-D-R-I-NH$_2$ |
| 486 | F[N]W-[γ-L-Glu]-R-I-D-R-I-NH$_2$ |
| 487 | F[N]homoF-[γ-L-Glu]-R-I-D-R-I-NH$_2$ |
| 488 | F[N]homoCha-[γ-L-Glu]-R-I-D-R-I-NH$_2$ |
| 489 | F[N]homoNal2-[γ-L-Glu]-R-I-D-R-I-NH$_2$ |
| 490 | F[N]F-[γ-D-Glu]-R-I-D-R-I-NH$_2$ |
| 491 | F[N]BF-[γ-D-Glu]-R-I-D-R-I-NH$_2$ |
| 492 | F[N]Nal2-[γ-D-Glu]-R-I-D-R-I-NH$_2$ |
| 493 | F[N]Nal1-[γ-D-Glu]-R-I-D-R-I-NH$_2$ |
| 494 | F[N]Cha-[γ-D-Glu]-R-I-D-R-I-NH$_2$ |
| 495 | F[N]W-[γ-D-Glu]-R-I-D-R-I-NH$_2$ |
| 496 | F[N]homoF-[γ-D-Glu]-R-I-D-R-I-NH$_2$ |
| 497 | F[N]homoCha-[γ-D-Glu]-R-I-D-R-I-NH$_2$ |
| 498 | F[N]homoNal2-[γ-D-Glu]-R-I-D-R-I-NH$_2$ |
| 499 | homoF[N]F-G-G-R-I-D-R-I-NH$_2$ |
| 500 | homoF[N]BF-G-G-R-I-D-R-I-NH$_2$ |
| 501 | homoF[N]Nal2-G-G-R-I-D-R-I-NH$_2$ |
| 502 | homoF[N]Nal1-G-G-R-I-D-R-I-NH$_2$ |
| 503 | homoF[N]Cha-G-G-R-I-D-R-I-NH$_2$ |
| 504 | homoF[N]W-G-G-R-I-D-R-I-NH$_2$ |
| 505 | homoF[N]homoF-G-G-R-I-D-R-I-NH$_2$ |
| 506 | homoF[N]homoCha-G-G-R-I-D-R-I-NH$_2$ |
| 507 | homoF[N]homoNal2-G-G-R-I-D-R-I-NH$_2$ |
| 508 | homoF[N]F-4-APA-R-I-D-R-I-NH$_2$ |
| 509 | homoF[N]BF-4-APA-R-I-D-R-I-NH$_2$ |
| 510 | homoF[N]Nal2-4-APA-R-I-D-R-I-NH$_2$ |
| 511 | homoF[N]Nal1-4-APA-R-I-D-R-I-NH$_2$ |

FIG. 4S

| | |
|---|---|
| 512 | homoF[N]Cha-4-APA-R-I-D-R-I-NH$_2$ |
| 513 | homoF[N]W-4-APA-R-I-D-R-I-NH$_2$ |
| 514 | homoF[N]homoF-4-APA-R-I-D-R-I-NH$_2$ |
| 515 | homoF[N]homoCha-4-APA-R-I-D-R-I-NH$_2$ |
| 516 | homoF[N]homoNal2-4-APA-R-I-D-R-I-NH$_2$ |
| 517 | homoF[N]F-4-AB-R-I-D-R-I-NH$_2$ |
| 518 | homoF[N]BF-4-AB-R-I-D-R-I-NH$_2$ |
| 519 | homoF[N]Nal2-4-AB-R-I-D-R-I-NH$_2$ |
| 520 | homoF[N]Nal1-4-AB-R-I-D-R-I-NH$_2$ |
| 521 | homoF[N]Cha-4-AB-R-I-D-R-I-NH$_2$ |
| 522 | homoF[N]W-4-AB-R-I-D-R-I-NH$_2$ |
| 523 | homoF[N]homoF-4-AB-R-I-D-R-I-NH$_2$ |
| 524 | homoF[N]homoCha-4-AB-R-I-D-R-I-NH$_2$ |
| 525 | homoF[N]homoNal2-4-AB-R-I-D-R-I-NH$_2$ |
| | |
| 527 | homoF[N]BF-D-G-R-I-D-R-I-NH$_2$ |
| 528 | homoF[N]Nal2-D-G-R-I-D-R-I-NH$_2$ |
| 529 | homoF[N]Nal1-D-G-R-I-D-R-I-NH$_2$ |
| 530 | homoF[N]Cha-D-G-R-I-D-R-I-NH$_2$ |
| 531 | homoF[N]W-D-G-R-I-D-R-I-NH$_2$ |
| 532 | homoF[N]homoF-D-G-R-I-D-R-I-NH$_2$ |
| 533 | homoF[N]homoCha-D-G-R-I-D-R-I-NH$_2$ |
| 534 | homoF[N]homoNal2-D-G-R-I-D-R-I-NH$_2$ |
| | |
| 536 | homoF[N]BF-[D-Asp]-G-R-I-D-R-I-NH$_2$ |
| 537 | homoF[N]Nal2-[D-Asp]-G-R-I-D-R-I-NH$_2$ |
| 538 | homoF[N]Nal1-[D-Asp]-G-R-I-D-R-I-NH$_2$ |

FIG. 4T

| | |
|---|---|
| 539 | homoF[N]Cha-[D-Asp]-G-R-I-D-R-I-NH$_2$ |
| 540 | homoF[N]W-[D-Asp]-G-R-I-D-R-I-NH$_2$ |
| 541 | homoF[N]homoF-[D-Asp]-G-R-I-D-R-I-NH$_2$ |
| 542 | homoF[N]homoCha-[D-Asp]-G-R-I-D-R-I-NH$_2$ |
| 543 | homoF[N]homoNal2-[D-Asp]-G-R-I-D-R-I-NH$_2$ |
| 544 | homoF[N]F-[γ-L-Glu]-R-I-D-R-I-NH$_2$ |
| 545 | homoF[N]BF-[γ-L-Glu]-R-I-D-R-I-NH$_2$ |
| 546 | homoF[N]Nal2-[γ-L-Glu]-R-I-D-R-I-NH$_2$ |
| 547 | homoF[N]Nal1-[γ-L-Glu]-R-I-D-R-I-NH$_2$ |
| 548 | homoF[N]Cha-[γ-L-Glu]-R-I-D-R-I-NH$_2$ |
| 549 | homoF[N]W-[γ-L-Glu]-R-I-D-R-I-NH$_2$ |
| 550 | homoF[N]homoF-[γ-L-Glu]-R-I-D-R-I-NH$_2$ |
| 551 | homoF[N]homoCha-[γ-L-Glu]-R-I-D-R-I-NH$_2$ |
| 552 | homoF[N]homoNal2-[γ-L-Glu]-R-I-D-R-I-NH$_2$ |
| 553 | homoF[N]F-[γ-D-Glu]-R-I-D-R-I-NH$_2$ |
| 554 | homoF[N]BF-[γ-D-Glu]-R-I-D-R-I-NH$_2$ |
| 555 | homoF[N]Nal2-[γ-D-Glu]-R-I-D-R-I-NH$_2$ |
| 556 | homoF[N]Nal1-[γ-D-Glu]-R-I-D-R-I-NH$_2$ |
| 557 | homoF[N]Cha-[γ-D-Glu]-R-I-D-R-I-NH$_2$ |
| 558 | homoF[N]W-[γ-D-Glu]-R-I-D-R-I-NH$_2$ |
| 559 | homoF[N]homoF-[γ-D-Glu]-R-I-D-R-I-NH$_2$ |
| 560 | homoF[N]homoCha-[γ-D-Glu]-R-I-D-R-I-NH$_2$ |
| 561 | homoF[N]homoNal2-[γ-D-Glu]-R-I-D-R-I-NH$_2$ |
| 562 | G[N]F-G-G-R-I-D-R-I-NH$_2$ |
| 563 | G[N]BF-G-G-R-I-D-R-I-NH$_2$ |
| 564 | G[N]Nal2-G-G-R-I-D-R-I-NH$_2$ |
| 565 | G[N]Nal1-G-G-R-I-D-R-I-NH$_2$ |

FIG. 4U

| | |
|---|---|
| 566 | G[N]Cha-G-G-R-I-D-R-I-NH$_2$ |
| 567 | G[N]W-G-G-R-I-D-R-I-NH$_2$ |
| 568 | G[N]homoF-G-G-R-I-D-R-I-NH$_2$ |
| 569 | G[N]homoCha-G-G-R-I-D-R-I-NH$_2$ |
| 570 | G[N]homoNal2-G-G-R-I-D-R-I-NH$_2$ |
| 571 | G[N]F-4-APA-R-I-D-R-I-NH$_2$ |
| 572 | G[N]BF-4-APA-R-I-D-R-I-NH$_2$ |
| 573 | G[N]Nal2-4-APA-R-I-D-R-I-NH$_2$ |
| 574 | G[N]Nal1-4-APA-R-I-D-R-I-NH$_2$ |
| 575 | G[N]Cha-4-APA-R-I-D-R-I-NH$_2$ |
| 576 | G[N]W-4-APA-R-I-D-R-I-NH$_2$ |
| 577 | G[N]homoF-4-APA-R-I-D-R-I-NH$_2$ |
| 578 | G[N]homoCha-4-APA-R-I-D-R-I-NH$_2$ |
| 579 | G[N]homoNal2-4-APA-R-I-D-R-I-NH$_2$ |
| 580 | G[N]F-4-AB-R-I-D-R-I-NH$_2$ |
| 581 | G[N]BF-4-AB-R-I-D-R-I-NH$_2$ |
| 582 | G[N]Nal2-4-AB-R-I-D-R-I-NH$_2$ |
| 583 | G[N]Nal1-4-AB-R-I-D-R-I-NH$_2$ |
| 584 | G[N]Cha-4-AB-R-I-D-R-I-NH$_2$ |
| 585 | G[N]W-4-AB-R-I-D-R-I-NH$_2$ |
| 586 | G[N]homoF-4-AB-R-I-D-R-I-NH$_2$ |
| 587 | G[N]homoCha-4-AB-R-I-D-R-I-NH$_2$ |
| 588 | G[N]homoNal2-4-AB-R-I-D-R-I-NH$_2$ |
| 589 | G[N]F-D-G-R-I-D-R-I-NH$_2$ |
| 590 | G[N]BF-D-G-R-I-D-R-I-NH$_2$ |
| 591 | G[N]Nal2-D-G-R-I-D-R-I-NH$_2$ |
| 592 | G[N]Nal1-D-G-R-I-D-R-I-NH$_2$ |

593 G[N]Cha-D-G-R-I-D-R-I-NH$_2$
594 G[N]W-D-G-R-I-D-R-I-NH$_2$
595 G[N]homoF-D-G-R-I-D-R-I-NH$_2$
596 G[N]homoCha-D-G-R-I-D-R-I-NH$_2$
597 G[N]homoNal2-D-G-R-I-D-R-I-NH$_2$
598 G[N]F-[D-Asp]-G-R-I-D-R-I-NH$_2$
599 G[N]BF-[D-Asp]-G-R-I-D-R-I-NH$_2$
600 G[N]Nal2-[D-Asp]-G-R-I-D-R-I-NH$_2$
601 G[N]Nal1-[D-Asp]-G-R-I-D-R-I-NH$_2$
602 G[N]Cha-[D-Asp]-G-R-I-D-R-I-NH$_2$
603 G[N]W-[D-Asp]-G-R-I-D-R-I-NH$_2$
604 G[N]homoF-[D-Asp]-G-R-I-D-R-I-NH$_2$
605 G[N]homoCha-[D-Asp]-G-R-I-D-R-I-NH$_2$
606 G[N]homoNal2-[D-Asp]-G-R-I-D-R-I-NH$_2$
607 G[N]F-[γ-L-Glu]-R-I-D-R-I-NH$_2$
608 G[N]BF-[γ-L-Glu]-R-I-D-R-I-NH$_2$
609 G[N]Nal2-[γ-L-Glu]-R-I-D-R-I-NH$_2$
610 G[N]Nal1-[γ-L-Glu]-R-I-D-R-I-NH$_2$
611 G[N]Cha-[γ-L-Glu]-R-I-D-R-I-NH$_2$
612 G[N]W-[γ-L-Glu]-R-I-D-R-I-NH$_2$
613 G[N]homoF-[γ-L-Glu]-R-I-D-R-I-NH$_2$
614 G[N]homoCha-[γ-L-Glu]-R-I-D-R-I-NH$_2$
615 G[N]homoNal2-[γ-L-Glu]-R-I-D-R-I-NH$_2$
616 G[N]F-[γ-D-Glu]-R-I-D-R-I-NH$_2$
617 G[N]BF-[γ-D-Glu]-R-I-D-R-I-NH$_2$
618 G[N]Nal2-[γ-D-Glu]-R-I-D-R-I-NH$_2$
619 G[N]Nal1-[γ-D-Glu]-R-I-D-R-I-NH$_2$

| | |
|---|---|
| 620 | G[N]Cha-[γ-D-Glu]-R-I-D-R-I-NH$_2$ |
| 621 | G[N]W-[γ-D-Glu]-R-I-D-R-I-NH$_2$ |
| 622 | G[N]homoF-[γ-D-Glu]-R-I-D-R-I-NH$_2$ |
| 623 | G[N]homoCha-[γ-D-Glu]-R-I-D-R-I-NH$_2$ |
| 624 | G[N]homoNal2-[γ-D-Glu]-R-I-D-R-I-NH$_2$ |
| 625 | BMAL-G-G-R-I-D-R-I-NH$_2$ |
| 626 | PBMAL-G-G-R-I-D-R-I-NH$_2$ |
| 627 | NMAL2-G-G-R-I-D-R-I-NH$_2$ |
| 628 | NMAL1-G-G-R-I-D-R-I-NH$_2$ |
| 629 | CMAL-G-G-R-I-D-R-I-NH$_2$ |
| 630 | PMAL-G-G-R-I-D-R-I-NH$_2$ |
| 631 | NOMAL2-G-G-R-I-D-R-I-NH$_2$ |
| 632 | IMAL-G-G-R-I-D-R-I-NH$_2$ |
| 633 | PEMAL-G-G-R-I-D-R-I-NH$_2$ |
| 634 | CEMAL-G-G-R-I-D-R-I-NH$_2$ |
| 635 | NEMAL-G-G-R-I-D-R-I-NH$_2$ |
| 636 | BMAL-4-APA-R-I-D-R-I-NH$_2$ |
| 637 | PBMAL-4-APA-R-I-D-R-I-NH$_2$ |
| 638 | NMAL2-4-APA-R-I-D-R-I-NH$_2$ |
| 639 | NMAL1-4-APA-R-I-D-R-I-NH$_2$ |
| 640 | CMAL-4-APA-R-I-D-R-I-NH$_2$ |
| 641 | PMAL-4-APA-R-I-D-R-I-NH$_2$ |
| 642 | NOMAL2-4-APA-R-I-D-R-I-NH$_2$ |
| 643 | IMAL-4-APA-R-I-D-R-I-NH$_2$ |
| 644 | PEMAL-4-APA-R-I-D-R-I-NH$_2$ |
| 645 | CEMAL-4-APA-R-I-D-R-I-NH$_2$ |
| 646 | NEMAL-4-APA-R-I-D-R-I-NH$_2$ |

FIG. 4X

| | |
|---|---|
| 647 | BMAL-4-AB-R-I-D-R-I-NH$_2$ |
| 648 | PBMAL-4-AB-R-I-D-R-I-NH$_2$ |
| 649 | NMAL2-4-AB-R-I-D-R-I-NH$_2$ |
| 650 | NMAL1-4-AB-R-I-D-R-I-NH$_2$ |
| 651 | CMAL-4-AB-R-I-D-R-I-NH$_2$ |
| 652 | PMAL-4-AB-R-I-D-R-I-NH$_2$ |
| 653 | NOMAL2-4-AB-R-I-D-R-I-NH$_2$ |
| 654 | IMAL-4-AB-R-I-D-R-I-NH$_2$ |
| 655 | PEMAL-4-AB-R-I-D-R-I-NH$_2$ |
| 656 | CEMAL-4-AB-R-I-D-R-I-NH$_2$ |
| 657 | NEMAL-4-AB-R-I-D-R-I-NH$_2$ |
| 658 | BMAL-D-G-R-I-D-R-I-NH$_2$ |
| 659 | PBMAL-D-G-R-I-D-R-I-NH$_2$ |
| 660 | NMAL2-D-G-R-I-D-R-I-NH$_2$ |
| 661 | NMAL1-D-G-R-I-D-R-I-NH$_2$ |
| 662 | CMAL-D-G-R-I-D-R-I-NH$_2$ |
| 663 | PMAL-D-G-R-I-D-R-I-NH$_2$ |
| 664 | NOMAL2-D-G-R-I-D-R-I-NH$_2$ |
| 665 | IMAL-D-G-R-I-D-R-I-NH$_2$ |
| 666 | PEMAL-D-G-R-I-D-R-I-NH$_2$ |
| 667 | CEMAL-D-G-R-I-D-R-I-NH$_2$ |
| 668 | NEMAL-D-G-R-I-D-R-I-NH$_2$ |
| 669 | BMAL-[D-Asp]-G-R-I-D-R-I-NH$_2$ |
| 670 | PBMAL-[D-Asp]-G-R-I-D-R-I-NH$_2$ |
| 671 | NMAL2-[D-Asp]-G-R-I-D-R-I-NH$_2$ |
| 672 | NMAL1-[D-Asp]-G-R-I-D-R-I-NH$_2$ |
| 673 | CMAL-[D-Asp]-G-R-I-D-R-I-NH$_2$ |

FIG. 4Y

| | |
|---|---|
| 674 | PMAL-[D-Asp]-G-R-I-D-R-I-NH$_2$ |
| 675 | NOMAL2-[D-Asp]-G-R-I-D-R-I-NH$_2$ |
| 676 | IMAL-[D-Asp]-G-R-I-D-R-I-NH$_2$ |
| 677 | PEMAL-[D-Asp]-G-R-I-D-R-I-NH$_2$ |
| 678 | CEMAL-[D-Asp]-G-R-I-D-R-I-NH$_2$ |
| 679 | NEMAL-[D-Asp]-G-R-I-D-R-I-NH$_2$ |
| 680 | BMAL-[γ-L-Glu]-R-I-D-R-I-NH$_2$ |
| 681 | PBMAL-[γ-L-Glu]-R-I-D-R-I-NH$_2$ |
| 682 | NMAL2-[γ-L-Glu]-R-I-D-R-I-NH$_2$ |
| 683 | NMAL1-[γ-L-Glu]-R-I-D-R-I-NH$_2$ |
| 684 | CMAL-[γ-L-Glu]-R-I-D-R-I-NH$_2$ |
| 685 | PMAL-[γ-L-Glu]-R-I-D-R-I-NH$_2$ |
| 686 | NOMAL2-[γ-L-Glu]-R-I-D-R-I-NH$_2$ |
| 687 | IMAL-[γ-L-Glu]-R-I-D-R-I-NH$_2$ |
| 688 | PEMAL-[γ-L-Glu]-R-I-D-R-I-NH$_2$ |
| 689 | CEMAL-[γ-L-Glu]-R-I-D-R-I-NH$_2$ |
| 690 | NEMAL-[γ-L-Glu]-R-I-D-R-I-NH$_2$ |
| 691 | BMAL-[γ-D-Glu]-R-I-D-R-I-NH$_2$ |
| 692 | PBMAL-[γ-D-Glu]-R-I-D-R-I-NH$_2$ |
| 693 | NMAL2-[γ-D-Glu]-R-I-D-R-I-NH$_2$ |
| 694 | NMAL1-[γ-D-Glu]-R-I-D-R-I-NH$_2$ |
| 695 | CMAL-[γ-D-Glu]-R-I-D-R-I-NH$_2$ |
| 696 | PMAL-[γ-D-Glu]-R-I-D-R-I-NH$_2$ |
| 697 | NOMAL2-[γ-D-Glu]-R-I-D-R-I-NH$_2$ |
| 698 | IMAL-[γ-D-Glu]-R-I-D-R-I-NH$_2$ |
| 699 | PEMAL-[γ-D-Glu]-R-I-D-R-I-NH$_2$ |
| 700 | CEMAL-[γ-D-Glu]-R-I-D-R-I-NH$_2$ |

| | |
|---|---|
| 701 | NEMAL-[γ-D-Glu]-R-I-D-R-I-NH₂ |
| 702 | HAF[N]G-G-R-I-D-R-I-NH₂ |
| 703 | HABF[N]G-G-R-I-D-R-I-NH₂ |
| 704 | HANal2[N]G-G-R-I-D-R-I-NH₂ |
| 705 | HANal1[N]G-G-R-I-D-R-I-NH₂ |
| 706 | HACha[N]G-G-R-I-D-R-I-NH₂ |
| 707 | HAW[N]G-G-R-I-D-R-I-NH₂ |
| 708 | HAhomoF[N]G-G-R-I-D-R-I-NH₂ |
| 709 | HAhomoCha[N]G-G-R-I-D-R-I-NH₂ |
| 710 | HAhomoNal2[N]G-G-R-I-D-R-I-NH₂ |
| 711 | HAF[N]4-APA-R-I-D-R-I-NH₂ |
| 712 | HABF[N]4-APA-R-I-D-R-I-NH₂ |
| 713 | HANal2[N]4-APA-R-I-D-R-I-NH₂ |
| 714 | NANal1[N]4-APA-R-I-D-R-I-NH₂ |
| 715 | HACha[N]4-APA-R-I-D-R-I-NH₂ |
| 716 | HAW[N]4-APA-R-I-D-R-I-NH₂ |
| 717 | HAhomoF[N]4-APA-R-I-D-R-I-NH₂ |
| 718 | HAhomoCha[N]4-APA-R-I-D-R-I-NH₂ |
| 719 | HAhomoNal2[N]4-APA-R-I-D-R-I-NH₂ |
| 720 | HAF[N]4-AB-R-I-D-R-I-NH₂ |
| 721 | HABF[N]4-AB-R-I-D-R-I-NH₂ |
| 722 | HANal2[N]4-AB-R-I-D-R-I-NH₂ |
| 723 | HANal1[N]4-AB-R-I-D-R-I-NH₂ |
| 724 | HACha[N]4-AB-R-I-D-R-I-NH₂ |
| 725 | HAW[N]4-AB-R-I-D-R-I-NH₂ |
| 726 | HAhomoF[N]4-AB-R-I-D-R-I-NH₂ |
| 727 | HAhomoCha[N]4-AB-R-I-D-R-I-NH₂ |

FIG. 4BB

| | |
|---|---|
| 728 | HAhomoNal2[N]4-AB-R-I-D-R-I-NH$_2$ |
| 729 | HAF[N]D-G-R-I-D-R-I-NH$_2$ |
| 730 | HABF[N]D-G-R-I-D-R-I-NH$_2$ |
| 731 | HANal2[N]D-G-R-I-D-R-I-NH$_2$ |
| 732 | HANal1[N]D-G-R-I-D-R-I-NH$_2$ |
| 733 | HACha[N]D-G-R-I-D-R-I-NH$_2$ |
| 734 | HAW[N]D-G-R-I-D-R-I-NH$_2$ |
| 735 | HAhomoF[N]D-G-R-I-D-R-I-NH$_2$ |
| 736 | HAhomoCha[N]D-G-R-I-D-R-I-NH$_2$ |
| 737 | HAhomoNal2[N]D-G-R-I-D-R-I-NH$_2$ |
| 738 | HAF[N][D-Asp]-G-R-I-D-R-I-NH$_2$ |
| 739 | HABF[N][D-Asp]-G-R-I-D-R-I-NH$_2$ |
| 740 | HANal2[N][D-Asp]-G-R-I-D-R-I-NH$_2$ |
| 741 | HANal1[N][D-Asp]-G-R-I-D-R-I-NH$_2$ |
| 742 | HACha[N][D-Asp]-G-R-I-D-R-I-NH$_2$ |
| 743 | HAW[N][D-Asp]-G-R-I-D-R-I-NH$_2$ |
| 744 | HAhomoF[N][D-Asp]-G-R-I-D-R-I-NH$_2$ |
| 745 | HAhomoCha[N][D-Asp]-G-R-I-D-R-I-NH$_2$ |
| 746 | HAhomoNal2[N][D-Asp]-G-R-I-D-R-I-NH$_2$ |
| 747 | HAF[N][γ-L-Glu]-R-I-D-R-I-NH$_2$ |
| 748 | HABF[N][γ-L-Glu]-R-I-D-R-I-NH$_2$ |
| 749 | HANal2[N][γ-L-Glu]-R-I-D-R-I-NH$_2$ |
| 750 | NANal1[N][γ-L-Glu]-R-I-D-R-I-NH$_2$ |
| 751 | HACha[N][γ-L-Glu]-R-I-D-R-I-NH$_2$ |
| 752 | HAW[N][γ-L-Glu]-R-I-D-R-I-NH$_2$ |
| 753 | HAhomoF[N][γ-L-Glu]-R-I-D-R-I-NH$_2$ |
| 754 | HAhomoCha[N][γ-L-Glu]-R-I-D-R-I-NH$_2$ |

| | | |
|---|---|---|
| 755 | HAhomoNal2[N][γ-L-Glu]-R-I-D-R-I-NH₂ | |
| 756 | HAF[N][γ-D-Glu]-R-I-D-R-I-NH₂ | |
| 757 | HABF[N][γ-D-Glu]-R-I-D-R-I-NH₂ | |
| 758 | HANal2[N][γ-D-Glu]-R-I-D-R-I-NH₂ | |
| 759 | HANal1[N][γ-D-Glu]-R-I-D-R-I-NH₂ | |
| 760 | HACha[N][γ-D-Glu]-R-I-D-R-I-NH₂ | |
| 761 | HAW[N][γ-D-Glu]-R-I-D-R-I-NH₂ | |
| 762 | HAhomoF[N][γ-D-Glu]-R-I-D-R-I-NH₂ | |
| 763 | HAhomoCha[N][γ-D-Glu]-R-I-D-R-I-NH₂ | |
| 764 | HAhomoNal2[N][γ-D-Glu]-R-I-D-R-I-NH₂ | |
| 765 | BHAMAL-G-G-R-I-D-R-I-NH₂ | |
| 766 | PBHAMAL-G-G-R-I-D-R-I-NH₂ | |
| 767 | NHAMAL2-G-G-R-I-D-R-I-NH₂ | FIG. 4CC |
| 768 | NHAMAL1-G-G-R-I-D-R-I-NH₂ | |
| 769 | CHAMAL-G-G-R-I-D-R-I-NH₂ | |
| 770 | PHAMAL-G-G-R-I-D-R-I-NH₂ | |
| 771 | NOHAMAL2-G-G-R-I-D-R-I-NH₂ | |
| 772 | IHAMAL-G-G-R-I-D-R-I-NH₂ | |
| 773 | PEHAMAL-G-G-R-I-D-R-I-NH₂ | |
| 774 | CEHAMAL-G-G-R-I-D-R-I-NH₂ | |
| 775 | NEHAMAL-G-G-R-I-D-R-I-NH₂ | |
| 776 | BHAMAL-4-APA-R-I-D-R-I-NH₂ | |
| 777 | PBHAMAL-4-APA-R-I-D-R-I-NH₂ | |
| 778 | NHAMAL2-4-APA-R-I-D-R-I-NH₂ | |
| 779 | NHAMAL1-4-APA-R-I-D-R-I-NH₂ | |
| 780 | CHAMAL-4-APA-R-I-D-R-I-NH₂ | |
| 781 | PHAMAL-4-APA-R-I-D-R-I-NH₂ | |

| | |
|---|---|
| 782 | NOHAMAL2-4-APA-R-I-D-R-I-NH$_2$ |
| 783 | IHAMAL-4-APA-R-I-D-R-I-NH$_2$ |
| 784 | PEHAMAL-4-APA-R-I-D-R-I-NH$_2$ |
| 785 | CEHAMAL-4-APA-R-I-D-R-I-NH$_2$ |
| 786 | NEHAMAL-4-APA-R-I-D-R-I-NH$_2$ |
| 787 | BHAMAL-4-AB-R-I-D-R-I-NH$_2$ |
| 788 | PBHAMAL-4-AB-R-I-D-R-I-NH$_2$ |
| 789 | NHAMAL2-4-AB-R-I-D-R-I-NH$_2$ |
| 790 | NHAMAL1-4-AB-R-I-D-R-I-NH$_2$ |
| 791 | CHAMAL-4-AB-R-I-D-R-I-NH$_2$ |
| 792 | PHAMAL-4-AB-R-I-D-R-I-NH$_2$ |
| 793 | NOHAMAL2-4-AB-R-I-D-R-I-NH$_2$ |
| 794 | IHAMAL-4-AB-R-I-D-R-I-NH$_2$ |
| 795 | PEHAMAL-4-AB-R-I-D-R-I-NH$_2$ |
| 796 | CEHAMAL-4-AB-R-I-D-R-I-NH$_2$ |
| 797 | NEHAMAL-4-AB-R-I-D-R-I-NH$_2$ |
| 798 | BHAMAL-D-G-R-I-D-R-I-NH$_2$ |
| 799 | PBHAMAL-D-G-R-I-D-R-I-NH$_2$ |
| 800 | NHAMAL2-D-G-R-I-D-R-I-NH$_2$ |
| 801 | NHAMAL1-D-G-R-I-D-R-I-NH$_2$ |
| 802 | CHAMAL-D-G-R-I-D-R-I-NH$_2$ |
| 803 | PHAMAL-D-G-R-I-D-R-I-NH$_2$ |
| 804 | NOHAMAL2-D-G-R-I-D-R-I-NH$_2$ |
| 805 | IHAMAL-D-G-R-I-D-R-I-NH$_2$ |
| 806 | PEHAMAL-D-G-R-I-D-R-I-NH$_2$ |
| 807 | CEHAMAL-D-G-R-I-D-R-I-NH$_2$ |
| 808 | NEHAMAL-D-G-R-I-D-R-I-NH$_2$ |

FIG. 4DD

| | |
|---|---|
| 809 | BHAMAL-[D-Asp]-G-R-I-D-R-I-NH$_2$ |
| 810 | PBHAMAL-[D-Asp]-G-R-I-D-R-I-NH$_2$ |
| 811 | NHAMAL2-[D-Asp]-G-R-I-D-R-I-NH$_2$ |
| 812 | NHAMAL1-[D-Asp]-G-R-I-D-R-I-NH$_2$ |
| 813 | CHAMAL-[D-Asp]-G-R-I-D-R-I-NH$_2$ |
| 814 | PHAMAL-[D-Asp]-G-R-I-D-R-I-NH$_2$ |
| 815 | NOHAMAL2-[D-Asp]-G-R-I-D-R-I-NH$_2$ |
| 816 | IHAMAL-[D-Asp]-G-R-I-D-R-I-NH$_2$ |
| 817 | PEHAMAL-[D-Asp]-G-R-I-D-R-I-NH$_2$ |
| 818 | CEHAMAL-[D-Asp]-G-R-I-D-R-I-NH$_2$ |
| 819 | NEHAMAL-[D-Asp]-G-R-I-D-R-I-NH$_2$ |
| 820 | BHAMAL-[γ-L-Glu]-R-I-D-R-I-NH$_2$ |
| 821 | PBHAMAL-[γ-L-Glu]-R-I-D-R-I-NH$_2$ |
| 822 | NHAMAL2-[γ-L-Glu]-R-I-D-R-I-NH$_2$ |
| 823 | NHAMAL1-[γ-L-Glu]-R-I-D-R-I-NH$_2$ |
| 824 | CHAMAL-[γ-L-Glu]-R-I-D-R-I-NH$_2$ |
| 825 | PHAMAL-[γ-L-Glu]-R-I-D-R-I-NH$_2$ |
| 826 | NOHAMAL2-[γ-L-Glu]-R-I-D-R-I-NH$_2$ |
| 827 | IHAMAL-[γ-L-Glu]-R-I-D-R-I-NH$_2$ |
| 828 | PEHAMAL-[γ-L-Glu]-R-I-D-R-I-NH$_2$ |
| 829 | CEHAMAL-[γ-L-Glu]-R-I-D-R-I-NH$_2$ |
| 830 | NEHAMAL-[γ-L-Glu]-R-I-D-R-I-NH$_2$ |
| 831 | BHAMAL-[γ-D-Glu]-R-I-D-R-I-NH$_2$ |
| 832 | PBHAMAL-[γ-D-Glu]-R-I-D-R-I-NH$_2$ |
| 833 | NHAMAL2-[γ-D-Glu]-R-I-D-R-I-NH$_2$ |
| 834 | NHAMAL1-[γ-D-Glu]-R-I-D-R-I-NH$_2$ |
| 835 | CHAMAL-[γ-D-Glu]-R-I-D-R-I-NH$_2$ |

FIG. 4EE

| | | |
|---|---|---|
| 836 | PHAMAL-[γ-D-Glu]-R-I-D-R-I-NH$_2$ | |
| 837 | NOHAMAL2-[γ-D-Glu]-R-I-D-R-I-NH$_2$ | |
| 838 | IHAMAL-[γ-D-Glu]-R-I-D-R-I-NH$_2$ | |
| 839 | PEHAMAL-[γ-D-Glu]-R-I-D-R-I-NH$_2$ | |
| 840 | CEHAMAL-[γ-D-Glu]-R-I-D-R-I-NH$_2$ | |
| 841 | NEHAMAL-[γ-D-Glu]-R-I-D-R-I-NH$_2$ | |
| 842 | BHASUC-G-G-R-I-D-R-I-NH$_2$ | |
| 843 | PBHASUC-G-G-R-I-D-R-I-NH$_2$ | |
| 844 | NHASUC2-G-G-R-I-D-R-I-NH$_2$ | |
| 845 | NHASUC1-G-G-R-I-D-R-I-NH$_2$ | FIG. 4FF |
| 846 | CHASUC-G-G-R-I-D-R-I-NH$_2$ | |
| 847 | PHASUC-G-G-R-I-D-R-I-NH$_2$ | |
| 848 | NOHASUC2-G-G-R-I-D-R-I-NH$_2$ | |
| 849 | IHASUC-G-G-R-I-D-R-I-NH$_2$ | |
| 850 | PEHASUC-G-G-R-I-D-R-I-NH$_2$ | |
| 851 | CEHASUC-G-G-R-I-D-R-I-NH$_2$ | |
| 852 | NEHASUC-G-G-R-I-D-R-I-NH$_2$ | |
| 853 | BHASUC-4-APA-R-I-D-R-I-NH$_2$ | |
| 854 | PBHASUC-4-APA-R-I-D-R-I-NH$_2$ | |
| 855 | NHASUC2-4-APA-R-I-D-R-I-NH$_2$ | |
| 856 | NHASUC1-4-APA-R-I-D-R-I-NH$_2$ | |
| 857 | CHASUC-4-APA-R-I-D-R-I-NH$_2$ | |
| 858 | PHASUC-4-APA-R-I-D-R-I-NH$_2$ | |
| 859 | NOHASUC2-4-APA-R-I-D-R-I-NH$_2$ | |
| 860 | IHASUC-4-APA-R-I-D-R-I-NH$_2$ | |
| 861 | PEHASUC-4-APA-R-I-D-R-I-NH$_2$ | |
| 862 | CEHASUC-4-APA-R-I-D-R-I-NH$_2$ | |

| | |
|---|---|
| 863 | NEHASUC-4-APA-R-I-D-R-I-NH$_2$ |
| 864 | BHASUC-4-AB-R-I-D-R-I-NH$_2$ |
| 865 | PBHASUC-4-AB-R-I-D-R-I-NH$_2$ |
| 866 | NHASUC2-4-AB-R-I-D-R-I-NH$_2$ |
| 867 | NHASUC1-4-AB-R-I-D-R-I-NH$_2$ |
| 868 | CHASUC-4-AB-R-I-D-R-I-NH$_2$ |
| 869 | PHASUC-4-AB-R-I-D-R-I-NH$_2$ |
| 870 | NOHASUC2-4-AB-R-I-D-R-I-NH$_2$ |
| 871 | IHASUC-4-AB-R-I-D-R-I-NH$_2$ |
| 872 | PEHASUC-4-AB-R-I-D-R-I-NH$_2$ |
| 873 | CEHASUC-4-AB-R-I-D-R-I-NH$_2$ |
| 874 | NEHASUC-4-AB-R-I-D-R-I-NH$_2$ |
| 875 | BHASUC-D-G-R-I-D-R-I-NH$_2$ |
| 876 | PBHASUC-D-G-R-I-D-R-I-NH$_2$ |
| 877 | NHASUC2-D-G-R-I-D-R-I-NH$_2$ |
| 878 | NHASUC1-D-G-R-I-D-R-I-NH$_2$ |
| 879 | CHASUC-D-G-R-I-D-R-I-NH$_2$ |
| 880 | PHASUC-D-G-R-I-D-R-I-NH$_2$ |
| 881 | NOHASUC2-D-G-R-I-D-R-I-NH$_2$ |
| 882 | IHASUC-D-G-R-I-D-R-I-NH$_2$ |
| 883 | PEHASUC-D-G-R-I-D-R-I-NH$_2$ |
| 884 | CEHASUC-D-G-R-I-D-R-I-NH$_2$ |
| 885 | NEHASUC-D-G-R-I-D-R-I-NH$_2$ |
| 886 | BHASUC-[D-Asp]-G-R-I-D-R-I-NH$_2$ |
| 887 | PBHASUC-[D-Asp]-G-R-I-D-R-I-NH$_2$ |
| 888 | NHASUC2-[D-Asp]-G-R-I-D-R-I-NH$_2$ |
| 889 | NHASUC1-[D-Asp]-G-R-I-D-R-I-NH$_2$ |

FIG. 4GG

| | |
|---|---|
| 890 | CHASUC-[D-Asp]-G-R-I-D-R-I-NH$_2$ |
| 891 | PHASUC-[D-Asp]-G-R-I-D-R-I-NH$_2$ |
| 892 | NOHASUC2-[D-Asp]-G-R-I-D-R-I-NH$_2$ |
| 893 | IHASUC-[D-Asp]-G-R-I-D-R-I-NH$_2$ |
| 894 | PEHASUC-[D-Asp]-G-R-I-D-R-I-NH$_2$ |
| 895 | CEHASUC-[D-Asp]-G-R-I-D-R-I-NH$_2$ |
| 896 | NEHASUC-[D-Asp]-G-R-I-D-R-I-NH$_2$ |
| 897 | BHASUC-[γ-L-Glu]-R-I-D-R-I-NH$_2$ |
| 898 | PBHASUC-[γ-L-Glu]-R-I-D-R-I-NH$_2$ |
| 899 | NHASUC2-[γ-L-Glu]-R-I-D-R-I-NH$_2$ |
| 900 | NHASUC1-[γ-L-Glu]-R-I-D-R-I-NH$_2$ |
| 901 | CHASUC-[γ-L-Glu]-R-I-D-R-I-NH$_2$ |
| 902 | PHASUC-[γ-L-Glu]-R-I-D-R-I-NH$_2$ |
| 903 | NOHASUC2-[γ-L-Glu]-R-I-D-R-I-NH$_2$ |
| 904 | IHASUC-[γ-L-Glu]-R-I-D-R-I-NH$_2$ |
| 905 | PEHASUC-[γ-L-Glu]-R-I-D-R-I-NH$_2$ |
| 906 | CEHASUC-[γ-L-Glu]-R-I-D-R-I-NH$_2$ |
| 907 | NEHASUC-[γ-L-Glu]-R-I-D-R-I-NH$_2$ |
| 908 | BHASUC-[γ-D-Glu]-R-I-D-R-I-NH$_2$ |
| 909 | PBHASUC-[γ-D-Glu]-R-I-D-R I-NH$_2$ |
| 910 | NHASUC2-[γ-D-Glu]-R-I-D-R-I-NH$_2$ |
| 911 | NHASUC1-[γ-D-Glu]-R-I-D-R-I-NH$_2$ |
| 912 | CHASUC-[γ-D-Glu]-R-I-D-R-I-NH$_2$ |
| 913 | PHASUC-[γ-D-Glu]-R-I-D-R-I-NH$_2$ |
| 914 | NOHASUC2-[γ-D-Glu]-R-I-D-R-I-NH$_2$ |
| 915 | IHASUC-[γ-D-Glu]-R-I-D-R-I-NH$_2$ |
| 916 | PEHASUC-[γ-D-Glu]-R-I-D-R-I-NH$_2$ |

917 CEHASUC-[γ-D-Glu]-R-I-D-R-I-NH$_2$

918 NEHASUC-[γ-D-Glu]-R-I-D-R-I-NH$_2$

919 Phosphoryl-F-G-G-R-I-D-R-I-NH$_2$

920 Phosphoryl-BF-G-G-R-I-D-R-I-NH$_2$

921 Phosphoryl-Nal2-G-G-R-I-D-R-I-NH$_2$

922 Phosphoryl-Nal1-G-G-R-I-D-R-I-NH$_2$

923 Phosphoryl-Cha-G-G-R-I-D-R-I-NH$_2$

924 Phosphoryl-W-G-G-R-I-D-R-I-NH$_2$

925 Phosphoryl-homoF-G-G-R-I-D-R-I-NH$_2$

926 Phosphoryl-homoCha-G-G-R-I-D-R-I-NH$_2$

927 Phosphoryl-homoNal2-G-G-R-I-D-R-I-NH$_2$

928 Phosphoryl-F-4-APA-R-I-D-R-I-NH$_2$

929 Phosphoryl-BF-4-APA-R-I-D-R-I-NH$_2$

930 Phosphoryl-Nal2-4-APA-R-I-D-R-I-NH$_2$

931 Phosphoryl-Nal1-4-APA-R-I-D-R-I-NH$_2$

932 Phosphoryl-Cha-4-APA-R-I-D-R-I-NH$_2$

933 Phosphoryl-W-4-APA-R-I-D-R-I-NH$_2$

934 Phosphoryl-homoF-4-APA-R-I-D-R-I-NH$_2$

935 Phosphoryl-homoCha-4-APA-R-I-D-R-I-NH$_2$

936 Phosphoryl-homoNal2-4-APA-R-I-D-R-I-NH$_2$

937 Phosphoryl-F-4-AB-R-I-D-R-I-NH$_2$

938 Phosphoryl-BF-4-AB-R-I-D-R-I-NH$_2$

939 Phosphoryl-Nal2-4-AB-R-I-D-R-I-NH$_2$

940 Phosphoryl-Nal2-4-AB-R-I-D-R-I-NH$_2$

941 Phosphoryl-Cha-4-AB-R-I-D-R-I-NH$_2$

942 Phosphoryl-W-4-AB-R-I-D-R-I-NH$_2$

943 Phosphoryl-homoF-4-AB-R-I-D-R-I-NH$_2$

| | |
|---|---|
| 944 | Phosphoryl-homoCha-4-AB-R-I-D-R-I-NH$_2$ |
| 945 | Phosphoryl-homoNal2-4-AB-R-I-D-R-I-NH$_2$ |
| 946 | Phosphoryl-F-D-G-R-I-D-R-I-NH$_2$ |
| 947 | Phosphoryl-BF-D-G-R-I-D-R-I-NH$_2$ |
| 948 | Phosphoryl-Nal2-D-G-R-I-D-R-I-NH$_2$ |
| 949 | Phosphoryl-Nal1-D-G-R-I-D-R-I-NH$_2$ |
| 950 | Phosphoryl-Cha-D-G-R-I-D-R-I-NH$_2$ |
| 951 | Phosphoryl-W-D-G-R-I-D-R-I-NH$_2$ |
| 952 | Phosphoryl-homoF-D-G-R-I-D-R-I-NH$_2$ |
| 953 | Phosphoryl-homoCha-D-G-R-I-D-R-I-NH$_2$ |
| 954 | Phosphoryl-homoNal2-D-G-R-I-D-R-I-NH$_2$ |
| 955 | Phosphoryl-F-[D-Asp]-G-R-I-D-R-I-NH$_2$ |
| 956 | Phosphoryl-BF-[D-Asp]-G-R-I-D-R-I-NH$_2$ |
| 957 | Phosphoryl-Nal2-[D-Asp]-G-R-I-D-R-I-NH$_2$ |
| 958 | Phosphoryl-Nal1-[D-Asp]-G-R-I-D-R-I-NH$_2$ |
| 959 | Phosphoryl-Cha-[D-Asp]-G-R-I-D-R-I-NH$_2$ |
| 960 | Phosphoryl-W-[D-Asp]-G-R-I-D-R-I-NH$_2$ |
| 961 | Phosphoryl-homoF-[D-Asp]-G-R-I-D-R-I-NH$_2$ |
| 962 | Phosphoryl-homoCha-[D-Asp]-G-R-I-D-R-I-NH$_2$ |
| 963 | Phosphoryl-homoNal2-[D-Asp]-G-R-I-D-R-I-NH$_2$ |
| 964 | Phosphoryl-F-[γ-L-Glu]-R-I-D-R-I-NH$_2$ |
| 965 | Phosphoryl-BF-[γ-L-Glu]-R-I-D-R-I-NH$_2$ |
| 966 | Phosphoryl-Nal2-[γ-L-Glu]-R-I-D-R-I-NH$_2$ |
| 967 | Phosphoryl-Nal1-[γ-L-Glu]-R-I-D-R-I-NH$_2$ |
| 968 | Phosphoryl-Cha-[γ-L-Glu]-R-I-D-R-I-NH$_2$ |
| 969 | Phosphoryl-W-[γ-L-Glu]-R-I-D-R-I-NH$_2$ |
| 970 | Phosphoryl-homoF-[γ-L-Glu]-R-I-D-R-I-NH$_2$ |

FIG. 4JJ

| | |
|---|---|
| 971 | Phosphoryl-homoCha-[γ-L-Glu]-R-I-D-R-I-NH$_2$ |
| 972 | Phosphoryl-homoNal2-[γ-L-Glu]-R-I-D-R-I-NH$_2$ |
| 973 | Phosphoryl-F-[γ-D-Glu]-R-I-D-R-I-NH$_2$ |
| 974 | Phosphoryl-BF-[γ-D-Glu]-R-I-D-R-I-NH$_2$ |
| 975 | Phosphoryl-Nal2-[γ-D-Glu]-R-I-D-R-I-NH$_2$ |
| 976 | Phosphoryl-Nal1-[γ-D-Glu]-R-I-D-R-I-NH$_2$ |
| 977 | Phosphoryl-Cha-[γ-D-Glu]-R-I-D-R-I-NH$_2$ |
| 978 | Phosphoryl-W-[γ-D-Glu]-R-I-D-R-I-NH$_2$ |
| 979 | Phosphoryl-homoF-[γ-D-Glu]-R-I-D-R-I-NH$_2$ |
| 980 | Phosphoryl-homoCha-[γ-D-Glu]-R-I-D-R-I-NH$_2$ |
| 981 | Phosphoryl-homoNal2-[γ-D-Glu]-R-I-D-R-I-NH$_2$ |
| 982 | BSUC-G-G-R-I-D-R-I-NH$_2$ |
| 983 | PBSUC-G-G-R-I-D-R-I-NH$_2$ |
| 984 | NSUC2-G-G-R-I-D-R-I-NH$_2$ |
| 985 | NSUC1-G-G-R-I-D-R-I-NH$_2$ |
| 986 | CSUC-G-G-R-I-D-R-I-NH$_2$ |
| 987 | PSUC-G-G-R-I-D-R-I-NH$_2$ |
| 988 | ISUC-G-G-R-I-D-R-I-NH$_2$ |
| 989 | PESUC-G-G-R-I-D-R-I-NH$_2$ |
| 990 | NESUC-G-G-R-I-D-R-I-NH$_2$ |
| 991 | BSUC-4-APA-R-I-D-R-I-NH$_2$ |
| 992 | PBSUC-4-APA-R-I-D-R-I-NH$_2$ |
| 993 | NSUC2-4-APA-R-I-D-R-I-NH$_2$ |
| 994 | NSUC1-4-APA-R-I-D-R-I-NH$_2$ |
| 995 | CSUC-4-APA-R-I-D-R-I-NH$_2$ |
| 996 | PSUC-4-APA-R-I-D-R-I-NH$_2$ |
| 997 | NOSUC2-4-APA-R-I-D-R-I-NH$_2$ |

FIG. 4KK

| | |
|---|---|
| 998 | ISUC-4-APA-R-I-D-R-I-NH$_2$ |
| 999 | PESUC-4-APA-R-I-D-R-I-NH$_2$ |
| 1000 | CESUC-4-APA-R-I-D-R-I-NH$_2$ |
| 1001 | NESUC-4-APA-R-I-D-R-I-NH$_2$ |
| 1002 | BSUC-4-AB-R-I-D-R-I-NH$_2$ |
| 1003 | PBSUC-4-AB-R-I-D-R-I-NH$_2$ |
| 1004 | NSUC2-4-AB-R-I-D-R-I-NH$_2$ |
| 1005 | NSUC1-4-AB-R-I-D-R-I-NH$_2$ |
| 1006 | CSUC-4-AB-R-I-D-R-I-NH$_2$ |
| 1007 | PSUC-4-AB-R-I-D-R-I-NH$_2$ |
| 1008 | NOSUC2-4-AB-R-I-D-R-I-NH$_2$ |
| 1009 | ISUC-4-AB-R-I-D-R-I-NH$_2$ |
| 1010 | PESUC-4-AB-R-I-D-R-I-NH$_2$ |
| 1011 | CESUC-4-AB-R-I-D-R-I-NH$_2$ |
| 1012 | NESUC-4-AB-R-I-D-R-I-NH$_2$ |
| 1013 | BSUC-D-G-R-I-D-R-I-NH$_2$ |
| 1014 | PBSUC-D-G-R-I-D-R-I-NH$_2$ |
| 1015 | NSUC2-D-G-R-I-D-R-I-NH$_2$ |
| 1016 | NSUC1-D-G-R-I-D-R-I-NH$_2$ |
| 1017 | CSUC-D-G-R-I-D-R-I-NH$_2$ |
| 1018 | PSUC-D-G-R-I-D-R-I-NH$_2$ |
| 1019 | NOSUC2-D-G-R-I-D-R-I-NH$_2$ |
| 1020 | ISUC-D-G-R-I-D-R-I-NH$_2$ |
| 1021 | PESUC-D-G-R-I-D-R-I-NH$_2$ |
| 1022 | CESUC-D-G-R-I-D-R-I-NH$_2$ |
| 1023 | NESUC-D-G-R-I-D-R-I-NH$_2$ |
| 1024 | BSUC-[D-Asp]-G-R-I-D-R-I-NH$_2$ |

FIG. 4LL

| | |
|---|---|
| 1025 | PBSUC-[D-Asp]-G-R-I-D-R-I-NH$_2$ |
| 1026 | NSUC2-[D-Asp]-G-R-I-D-R-I-NH$_2$ |
| 1027 | NSUC1-[D-Asp]-G-R-I-D-R-I-NH$_2$ |
| 1028 | CSUC-[D-Asp]-G-R-I-D-R-I-NH$_2$ |
| 1029 | PSUC-[D-Asp]-G-R-I-D-R-I-NH$_2$ |
| 1030 | NOSUC2-[D-Asp]-G-R-I-D-R-I-NH$_2$ |
| 1031 | ISUC-[D-Asp]-G-R-I-D-R-I-NH$_2$ |
| 1032 | PESUC-[D-Asp]-G-R-I-D-R-I-NH$_2$ |
| 1033 | CESUC-[D-Asp]-G-R-I-D-R-I-NH$_2$ |
| 1034 | NESUC-[D-Asp]-G-R-I-D-R-I-NH$_2$ |
| 1035 | BSUC-[γ-L-Glu]-R-I-D-R-I-NH$_2$ |
| 1036 | PBSUC-[γ-L-Glu]-R-I-D-R-I-NH$_2$ |
| 1037 | NSUC2-[γ-L-Glu]-R-I-D-R-I-NH$_2$ |
| 1038 | NSUC1-[γ-L-Glu]-R-I-D-R-I-NH$_2$ |
| 1039 | CSUC-[γ-L-Glu]-R-I-D-R-I-NH$_2$ |
| 1040 | PSUC-[γ-L-Glu]-R-I-D-R-I-NH$_2$ |
| 1041 | NOSUC2-[γ-L-Glu]-R-I-D-R-I-NH$_2$ |
| 1042 | ISUC-[γ-L-Glu]-R-I-D-R-I-NH$_2$ |
| 1043 | PESUC-[γ-L-Glu]-R-I-D-R-I-NH$_2$ |
| 1044 | CESUC-[γ-L-Glu]-R-I-D-R-I-NH$_2$ |
| 1045 | NESUC-[γ-L-Glu]-R-I-D-R-I-NH$_2$ |
| 1046 | BSUC-[γ-D-Glu]-R-I-D-R-I-NH$_2$ |
| 1047 | PBSUC-[γ-D-Glu]-R-I-D-R-I-NH$_2$ |
| 1048 | NSUC2-[γ-D-Glu]-R-I-D-R-I-NH$_2$ |
| 1049 | NSUC1-[γ-D-Glu]-R-I-D-R-I-NH$_2$ |
| 1050 | CSUC-[γ-D-Glu]-R-I-D-R-I-NH$_2$ |
| 1051 | PSUC-[γ-D-Glu]-R-I-D-R-I-NH$_2$ |

1052  NOSUC2-[γ-D-Glu]-R-I-D-R-I-NH$_2$

1053  ISUC-[γ-D-Glu]-R-I-D-R-I-NH$_2$

1054  PESUC-[γ-D-Glu]-R-I-D-R-I-NH$_2$

1055  CESUC-[γ-D-Glu]-R-I-D-R-I-NH$_2$

1056  NESUC-[γ-D-Glu]-R-I-D-R-I-NH$_2$

ATRIAL NATRIURETIC PEPTIDE CLEARANCE INHIBITORS WHICH RESIST DEGRADATION

This application is a continuation of application Ser. No. 07/644,876 filed Jan. 23, 1991 and now abandoned which is a continuation of application Ser. No. 07/286,640, filed Dec. 15, 1988, and now abandoned, which is a continuation-in-part of U.S. Ser. No. 233,650, filed Aug. 18, 1988 now abandoned.

TECHNICAL FIELD

The invention relates to synthetic peptides which are useful as diuretics, natriuretics, and/or vasodilators in animal subjects. More particularly, the invention concerns peptides which block specific clearance receptors for atrial natriuretic peptides and which also inhibit peptidases for which atrial natriuretic peptides are substrates.

BACKGROUND ART

Atrial natriuretic peptides (ANP) are circulating hormones which are synthesized in the atrium of the heart and secreted. The hormones regulate blood pressure through their natriuretic, diuretic and vasorelaxant activities, as well as inhibition of aldosterone secretion from the adrenal gland, inhibition of renin secretion from the kidney, and functional antagonism of the renin-angiotensin system. The ANP hormones have been widely studied, and a large number of analogs have been proposed. Copending U.S. application Ser. Nos. 138,893, filed Dec. 24, 1987 and 237,299, filed Aug. 26, 1988, assigned to the same assignee and incorporated herein by reference disclose a series of linear analogs of the native ANP, which native ANPs are cyclic disulfides. Cyclic analogs are disclosed in copending application Ser. No. 174,739, filed May 31, 1988, assigned to the same assignee and also incorporated herein by reference. These copending applications are the latest filed in a series which includes U.S. Ser. No. 168,661, filed Mar. 16, 1988 (allowed), U.S. Ser. No. 921,360 (abandoned), U.S. Ser. No. 904,091 (abandoned), U.S. Ser. No. 868,312 now issued as U.S. Pat. No. 4,757,048, and U.S. Ser. No. 795,220 (abandoned). Various analogs have also been proposed by others, and the literature relating to ANP analogs is now quite extensive.

It is known that the half life of ANPs in the blood stream is relatively short and that many of the analogs of ANP, such as those set forth in the above-referenced U.S. Ser. No. 138,893, appear to act by blocking the clearance receptors for ANP, thus increasing the opportunity for the natively produced ANPs to exert their effects. Two distinct pathways have now been identified which appear to contribute to most ANP clearance. The first pathway relates to receptor mediated metabolic clearance which has sufficient affinity and capacity to account for 70–80% of total ANP clearance from the system (Maack, T., et al, *Science* (1987) 238:675–679, EPO Publication No. 223,143). It was further determined that an additional, nonsaturatable clearance pathway also operates if the specific receptor pathway is inhibited, Almeida, F. A., *Amer J Physiol* (1988) (submitted).

On the basis of additional evidence from a variety of sources, it is believed that the nonsaturatable clearance pathway may involve the activity of a peptidase, neutral endopeptidase 24.11 (EC3.4.24.11), commonly referred to as endopeptidase 24.11. U.S. Pat. No. 4,740,499, issued Apr. 26, 1988, describes and claims a method of prolonging or enhancing the bioactivity of an atrial peptide using two specific inhibitors of endopeptidase 24.11, thiorphan or kelatorphan. These inhibitors are administered simultaneously with the atrial peptide. EPO Application Publication No. 254,032, published Jan. 27, 1988, also describes and claims the use of inhibitors of endopeptidase 24.11, or of neutral metallopeptidases in general, to treat hypertension, either alone or in association with ANP (or with an angiotensin converting enzyme inhibitor). In this disclosure, the inhibitors of the neutral metalloendopeptidase include thiorphan but further include compounds disclosed in U.S. Pat. No. 4,610,816, i.e., a substantial class of compounds, and compounds disclosed in EPO Application Publication No. 117,429 which also includes a substantial class. Reference is also made to compounds disclosed in U.S. Ser. No. 32,153, filed Mar. 27, 1987, U.S. Pat. No. 4,513,009 and European Application 38,046. In addition, a large volume of literature supports the conclusion that endopeptidase 24.11 is responsible for the extracellular inactivation of ANP (Stevenson, S. L., et al, *Biochem J* (1987) 243:183–187; Olins, G. M., et al, *Biochim Biophys Acta* (1987) 901:97–100; Koehn, J. A., et al, *J Biol Chem* (1987) 262:11623–11627); including the observation that a metabolic fragment of ANP isolated from human plasma is identical to the primary cleavage product of ANP treated with endopeptidase 24.11 (Yandle, T., et al, *Biochem Biophys Res Commun* (1987) 146:832–839).

It has also been observed by others that inhibitors of endopeptidase 24.11 potentiate the biological responses of administered ANP (Fennell, S. A., et al, *FASEB J* (1988) 2:A936; Seymour, A. A., et al, *ibid;* Trapani, A. J., et al, *ibid;* McMartin, C., et al, *ibid;* Zimmerman, M. B., et al, *ibid*:A937).

In addition to the use of thiorphan, there has been disclosed a variety of strategies for the inhibition of endopeptidase 24.11. These strategies include the use of a metal binding substituent appropriately spaced from an aromatic moiety. Roques, B. P., et al, *Nature* (1980) 288:286–288; Gordon, E. M., et al, *Life Sci* (1983) 33(Supplement 1):113–116; Mumford, R. M., et al, *Biochem Biophys Res Comm* (1982) 109:1303–1309; Fournie-Zaluski, M. C., et al, *J Med Chem* (1983) 26:60–65; Waksman, G., et al, *Biochem Biophys Res Comm* (1985) 131:262–268.

Blockage of both the specific receptor and the nonsaturatable endopeptidase 24.11 based clearance mechanisms by suitable inhibitors should greatly enhance the circulating levels of ANP and prolong the activity of the endogenous hormones. Indeed, it has been shown that conscious rats treated with an ANP clearance receptor-specific ligand in combination with the endopeptidase 24.11 inhibitor thiorphan results in greater diuresis and natriuresis than blockade of either pathway alone (Koepke, J., et al, *FASEB Jour* (1988) 2:A527. However, administration of inhibitors of these pathways separately carries the disadvantage that cerebral endopeptidase 24.11 will also be inhibited since thiorphan is capable of crossing the blood-brain barrier (Bourgoin, S., et al, *J Pharm Exp Ther* (1986) 238:360–366). This disadvantage could be overcome by utilization of a single agent which would block the clearance receptors for ANP, as well as inhibiting the alternate nonsaturatable enzymatic pathway.

The compounds of the invention described herein incorporate endopeptidase 24.11 inhibition functionality (or functionality which inhibits cleavage at Cys105-Phe106 of ANP) into analogs which also bind the ANP clearance receptors. Surprisingly, the elements which result in cleavage inhibition do not interfere with the clearance receptor binding capability of these compounds.

DISCLOSURE OF THE INVENTION

The invention provides compounds which enhance the ability of endogenously secreted ANP hormones to regulate the homeostatic mechanisms which provide protection against high blood pressure and fluid and sodium retention. Accordingly, the compounds of the invention are useful for the treatment of hypertension, heart disease, renal failure and edema by virtue of their natriuretic, diuretic, and vasorelaxant activities.

Most of the synthetic analog compounds of the present invention retain a core pentapeptide sequence of amino acid residues which correspond in a defined way to the sequence $AA_{109}$-$AA_{113}$ of native ANPs, using the numbering system recommended by Dzau, V. J., et al, *N Engl J Med* (1987) 316:1279 for ANP peptides based on the 126-residue proANP peptide. In the known native ANPs, this core sequence is RIDRI in rat and RMDRI in human. While some defined permutations of this sequence, including some wherein $AA_{113}$ is not present, retain activity, most are not active in in vitro model systems for assay of diuretic or natriuretic activities; these analogs empower the function of endogenous ANPs by blocking clearance receptor(s) for these peptides.

In one aspect the invention is directed to compounds of the formula:

wherein:
each of $AA_{109}$ and $AA_{112}$ is, independently, preferably a basic/noncyclic, but can be also a neutral/polar/large/nonaromatic amino acid residue; in addition, $AA_{109}$ can be a neutral/nonpolar/large/nonaromatic amino acid;

$AA_{110}$ is a neutral/nonpolar/large/nonaromatic amino acid residue in the D or L configuration;

$AA_{111}$ is an acidic amino acid residue; and $AA_{113}$ is a neutral/nonpolar/large/nonaromatic amino acid residue, in the D or L configuration or is a covalent bond;

wherein $Z_1$ is

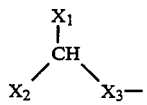

wherein
$X_1$ is a hydrophobic cyclic or noncyclic residue of 4–14C, $X_2$ is a substituent containing a metal-coordinating atom within 1.5–7 angstroms (2–4 single covalent bonds) of the illustrated —CH—, said metal-coordinating atom selected from S and O; and —$X_3$— is a bond, —$CH_2$—, —CO—, or —NH—;

$Z_2$ is a spacer group which provides a spaced dimension of about 4.5–15 angstroms, i.e., contains 3–9 atoms in a linked group or can be conformed to the proper spacing by folding; and $Z_3$ is (OH), $NH_2$, NHR" or NR"R''' wherein R" or R''' are each independently straight or branched chain alkyl of 1–10 carbon atoms wherein 1 or 2 carbons may be replaced by O, N, or S, or $Z_3$ is a peptide residue of 1–20 amino acid residues, or an amide or alkyl amide thereof, with the proviso that when $AA_{113}$ is a covalent bond, $Z_3$ cannot be OH, $NH_2$ or a peptide.

In the foregoing compounds of the invention, one or more of the amide backbone linkages between any adjacent amino acid residues may optionally be replaced by a linkage selected from the group consisting of —$CH_2NH$—, —$CH_2$—S—, —$CH_2CH_2$—, —CH=CH— (cis and trans), —$COCH_2$—, —$CH(OH)CH_2$ and —$CH_2SO$—.

One or two of the residues in the peptides of the invention may be replaced by the corresponding D isomer, in addition to, or instead of, $AA_{110}$ and $AA_{113}$.

Also provided in accordance with aspects of the invention are pharmaceutical compositions useful as natriuretics, diuretics, vasodilators and/or modulators of the renin-angiotensin-aldosterone system, which compositions contain at least one compound of the invention, including the amides and esters and the nontoxic salts thereof, together with a pharmaceutically acceptable liquid, gel or solid carrier.

Additional aspects of the present invention provide methods for producing such compounds and compositions, and methods for using the compounds and compositions as therapeutic agents.

BRIEF DESCRIPTION OF THE DRAWINGS

FIGS. 2(A-Y) shows exemplary embodiments of some preferred $Z_1$ substituents, along with the abbreviations for them.

FIG. 3 shows additional abbreviations for certain embodiments of Z

FIGS. 4(A-NN) shows exemplary embodiments of the compounds of the invention.

In FIG. 5A the values are for average NA-excretion for 1 and N=7. In FIG. 5B the values are for average NA-excretion for 1 and N=7. In FIG. 5C the values are for average volume flow for 1 and N=7. In FIG. 5D the values are for average volume flow for 1 and N=7.

MODES OF CARRYING OUT THE INVENTION

The class of compounds is capable of exhibiting or modulating the natriuretic, diuretic and/or vasorelaxant activity of the native peptides in mammals in vivo by virtue of the ability to impair the clearance of endogenous ANP both by inhibition of the specific receptor clearance system and by inhibition of endopeptidase 24.11 activity.

The sequence of amino acid residues of the core pentapeptide, and preferred embodiments thereof, is defined in terms of amino acids of certain characteristics of particular subclasses.

Figure 1:
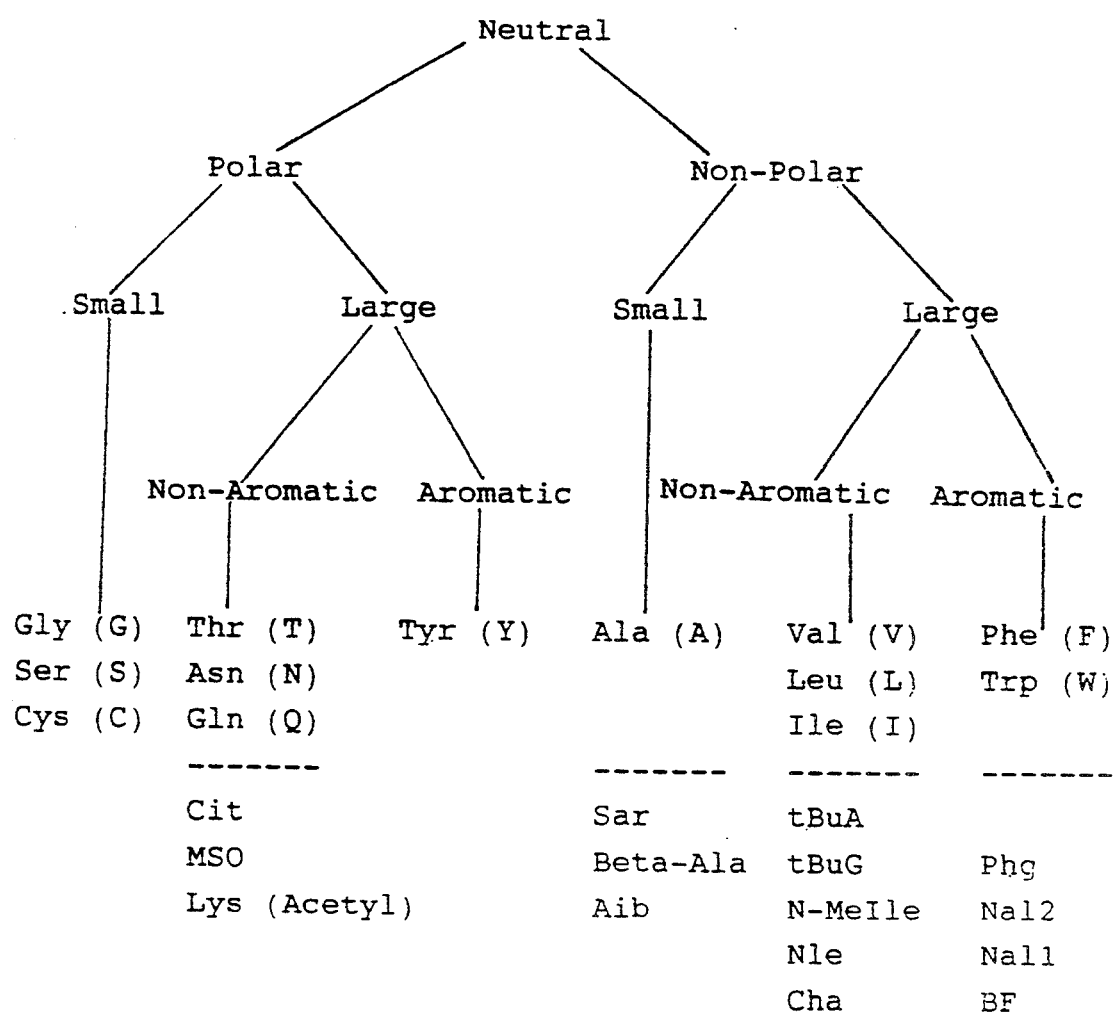
FIG. 1 shows the classification of amino acids as they define the compounds of the invention.
Figure 5A:
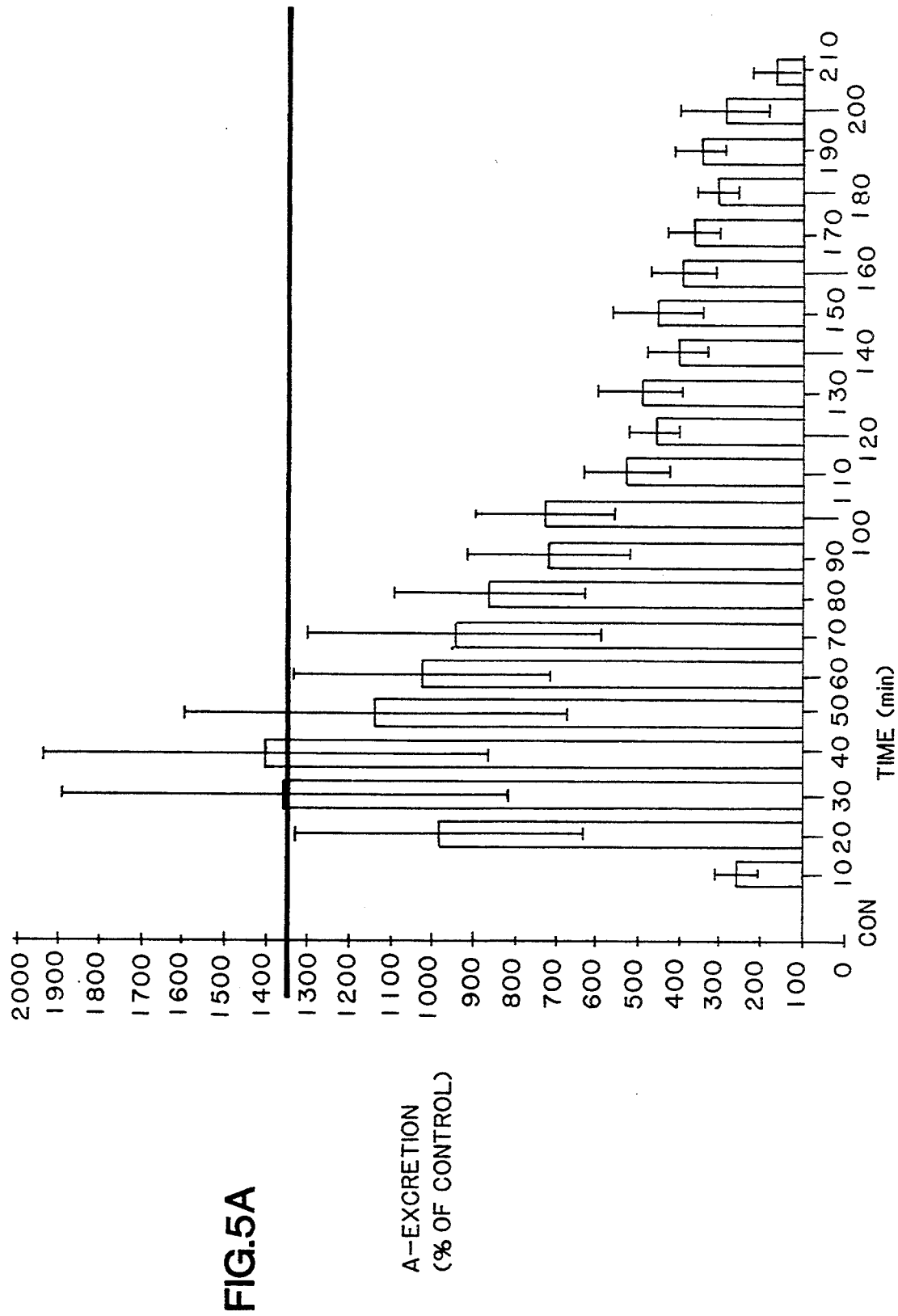
FIGS. 5A–5D show the effect of a compound of the invention on diuresis and natriuresis in whole animals.
Figure 5B:
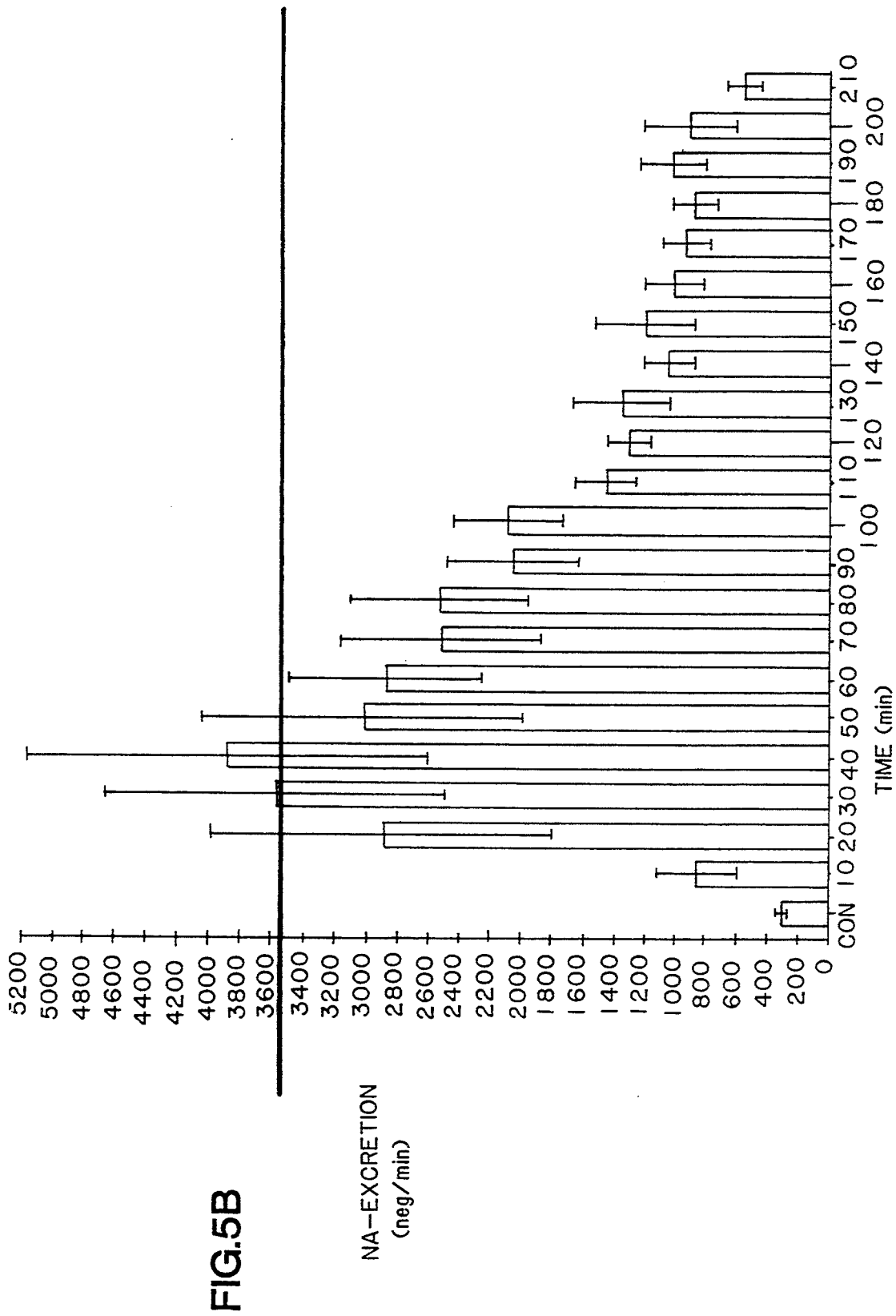
Figure 5C:
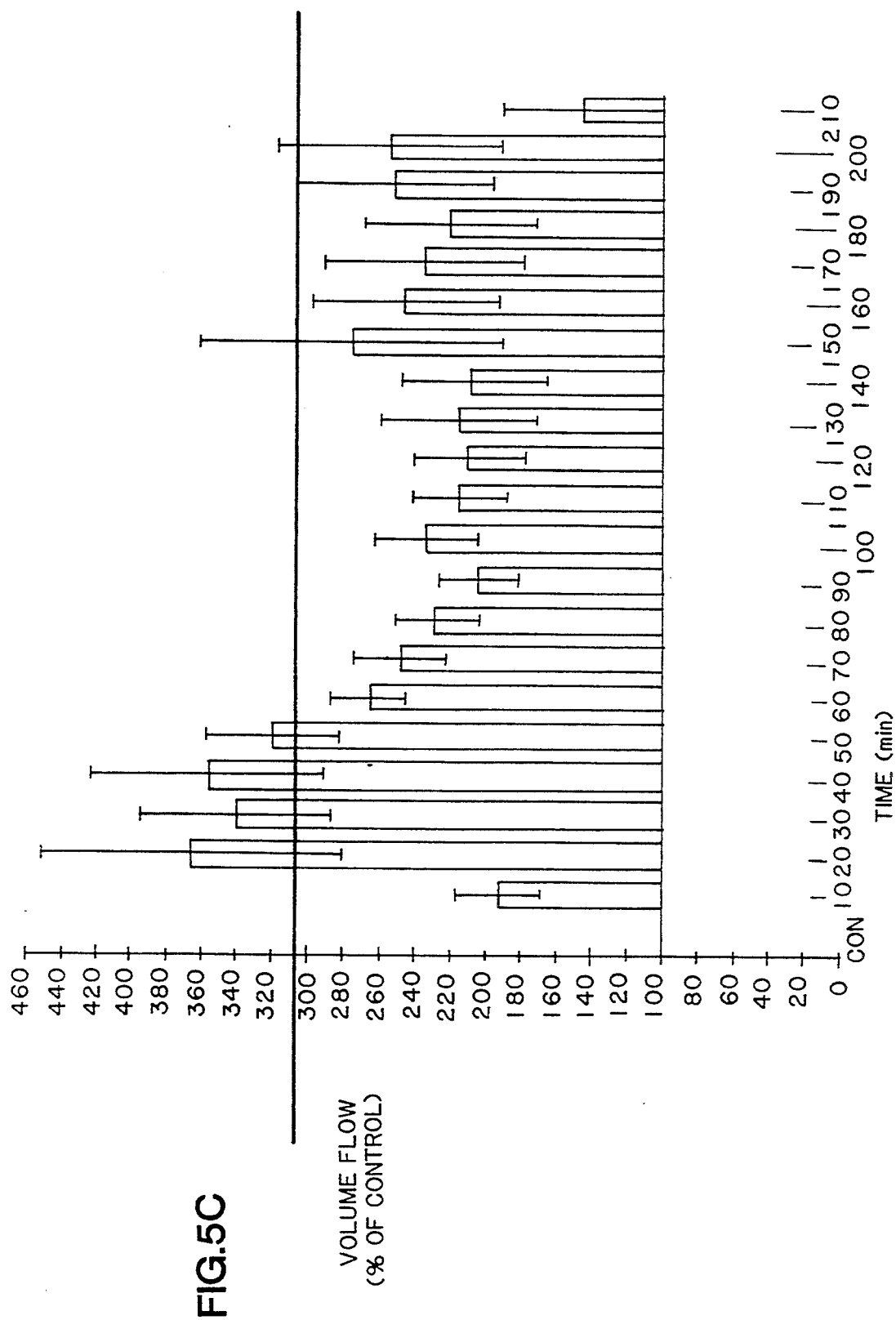
Figure 5D:
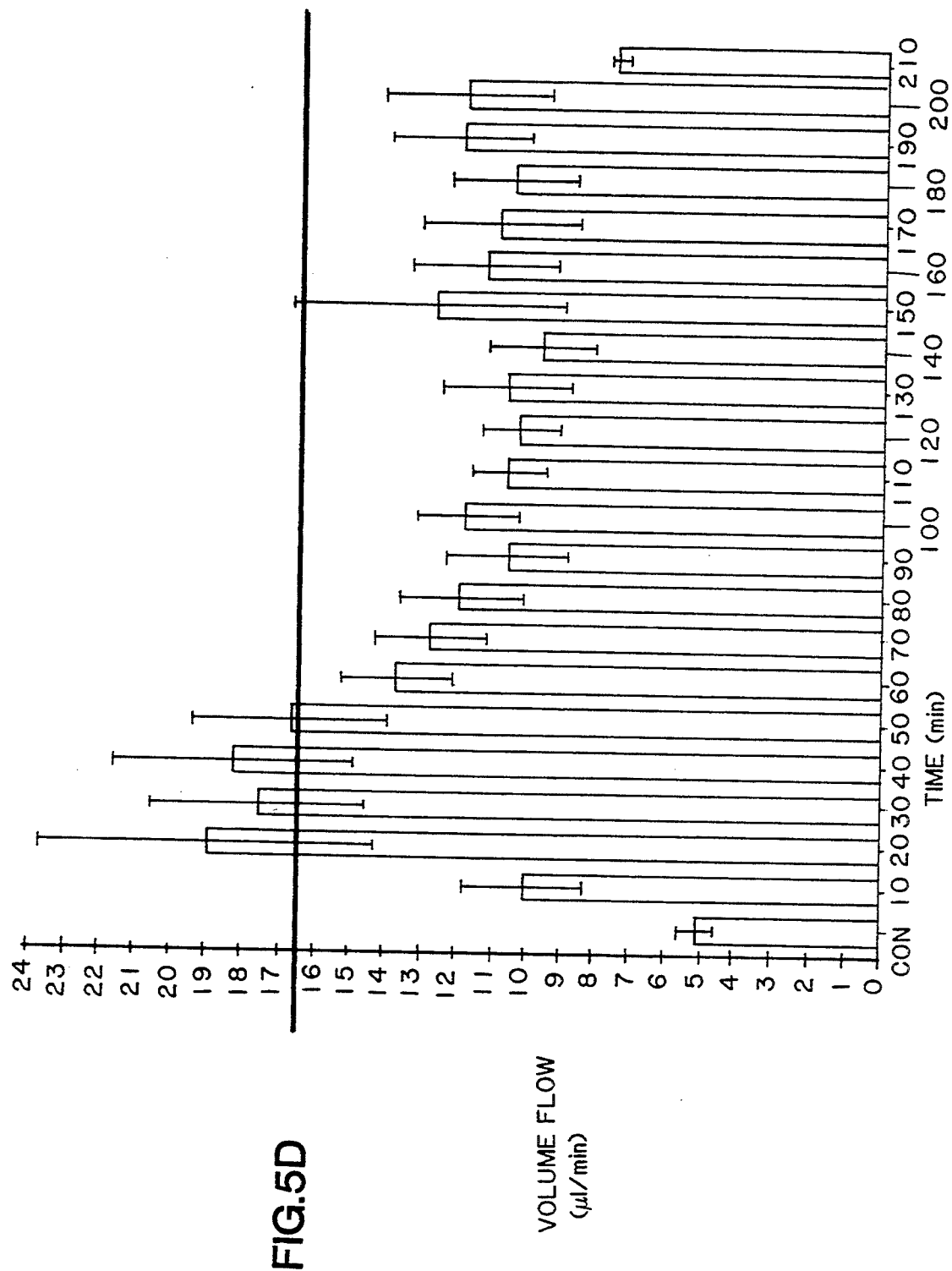

Amino acid residues can be generally subclassified into four major subclasses as follows and as shown in FIG. 1.

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged", a significant percentage (at least approximately 25%) of the individual molecules are charged at physiological pH. The degree of attraction or repulsion required for classification as polar or nonpolar is arbitrary, and, therefore, amino acids specifically contemplated by the invention have been specifically classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of carbon atoms or less, inclusive of the carboxyl carbon. Small residues are, of course, always nonaromatic.

For the naturally occurring protein amino acids, subclassification according to the foregoing scheme is as follows (see also FIG. 1)

Acidic: Aspartic acid and Glutamic acid;
Basic/noncyclic: Arginine, Lysine;
Basic/cyclic: Histidine;
Neutral/polar/small: Glycine, Serine and Cysteine;
Neutral/polar/large/nonaromatic: Threonine, Asparagine, Glutamine;
Neutral/polar/large/aromatic: Tyrosine;
Neutral/nonpolar/small: Alanine;
Neutral/nonpolar/large/nonaromatic: Valine, Isoleucine, Leucine, Methionine;
Neutral/nonpolar/large/aromatic: Phenylalanine, and Tryptophan.

The gene-encoded amino acid proline, although technically within the group neutral/nonpolar/large/cyclic and nonaromatic, is a special case due to its known effects on the secondary conformation of peptide chains, and is not, therefore, included in this defined group.

Certain commonly encountered amino acids, which are not encoded by the genetic code, include, for example, beta-alanine (beta-Ala), or other omega-amino acids, such as 3-amino propionic, 4-amino butyric and so forth, alpha-aminoisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) and methionine sulfoxide (MSO). These also fall conveniently into particular categories.

Based on the above definition,
Sar and beta-Ala are neutral/nonpolar/small;
t-BuA, t-BuG, N-MeIle, Nle and Cha are neutral/nonpolar/large/nonaromatic;
Orn is basic/noncyclic;
Cya is acidic;
Cit, MSO and (acetyl) Lys are neutral/polar/large/nonaromatic; and
Phg is neutral/nonpolar/large/aromatic.

See, also, FIG. 1.

The various omega-amino acids are classified according to size as neutral/nonpolar/small (beta-ala, i.e., 3-aminopropionic, 4-aminobutyric) or large (all others).

Other amino acid substitutions for those encoded in the gene can also be included in peptide compounds within the scope of the invention and can be classified within this general scheme.

The nomenclature used to describe analog compounds of the present invention follows the conventional practice wherein the amino group is assumed to the left and the carboxy group to the right of each amino acid in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^+_2$ and C-terminal-$O^-$ at physiological pH are understood to be present though not necessarily specified and shown, either in specific examples or in generic formulas. However, a shared N linking two residues, where conventional peptide linkage is not present, is shown as [N]. Thus, in designating the substituted N-alkylcarboxy peptides and N-alkylcarboxyhydroxamic acid peptides, the structures are written by indicating the shared nitrogen as —[N]—. (Hydroxylamino in the N-alkylcarboxy hydroxamic peptides is abbreviated HA.) For example, analog #364, which is HOO-C—CH(CH$_2$Ph)—NH—CH$_2$CO—Gly-Arg-Ile-Asp-Arg-Ile-NH$_2$, where Ph is phenyl, is written as F[N]G-G-R-I-D-R-I-NH$_2$, and analog #702 which is the compound HONHCOCH(CH$_2$Ph)—NHCH$_2$CO—Gly-Arg-Ile-Asp-Arg-Ile-NH$_2$, is written as HAF[N]G-G-R-I-D-R-I-NH$_2$.

Additionally, when the peptide chain is not linked through the normal alpha-amino and carboxyl groups to form the peptide bond linking the residues, the following symbols are used: [gamma-L-Glu] denotes peptide linkage through the side-chain carboxyl group of L-Glu and the alpha-carboxyl group now becomes the free carboxylic acid side chain; similarly, the designations [gamma-D-Glu], [beta-L-Asp] and [beta-D-Asp] indicate linkages through the carboxyl not normally included in the peptide linkage.

In the peptides shown, each encoded residue where appropriate is represented by a single letter designation, corresponding to the trivial name of the amino acid, in accordance with the following conventional list:

| Amino Acid | One-Letter Symbol |
| --- | --- |
| Alanine | A |
| Arginine | R |
| Asparagine | N |
| Aspartic acid | D |
| Cysteine | C |

-continued

| Amino Acid | One-Letter Symbol |
|---|---|
| Glutamine | Q |
| Glutamic acid | E |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

The amino acids not encoded genetically are abbreviated as indicated above.

In the specific peptides shown in the present application, the L-form of any amino acid residue having an optical isomer is intended unless otherwise expressly indicated otherwise. While the residues of the invention peptides are normally in the natural L optical isomer form, one or two, preferably one, amino acid in addition to, as well as instead of, $AA_{110}$ and/or $AA_{113}$, may be replaced with the optical isomer D form (including embodiments where $AA_{110}$ and $AA_{113}$ are both D).

Free functional groups, including those at the carboxy- or amino-terminus, can also be modified by amidation, acylation or other substitution, which can, for example, change the solubility of the compounds without affecting their activity.

In particular, it has been discovered that carboxyl terminal amide-modified analogs are particularly potent and therefore preferred embodiments of the present invention. In general, the nitrogen atom of the amido group, covalently bound to the carbonyl carbon, will be $NH_2$, —NHR', or NR'R", wherein R' and R" are straight or branched chain alkyl or alkyl acyl of 1–10C, preferably 1–6C, including these groups wherein 1–2 carbons are replaced by nitrogen, oxygen or sulfur atoms. Representatives of such amido groups are: —$NH_2$, -$NHCH_3$, —$N(CH_3)_2$, —$NHCH_2CH_3$, —$NHC_6H_5$, —$NHCH_2CH(CH_3)_2$, —$NHCH_2CH(CH_3)CH_2CH_3$, —$NHCH_2CH_2OH$, —$NHCH_2OCH_2CH_3$ and —$N(CH_3)CH_2CH_2SCH_2CH_3$, among others.

The amidated compounds of the present invention be synthesized directly, for example using Boc-$AA_x$-pMBHA-Resin or Boc-$AA_x$-BHA-Resin, wherein $AA_x$ is the selected carboxy-terminal amino acid of the desired analog compound as described in further detail below. Alternatively, the compounds of the present invention can be chemically or enzymatically amidated subsequent to peptide synthesis using means well known to the art, or prepared by standard solution-phase peptide synthesis protocols.

PREFERRED EMBODIMENTS

A. The Core Pentapeptide

The compounds of the invention all contain the pentapeptide core sequence:

$AA_{109}$-$AA_{110}$-$AA_{111}$-$AA_{112}$-$AA_{113}$, wherein each of $AA_{109}$ and $AA_{112}$ is, independently:
a basic/noncyclic; or
a neutral/polar/large/nonaromatic amino acid residue;

in addition, $AA_{109}$ can be a neutral/nonpolar/large/nonaromatic amino acid;

$AA_{110}$ is a neutral/nonpolar/nonaromatic amino acid residue in the D or L configuration;

$AA_{111}$ is an acidic amino acid residue; and $AA_{113}$ is a neutral/nonpolar/large/nonaromatic amino acid residue in the D or L configuration, or is a covalent bond.

The most preferred sequence of this core is R(I/M)-DRI, wherein all residues are in the L configuration and the amino acid residues contained within the parentheses are alternatives. Next in preference are those sequences wherein only one of the R(I/M)DRI residues has been substituted by an alternative residue within the above definitions. Preferred substitutions are:

For $AA_{109}$, instead of R: K, (Acetyl)K, Q, N, L or Nle;

for $AA_{110}$, instead of I/M: V, V*, L, L*, I*, M*, t-BuA, t-BuG, or Cha;

for $A_{111}$, instead of D: E or Cya;

for $A_{112}$, instead of R: K, Q, N, Orn, or Cit;

for $A_{113}$, instead of I: M, M*, V, V*, L, L*, I*, N-MeIle, t-BuA, or a covalent bond.

(The * indicates the D form.)

Particularly preferred are those embodiments wherein this sequence is selected from the group consisting of:

| | RM*DRI | R(I/M)DRL |
|---|---|---|
| K(I/M)DRI | RLDRI | R(I/M)DRM |
| Q(I/M)DRI | R(I/M)ERI | R(I/M)DRM* |
| RVDRI | R(I/M)DKI | R(I/M)DRI* |
| RI*DRI | R(I/M)DQI | R(I/M)DRV | where the * indicates the D-form of the amino acid preceding it.

More than one alteration from the naturally occurring RIDRI or RMDRI sequence is within the scope of the invention, but less preferred. Particularly favored subsets of this group include those wherein glutamic replaces aspartic as $AA_{111}$ or lysine replaces arginine as $AA_{109}$, in addition to another substitution.

B. Embodiments of $Z_1$ $Z_1$ has the formula

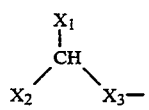

wherein $X_1$ is a hydrophobic cyclic or noncyclic residue of 4–14C;

$X_2$ is a substituent containing a metal coordinating atom within 1.5–7 angstroms of the illustrated CH, said metal coordinating atom selected from S and O; and —$X_3$— is a bond, —$CH_2$—, —CO—, or —NH—.

In order to provide inhibition of endopeptidase 24.11, both a hydrophobic residue and a metal-coordinating atom must be provided in proximity to each other. Accordingly, $X_1$ provides the hydrophobicity, and $X_2$ the metal coordinating atom.

The pivotal

group is a chiral center; accordingly the invention compounds include those in the R- and S- configuration or mixtures thereof. In general, the preferred enantiomer will be that wherein the chirality is such that an L-amino acid is mimicked.

—$X_3$— as shown provides linkage of the two essential features of the Z substituent to the remainder of the compound.

—$X_1$, in preferred embodiments, contains a cyclic or aromatic group conjugated to the illustrated CH through at least one $CH_2$, NH, O, or S linking group. Occasionally, this linking group may contain two members and thus includes —$OCH_2$—, —$CH_2O$—, —$CH_2S$—, —$SCH_2$—, —$CH_2CH_2$—, —$NHCH_2$—, or —$CH_2NH$—. The aromatic substituent may be phenyl, indolyl, biphenyl, naphthyl, pyridyl, imidazole, and the like, i.e., any 5–12 member ring system which can include one or two heteroatoms selected from N, O and S. In addition, the hydrophobic moiety may be nonaromatic such as, for example, cyclohexyl or any 5–10 membered nonaromatic ring system including one or two N, S or O heteroatoms. In some instances, the hydrophobic moiety may also be noncyclic.

—$X_2$, which contains the metal-coordinating atom, effects the appropriate separation of said atom from the illustrated CH. This separation is basically the space provided by 2–4 covalent bonds, or about 1.5–7 Å, and thus, —$X_2$ is exemplified by —$CH_2SH$, —$CH_2CH_2SH$, —COOH, —CONHOH, —$CH_2COOH$, —$CH_2CONHOH$, —$NHCH_2COOH$, —NHCHRCOOH, where R is —$CH_2Ph$ or —$CH_2CH_2Ph$, and $NHPO(OR')_2$ wherein each R' is independently H or alkyl (1–7C). When —$X_2$ is —$NHCH_2COOH$, —NHCHRCOOH, or —$NHPO(OR')_2$, the "N" will be bracketed [N] if $X_1$ represents an amino acid residue.

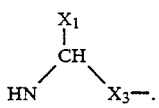

Illustrative and preferred embodiments of $Z_1$ (along with abbreviations therefor) are shown in FIGS. 2(A-Y). Especially preferred are compounds wherein $Z_1$ is such that $X_3$ is CO and $X_2$ is $CH_2SH$, or $X_3$ is CO and $X_2$ is CONOH, or $X_3$ is CO and $X_2$ is —$CH_2CONHOH$ or $X_3$ is CO and $X_2$ is [N]CHRCOOH where R is $CH_2Ph$ or $CH_2CH_2Ph$.

The illustrated CH is conjugated to the remainder of the compound of the invention through the linker —$X_3$—. The linker may simply be a bond to the spacer described as $Z_2$ or may be selected from —NH—, —CO—, and —$CH_2$—. When the spacer $Z_2$ is terminated by an amino acid residue, the structures illustrated below may show the NH which forms the N-terminus of the peptide as [N] i.e. N in brackets for convenience in decipherment.

C. Embodiments of $Z_2$

In the compounds of the invention, $Z_2$ provides a spacer element separating $AA_{109}$ from $Z_1$. The linker $Z_2$ must be capable to achieve a distance between $AA_{109}$ and $Z_1$ of about between 4.5 and 15 angstroms, corresponding to 3–9 atoms in a normally extended chain. Of course, longer linkers can be used provided their three-dimensional conformations permit this spacing distance to be accommodated.

Preferred embodiments for $Z_2$ are selected from the group consisting of (a) $(AA)_a$ wherein AA is an amino acid and "a" is 1 or 2, especially wherein each AA is selected from G, S, A, D-Ala, Sar, Aib, Asp, Glu, D-Asp, D-Glu, beta-L-Asp, beta-D-Asp, gamma-L-Glu, and gamma-D-Glu (in gamma-Glu and beta-Asp linkage is through the side-chain carboxyl);

(b) —$(P)_n$—$(CO)_x$— wherein x is 0 or 1, n is 1–6, and P is $CH_2$, wherein 1–2 of said —$CH_2$— groups can be replaced by NH, provided N—N does not occur; and (c) —$(Q)_m$—B—$(Q)_m$—$(CO)_x$— wherein x is 0 or 1, each m is independently 0–3 but the sum of both m is 5 or less; Q is $CH_2$ or NH, with the proviso that —N—N— does not occur, and B is a saturated or unsaturated five- or six-membered ring optionally containing an N heteroatom.

Particularly preferred embodiments of $Z_2$ are shown in FIG. 3. These include 4-aminobenzoyl(4-AB); 4-aminophenyl acetyl (4-APA); 4-piperidine carboxyl (4-PIP) and 4-aminomethyl cyclohexoyl (4-AMC).

D. Embodiments of $Z_3$

Preferred for $Z_3$ are $NH_2$, NHR", and the amide or alkyl amide of peptide residues of 1–3 amino acids. Especially preferred among the embodiments which are peptide residues are those wherein the amino acids are selected from G, A, and S. In particular, however, when $AA_{113}$ is a covalent bond, $Z_3$ should be in the alkyl amidated form, e.g., —NHR" wherein R' is 2–10C.

E. Nonpeptide Linkages

In one embodiment of the invention, the amide linkages (—CO—NH—) within the core pentapeptide or those described above within $Z_1$ and/or $Z_2$ and/or $Z_3$ can be replaced with other types of linkages such as —$CH_2NH$—, —$CH_2$—S—, —$CH_2CH_2$—, —CH=CH— (cis and trans), —$COCH_2$—, —$C(OH)CH_2$— and —$CH_2SO$—, by methods known in the art. The following references describe preparation of peptide analogs which include these alternative-linking moieties: Spatola, A. F., Vega Data (March 1983), Vol. 1, Issue 3, "Peptide Backbone Modifications" (general review); Spatola, A. F., in "Chemistry and Biochemistry of Amino Acids Peptides and Proteins", B. Weinstein, ed., Marcel Dekker, New York, p. 267 (1983) (general review); Morley, J. S., *Trends Pharm Sci* (1980) pp. 463–468 (general review); Hudson, D., et al, *Int J Pept Prot Res* (1979) 14:177–185 (—$CH_2NH$—, —$CH_2CH_2$—); Spatola, A. F., et al, *Life Sci* (1986) 38:1243–1249 (—$CH_2$—S); Hann, M. M., *J Chem Soc Perkin Trans I* (1982) 307–314 (—CH—CH—, cis and trans); Almquist, R. G., et al, *J Med Chem* (1980) 23:1392–1398 (—$COCH_2$—); Jennings-White, C., et al, *Tetrahedron Lett* (1982) 23:2533 (—$COCH_2$—); Szelke, M., et al, European Application EP 45665 (1982) CA: 97: 39405 (1982) (—$CH(OH)CH_2$—); Holladay, M. W., et al, *Tetrahedron Lett* (1983) 24:4401–4404 (—$C(OH)CH_2$—); and Hruby, V. J. *Life Sci* (1982) 31:189–199 (—$CH_2$—S—).

F. Preferred Embodiments of the Invention Analogs

Preferred analogs of the invention are shown in FIGS. 4(A-NN).

In the figure, in compounds 1–88, the core sequence is R-I-D-R-I, $Z_3$ is $NH_2$, $Z_2$ is $AA_a$, and $Z_1$ contains a mercaptyl group, where $X_2$— is —$CH_2SH$.

Compounds 89–110 are similar except that $Z_2$ is of the formula —$(P)_n$—$(CO)$— wherein n is 4–5.

Compounds 111–154 are similar except that $Z_2$ is selected from 4-AB, 4-AMC, 4-APA, and 4-PIP.

Compounds 155–220 are similar except that they have the core sequence K-I-D-R-I, $Z_3$ is $NH_2$.

Compounds 221–286 are similar except that they have core sequences R-I-D-R - NHR″ wherein R″ is $CH_2CH(CH_3)CH_2CH_3$.

Compounds 287–363 return to the R-I-D-R-I core peptide, $Z_3$ as $NH_2$, and embodiments of $Z_1$ wherein $X_2$ is —$CH_2CH_2SH$.

Compounds 364–624 all have the core sequence R-I-D-R-I with $Z_3$ as $NH_2$ in various preferred embodiments for $Z_2$, but $Z_1$ no longer contains a mercaptyl. $Z_1$ is selected from F[N], BF[N], Na12[N], Na11[N], Cha[N], W[N], homoF[N], homoCha[N], homoNa12[N], F[N]F, F[N]BF, F[N]Na12, F[N]Na11, F[N]Cha, F[N]W, F[N]homoF, F[N]homoCha, F[N]homoNa12, and similar structures wherein homoF[N] or G[N] substitutes for F[N]. Thus, in these embodiments $Z_1$ is

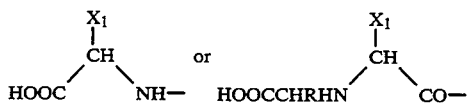

wherein R is —H, —$CH_2Ph$ or —$CH_2CH_2Ph$.

In compounds 625–701, $Z_1$ also contains a carboxyl group and is selected from embodiments wherein $X_2$— is COOH, and —$X_3$— is —CO—.

In compounds 702–764, $X_2$— contains a hydroxamate and $Z_1$ is

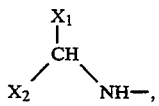

where $X_2$— is —CONHOH.

In compounds 765–841 $Z_1$ is

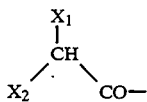

where $X_2$ is —CONHOH.

In compounds 842–918, $Z_1$ is

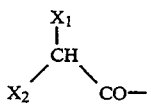

where $X_2$— is —$CH_2CONHOH$.

In compounds 919–981, $Z_1$ is

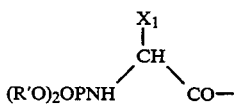

wherein $X_1$ is variable and $X_2$ is phosphoramidate as shown. In these embodiments, the various substituents shown in FIGS. 2(A-Y) for $Z_1$ which are aromatic amino acids are conjugated to the $Z_2$ substituent through their alpha-carboxyl groups and are phosphorylated at the alpha-amino groups. Thus, $Z_1$ has the structure shown as embodiments Z19-Z27 of FIGS. 2(A-Y).

In compounds 982–1056, $Z_1$ has the formula

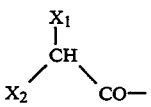

wherein $X_1$ is variable and $X_2$ is —$CH_2COOH$.

Especially preferred are compounds 1–286, 436–561, and 842–981, inclusive.

Compound 122 is particularly preferred.

SYNTHESIS

Compounds within the scope of the present invention can be synthesized chemically by means well known in the art such as, e.g., solid-phase peptide synthesis. The synthesis is commenced from the carboxy-terminal end of the peptide using an alpha-amino protected amino acid. t-Butyloxycarbonyl (Boc) protective groups can be used for all amino groups even though other protective groups are suitable. For example, Boc-Ile-OH, Boc-Arg-OH, Boc-Asp-OH, Boc-Ile-OH or Boc-Arg-OH (i.e., selected analog carboxy-terminal amino acids) can be esterified to chloromethylated polystyrene resin supports, preferably of p-methyl benzhydryl amine (pMBHA) resin. The polystyrene resin support is preferably a copolymer of styrene with about 0.5 to 2% divinyl benzene as a cross-linking agent which causes the polystyrene polymer to be completely insoluble in certain organic solvents. See Stewart, et al, *Solid-Phase Peptide Synthesis* (1969) W.H. Freeman Co., San Francisco and Merrifield, *J Am Chem Soc* (1963) 85:2149-2154. These and other methods of peptide synthesis are also exemplified by U.S. Pat. Nos. 3,862,925, 3,842,067, 3,972,859, and 4,105,602.

The synthesis may use manual techniques or automatically employing, for example, an Applied BioSystems 430A Peptide Synthesizer (Foster City, Calif.) or a Biosearch SAM II automatic peptide synthesizer (Biosearch, Inc. San Rafael, Calif.), following the instructions provided in the instruction manual supplied by the manufacturer.

It will be readily appreciated by those having ordinary skill in the art of peptide synthesis that the intermediates which are constructed in accordance with the present disclosure during the course of synthesizing the present analog compounds are themselves novel and useful compounds and are thus within the scope of the invention.

ADMINISTRATION AND USE

Compounds of the present invention are shown to have natriuretic, diuretic and hypotensive activity in the intact mammal, and may possess vasorelaxant activity or inhibit the release of aldosterone and renin.

Thus these compounds, and compositions containing them, can find use as therapeutic agents in the treatment of various edematous states such as, for example, congestive heart failure, nephrotic syndrome and hepatic cirrhosis, pulmonary disease, in addition to hypertension and renal failure due to ineffective renal perfusion or reduced glomerular filtration rate.

Thus the present invention also provides compositions containing an effective amount of compounds of the present invention, including the nontoxic addition salts, amides and esters thereof, which may, alone, serve to provide the above-recited therapeutic benefits. Such compositions can also be provided together with physiologically tolerable liquid, gel or solid diluents, adjuvants and excipients.

These compounds and compositions can be administered to mammals for veterinary use, such as with domestic animals, and clinical use in humans in a manner similar to other therapeutic agents. In general, the dosage required for therapeutic efficacy will range from about 0.01 to 1000 mcg/kg, more usually 0.1 to 1000 mcg/kg of the host body weight. Alternatively, dosages within these ranges can be administered by constant infusion over an extended period of time until the desired therapeutic benefits have been obtained.

Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10% preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contain 10%–95% of active ingredient, preferably 25%–70%.

The peptide compounds may be formulated into the compositions as neutral or salt forms. Pharmaceutically acceptable nontoxic salts include the acid addition salts (formed with the free amino groups) and which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In addition to the compounds of the present invention which display natriuretic, diuretic or vasorelaxant activity, compounds of the present invention can also be employed as intermediates in the synthesis of such useful compounds. Alternatively, by appropriate selection, compounds of the present invention whose activity levels are reduced or eliminated entirely can serve to modulate the activity of other diuretic, natriuretic or vasorelaxant compounds, including compounds outside the scope of the present invention, by, for example, binding to alternate receptors, stimulating receptor turnover, or providing alternate substrates for degradative enzyme or receptor activity and thus inhibiting these enzymes or receptors. When employed in this manner, such compounds can be delivered as admixtures with other active compounds or can be delivered separately, for example, in their own carriers.

Compounds of the present invention can also be used for preparing antisera for use in immunoassays employing labeled reagents, usually antibodies. Conveniently, the polypeptides can be conjugated to an antigenicity-conferring carrier, if necessary, by means of dialdehydes, carbodiimide or using commercially available linkers. These compounds and immunologic reagents may be labeled with a variety of labels such as chromophores, fluorophores such as, e.g., fluorescein or rhodamine, radioisotopes such as $^{125}I$, $^{35}S$, $^{14}C$, or $^{3}H$, or magnetized particles, by means well known in the art.

These labeled compounds and reagents, or labeled reagents capable of recognizing and specifically binding to them, can find use as, e.g., diagnostic reagents. Samples derived from biological specimens can be assayed for the presence or amount of substances having a common antigenic determinant with compounds of the present invention. In addition, monoclonal antibodies can be prepared by methods known in the art, which antibodies can find therapeutic use, e.g., to neutralize overproduction of immunologically related compounds in vivo.

EXAMPLES

The following examples are provided by way of illustration, rather than implying any limitation of the subject invention.

Compounds of the present invention were synthesized by solid-phase techniques performed manually or, alternatively, on an Applied BioSystems 430A Peptide Synthesizer (Foster City, California) or a Biosearch Sam II automated peptide synthesizer (Biosearch, San Rafael, Calif.) using t-Boc amino acids in accordance with the instructions of the manufacturer.

Residues $Z_2$-$AA_{109}$-$AA_{113}$ are commonly prepared on solid-phase supports using conventional t-Boc chemistry. Where applicable, $Z_2$ spacers are incorporated into the peptide chain using BOC-$Z_2$ protected intermediates that are conveniently prepared from the corresponding $NH_2$-$Z_2$-COOH and Boc-anhydride. The spacers are coupled to the free amino group on the growing peptide chain using standard carboxyl activating agents such as dicyclohexylcarbodiimide (DCC). For peptides which contain the 3-mercapto-2-(substituted)-propionyl, examples (1–286), or 4-mercapto-2-(substituted)-butyryl amino terminus, examples (287–363), the corresponding protected 3-Acetylthio- or 3-Benzoylthio-2-(substituted)-propionic or 4-acetylthio or 4-Benzoylthio-2-(substituted)-butyric acids are used. The S-acetyl or S-benzoyl groups are later removed by base hydrolysis as described by Fournie-Zaluski et al, *Eur J Biochem* (1984) 139:267–274. For examples containing the substituted malonoyl or succinoyl groups, examples (625–918), generally the methods found in Fournie-Zaluski et al, *J Med Chem* (1985) 28:1158–1169 can be used for their incorporation into the peptide-resins. For peptides containing the (N-hydroxy)carboxamido-2-(substituted)-1-oxo-acetyl group referred to as hydroxyamino malonoyl and 3-(N-hydroxy)carboxamido-2-(substituted)-1-oxo propyl groups referred to as hydroxyamino succinoyl groups, these groups can be introduced according to the methods outlined in Fournie-Zaluski, supra, and in Fr. patent 81.23.488. The N-carboxyalkyl-containing peptides, examples (364–624), are prepared using the methods of Fournie-Zaluski et al, *J Med Chem* (1983) 26:60–65, Patchett et al, *Nature* (1980) 288:280–283, or Mumford et al, *Biochem Biophys Res Commun* (1982) 109:1303–1309. N-alkylation is routinely carried out with the corresponding substituted alpha-ketocarboxylic acid or ester by reductive amination of the free amino group on the peptide resin. N-Phosphoryl peptides, examples (919–981), can be obtained using the procedures outlined in Kam et al, *Biochemistry* (1979) 18:3032–3038.

PROCEDURE A

Preparation of Boc-AA1 . . . AAn-1-AAn-O-Polystyrene Resin

One gram of selected Boc-AA$_n$-O-Polystyrene-Resin (0.2–0.6 mmole/g resin) (obtainable from, e.g., Peninsula Labs, Inc.) is treated according to schedule A for incorporation of the Boc-AA$_{n-1}$-OH.

SCHEDULE A

1) Wash 3× with dichloromethane ($CH_2Cl_2$);
2) Treat for 1 min with TFA:$CH_2Cl_2$:ethane dithiol (EDT) (45:50:5 by volume);
3) Treat for 20 min. with TFA:$CH_2Cl_2$:EDT (45:50:5 by volume);
4) Wash 3× with $CH_2Cl_2$;
5) Treat 2× for 1 min. 10% (v/v) Diisopropylethylamine (DIPEA) in $CH_2Cl_2$;
6) Wash 2× with $CH_2Cl_2$;
7) Wash 2× with methanol (MeOH);
8) Repeat (5–7) once;
9) Wash 3× with $CH_2Cl_2$;
10) Add 1–6 equivalents of preformed symmetrical anhydride of the suitably protected Boc-amino acid dissolved in $CH_2Cl_2$ or dimethyl formamide (DMF)/$CH_2Cl_2$ (50:50 volume), (Boc-Asn-OH, Boc-Gln-OH and Boc-Arg(TOS)-OH were coupled as active esters using N-hydroxybenzotriazole);
11) Wash 2× wth $CH_2Cl_2$;
12) Wash 2× wth 10% DIPEA;
13) Wash 2× wth $CH_2Cl_2$;
14) Wash 2× wth MeOH;
15) Wash 2× wth $CH_2Cl_2$;
16) Repeat steps (11–15) once;
17) Test by ninhydrin reaction according to Kaiser et al, *Anal Biochem* 34:595 (1970). If the coupling reaction was incomplete, repeat steps (10–16) or, alternatively, cap synthesis using N-acetyl imidazole (0.30M in DMF) or an excess of acetic anhydride in $CH_2CL_2$.

PROCEDURE B

Preparation of Boc-AA$_n$-p-Methylbenzhydrylamine resin

The selected Boc-AA$_n$-OH is attached to a p-Methylbenzhydrylamine (pMBHA) resin via N,N'-dicyclohexylcarbodiimide, as described below.

SCHEDULE B

1) Wash the pMBHA HCl resin;
2) Wash the resin 2× wth 10% (v/v) DIPEA in $CH_2Cl_2$;
3) Wash 2× wth $CH_2Cl_2$;
4) Wash 2× wth MeOH;
5) Wash 2× wth $CH_2Cl_2$;
6) Add 1–6 equivalents of preformed symmetrical anhydride of the suitably protected Boc-amino acid dissolved in $CH_2Cl_2$, with reaction time of 0.5–24 hrs.

Unreacted amino groups are acetylated with 0.30/M N-acetylimidazole:DMF, or acetic anhydride:$CH_2Cl_2$.

The following examples demonstrate the chemical synthesis of representative analog compounds (identified as Analog #) which illustrate certain aspects of the present invention.

EXAMPLE 1

Preparation of Analog #1:

MBP-G-G-R-I-D-R-I-NH$_2$

One gram of pMBHA resin (0.25 meq/g, Applied Biosystems, Foster City, Calif.) was subjected to procedure B followed by schedule A with the required sequence of amino acids (introduced in order as Boc-Ile-OH, Boc-Arg(Tos)-OH, Boc-Asp(O-cHexyl)-OH, Boc-Ile-OH, Boc-Arg(Tos)-OH, Boc-Gly-OH). After deprotection of the Boc- group followed by neutralization, the MBP-G- group was added using a carboxyl activated form of (D,L)-thiorphan. This was accomplished by treatment of (D,L)-thiorphan (100 mg, 0.39 mmol, Bachem Biosciences, Philadelphia, Pa.) with N-hydroxybenzotriazole (0.39 mmol, 1 eq) and 1 eq of 1M DCC in $CH_2Cl_2$ to form the activated ester of (D,L)-thiorphan which was reacted with the deprotected peptide resin in 50/50 $CH_2Cl_2$/DMF for 4 hr. The resin was washed 3× wth $CH_2Cl_2$ and twice with MeOH and dried in vacuo.

The peptide resin was treated with anhydrous hydrogen fluoride (HF) containing 10% anisole, 2% ethyl methyl sulfide for 30 min. at −10° C., and an additional 30 min. at 0° C. The HF was removed in vacuo and the peptide/resin mixture was suspended in diethyl ether followed by alternately washing with chloroform and ether 3×. After a final ether wash, the peptide was extracted from the resin with 2.0M acetic acid, diluted with distilled water and lyophilized.

Purification of the crude peptide was achieved by desalting on Sephadex G-25F (Pharmacia) using 0.5M acetic acid as eluant, followed by cation exchange chromatography on CM-Sepharose (Pharmacia) or CM-cellulose (Whatman) using an elution gradient of NH$_4$OAc. Fractions were analyzed by reversed-phase liquid chromatography on a Vydac C18 column using a 15–35% acetonitrile gradient containing 0.1% trifluoroacetic acid (TFA). Semipreparative HPLC gave purified peptide #1 as judged by amino acid analysis.

EXAMPLE 2

Preparation of Analog #445:

F[N]F-4-APA-R-I-D-R-I-NH$_2$

One gram of pMBHA resin (0.45 meq/g, U.S. Biochemical) was subjected to procedure B followed by schedule A with the required sequence of amino acids (introduced in order as Boc-Ile-OH, Boc-Arg(Tos)-OH, Boc-Asp(O-cHexyl)-OH, Boc-Ile-OH, Boc-Arg(Tos)-OH, Boc-p-aminophenylacetic acid (Boc-4-APA-OH), half-maximal inhibition of ANP binding as Ki(app) in units of nanomoles/liter.

TABLE 1

| | BASM Receptor Binding Assay | |
|---|---|---|
| Analog | Structure | Ki(app)(nM) |
| | rANP(102-126) | 7.5 |
| 12 | MBP—D—G—R—I—D—R—I—NH$_2$ | 207.4 |
| 23 | MBP—[D-Asp]—G—R—I—D—R—I—NH$_2$ | 115.4 |
| 78 | MBP—[γ-Glu]—R—I—D—R—I—NH$_2$ | 201.8 |
| 122 | MBP-4-APA—R—I—D—R—I—NH$_2$ | 10.9 |
| 364 | F—[N]—G—G—R—I—D—R—I—NH$_2$ | 66.9 |
| 427 | F—[N]—beta-Ala]—G—R—I—D—R—I—NH$_2$ | 11.5 |
| 436 | F—[N]—F—G—G—R—I—D—R—I—NH$_2$ | 27.3 |
| 445 | F—[N]—F-4-APA—R—I—D—R—I—NH$_2$ | 6.5 |
| 463 | F—[N]—F—D—G—R—I—D—R—I—NH$_2$ | 225.4 |
| 544 | homoF—[N]—F—[γ-Glu]—R—I—D—R—I—NH$_2$ | 58.2 |
| 702 | HAF—[N]—G—G—R—I—D—R—I—NH$_2$ | 4.6 |
| 1 | MBP—G—G—R—I—D—R—I—NH$_2$ | 19.6 |

Boc-Phe-OH). Following deprotection of the Boc-group and neutralization, reductive amination of the free amine was conducted by treatment with phenylpyruvic acid (246 mg, 1.5 meq, Aldrich) in the presence of catalytic acetic acid (100 ul) and 95 mg of NaCNBH$_3$ in DMF at room temperature for 1 day. The resin was then washed with DMF and CH$_2$Cl$_2$ extensively, followed by MeOH and dried in vacuo.

The peptide resin was treated with anhydrous hydrogen fluoride (HF) containing 10% anisole, 2% ethyl methyl sulfide for 30 min. at $-10°$ C., and an additional 30 min. at $0°$ C. The HF was removed in vacuo and the peptide/resin mixture was suspended and stirred with diethyl ether for 20 min. This mixture was alternately washed with chloroform and ether 3×. After a final ether wash, the peptide was extracted from the resin with 2.0M acetic acid, diluted with distilled water and lyophilized.

Purification of the crude peptide was achieved by cation exchange chromatography on CM-Sepharose (Pharmacia) or CM-cellulose (Whatman) using an elution gradient of NH$_4$OAc. Final purification of the peptide was accomplished by semi-preparative HPLC on a Vydac C18 column using a 15-35% acetonitrile gradient containing 0.1% TFA. Amino acid analysis confirmed the structure of peptide #445.

EXAMPLE 3

Binding to ANP Clearance Receptor

The assay systems used are adapted from those of Schenk, D. B., et al, *Biochem Biophys Res Commun* (1985) 127:433–442 and Scarborough, R. M., *J Biol Chem* (1986) 261:12960–12964. These assays measure clearance receptor binding affinity through competition with ANP using the receptors on bovine aortic smooth muscle (BASM) or bovine aortic endothelial (BAE) cells. Also employed is the receptor binding affinity assay for the clearance receptor in isolated perfused rat kidney as described by Maack, T., et al, *Science* (1987) 238:675–679.

Illustrative compounds of the invention were tested in the BASM assay using I$^{125}$ labeled rANP (102–126) with the iodine substituted at the tyrosine at 126. The results shown as the concentration at which 50% maximal binding of the labeled standard to BASM cells is displaced is designated Ki(app). Thus, the lower the Ki(app), the more effective the binding of the analog.

Table 1 shows the results of this competition binding assay with the concentration of analog required for In the rat kidney receptor binding assay, the native 28-residue labeled ANP was used: I$^{125}$ labeled rANP(-99–126), with the label linked to tyrosine at 126. The results of this assay are shown in Table 2 as the ratio of bound-to-free labeled rANP(99–126) in the presence and absence of competing compound. As shown in Table 2, analog 436 successfully competes with the labeled compound for receptor.

TABLE 2

| Ratio of Bound/Free ($^{125}$I)rANP(99-126) | |
|---|---|
| Compound | Whole Kidney |
| labeled compound (4 × 10$^{-12}$M) (n = 8) | 59 ± 16 |
| labeled compound (4 × 10$^{-12}$M) + rANP(99-126) (1 × 10$^{-6}$M) (n = 2) | 0.56 |
| labeled compound (4 × 10$^{-12}$M) + #436 (1 × 10$^{-6}$M) (n = 2) | 1.31 |

EXAMPLE 4

Inhibition of Endopeptidase 24.11

Endopeptidase 24.11 inactivates ANP by cleavage at the Cys$^{105}$-Phe$^{106}$ amide bond. The ability of the compounds of the invention to inhibit this degradation was assayed by a modification of the procedure of Ura, N., et al, *Kidney Int* (1987) 32:507–513 by substituting rANP(99–126) for bradykinin as a substrate.

Briefly, rat urine was collected and desalted on Sephadex G-25 as described by Ura (supra) and 4 ul of sample in 100 ul 0.1M Tris buffer, pH 7.2 containing aminopeptidase inhibitor bestatin (10 ug/ml), potato tuber carboxy peptidase inhibitor (10 ug/ml) and aprotinin (5,000 kalikrein inhibitory unit/ml) were incubated for 15 min at 37° C. The assay was then initiated by addition of 2–10 ug rANP(99–126) to a final volume of 0.5 ml and incubated at 10–20 min at 37° C. Termination of the reaction was accomplished by boiling, spinning and freezing.

Compounds to be tested for their ability to inhibit the endopeptidase were added to the preincubation mixture 15 min before addition of substrate.

The frozen samples, incubated with or without inhibitor, were thawed and analyzed by HPLC to determine the concentration of starting rANP(99-126) and its degradation product. HPLC analysis was conducted on Vydac C18 reverse phase HPLC column (4.6 mm ID × 12.5 cm; 5 uM, 300A). A linear gradient of 15–35% acetonitrile containing 0.1% TFA was run at 1.0 ml/min on a Perkin-Elmer series 4 HPLC system. The effluent was monitored at 220 nm and the peptide peak heights measured.

The results were computed as the percent of the $Cys^{105}$-$Phe^{106}$ cleavage metabolite peak in the test sample as compared to the peak height for this metabolite in the control. The results are shown in Table 3.

TABLE 3

| | % Inhibition of Metabolite Formation | | | | | |
|---|---|---|---|---|---|---|
| Dose | Thiorphan | Phosphor-amidon | 122 | 1 | 526 | 445 |
| 10 uM | 92 | 97 | 97 | 92 | 20 | 0 |
| 1 uM | 67 | 80 | 72 | 45 | 0 | — |
| 100 nM | 53 | 30 | 25 | 23 | — | — |
| 20 nM | 12 | 0 | 12 | 0 | — | — |

As shown in Table 3, analog #1 of the invention, though less potent than thiorphan as an inhibitor, is capable of inhibition with an $ED_{50}$ of approximately 1 uM. Furthermore, analog #122 is only slightly less potent than thiorphan and is comparable to phosphoramidon.

EXAMPLE 5

In Vivo Assays

The ability of analog #1 to effect diuresis and natriuresis in whole animals was determined as follows. Female Sprague-Dawley rats (230–260 g) anesthetized with inactin (100 mg/kg body weight) were catheterized by placing cannulae in femoral artery (B.P. monitoring), femoral vein (infusion of drugs and saline) and bladders (collection of urine). Post surgery, and prior to administration of test substance, saline was infused at 20 ul/min for 45 min in order to stabilize urine flow. Stabilization of urine flow was determined by collection of urine during several 10 min periods. Once stable urine flow was obtained, three 10 min control periods were collected followed by infusion of test compounds at 20 ul/min for 1 hr after priming with 10 times the infusion dose. Following experimental infusion period, saline was infused at 20 ul/min for 2 additional hr during the recovery phase. The urine volume collected during ten minute collection periods was determined gravimetrically. Urinary sodium excretion $U_{Na}V$ was determined photometrically. For comparison, Table 4 shows the effects of 300 ng/kg/min infusion of hANP(102-126) and compound #1.

TABLE 4

| Comparative Effects of hANP(102-126) and #437 in Rats | | |
|---|---|---|
| | V(ul/min) | $U_{Na}V$(uEq/min) |
| hANP(102-126) 300 ng/kg/min | 16.8 ± 9.3 | 2.24 ± 0.77 |
| #1 10 ug/kg/min | 11.6 ± 2.7 | 3.72 ± 1.1 |
| Control Saline | 3.5 ± 1.0 | 0.13 ± 0.04 |

Differences (Δ) between experimental and control periods (mean ± SE) in rats infused with compound (n = 7).

The specific effects of compounds on natriuresis and diuresis in anesthetized rats are shown in FIGS. 5A–5D. Percent and absolute increase ±SE for natriuresis and diuresis are displayed in these figures. Analog #1 infused at 10 ug/kg/min gives a mean 10-fold increase in urinary sodium excretion and a 2- to 3-fold increase in urinary flow rate. Maximal effects are not observed until the second or third experimental collection period and are sustained through the infusion. Slow return to baseline urine flow and sodium excretion rates are observed for Analog #1 compared to effects with ANP(1-02-126) and are consistent with the concept that clearance mechanisms once inhibited require significant time before they can fully participate in ANP clearance.

I claim:

1. A linear peptide compound having natriuretic, diuretic and/or vasodilator activity in mammals, which has the formula:

$$Z_1Z_2\text{-}AA_{109}\text{-}AA_{110}\text{-}AA_{111}\text{-}AA_{112}\text{-}AA_{113}\text{-}Z_3 \quad (1)$$

wherein $AA_{109}$-$AA_{110}$-$AA_{111}$-$AA_{112}$-$AA_{113}$ is selected from the group consisting of

| | | |
|---|---|---|
| R(I/M)DRI | RM DIR | R(I/M)DRL |
| K(I/M)DRI | RLDRI | R(I/M)DRM |
| Q(I/M)DRI | R(I/M)ERI | R(I/M)DRM |
| RVDRI | R(I/M)DKI | R(I/M)DRI and |
| DI DRI | R(I/M)DQI | R(I/M)DRV | wherein indicates the D form of the amino acid preceding it; and wherein $Z_1$ is

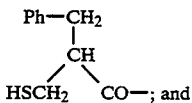
; and wherein $Z_2$ is a spacer group capable of providing a spaced dimension of 4.5–15 angstroms between $AA_{109}$ and the $PhCH_2$— of $Z_1$ selected from the group consisting of (a) —$(AA)_a$— wherein AA is an amino acid and a is 1 or 2;

(b) —$(P)_n$—$(CO)$—$_x$ wherein x is 0 or 1, n is 1–6, and P is $CH_2$ wherein 1–2 of said —$CH_2$— groups can be replaced by NH, provided N-N does not occur; and (c) —$(O)_m$—B—$(O)_m$—$(CO)_x$— wherein x is 0 or 1, each m is 0–3, wherein the sum of m is 5 or less, —B— is a saturated or unsaturated five- or six-membered ring optionally containing an N heteroatom, and O is $CH_2$ or NH, provided —N—N— does not occur;

$Z_3$ is (OH), $NH_2$, or NHR″ wherein R″ is alkyl (1–10C); and wherein one or more of the amide linkages between adjacent amino acid residues may optionally be replaced by a linkage selected from the group consisting of —$CH_2NH$—, —$CH_2S$—, —$CH_2CH_2$—, —CH=CH—, —$COCH_2$—, —$CH(OH)CH_2$— and —$CH_2SO$—.

2. The compound of claim 1 wherein $AA_{109}$-$AA_{110}$-$AA_{111}$-$AA_{112}$-$AA_{113}$- is RIDRI, and $Z_3$ is $NH_2$.

3. The compound of claim 2 wherein $Z_2$ is 4-APA.

4. The compound of claim 3 which is analog #122: MBP-4-APA-R-I-D-R-I-$NH_2$.

5. A composition useful as a natriuretic, diuretic and/or vasodilator comprising a therapeutically effective amount of the compound of claim 1 together with a pharmaceutically acceptable carrier.

6. A method for enhancing natriuresis, diuresis, and/or vasodilation in a mammalian host, which comprises administering to said host a pharmaceutically effective amount of the composition of claim 5.

7. A process for production of a peptide compound having natriuretic, diuretic and/or vasodilator activity in mammals, said peptide compound having the formula of the compound of claim 1, or the pharmacologically acceptable salts thereof, which process comprises the following steps:
   a. preparing a protected peptide bonded to a solid resin carrier in a reaction mixture, wherein the peptide has an amino acid sequence as recited above;
   b. removing the solid resin carrier from the peptide and deprotecting the peptide;
   c. optionally modifying the peptide to add any desired organic substituent groups as recited above; and
   d. isolating the peptide from any reaction mixture, and optionally, converting the polypeptide into an acid addition salt thereof.

8. The compound of claim 1 wherein $Z_2$ is selected from the group consisting of —G—G—, —D—G—, —G—; D, D , E or E , wherein linkage to Z is through the side-chain carboxyl; 4-AB, 4-APA, 4-PIP and 4-AMC.

9. The compound of claim 1 which is analog no. —1: MBP-G-G-R-I-D-R-I-NH$_2$.

10. The compound of claim 1 which is MBP-4-APA-R-M-D-R-I-NH$_2$ or MBP-G-G-R-M-D-R-I-NH$_2$.

* * * * *